(12) United States Patent
Lei

(10) Patent No.: US 7,919,297 B2
(45) Date of Patent: Apr. 5, 2011

(54) **MUTANTS OF *ASPERGILLUS NIGER* PHYA PHYTASE AND *ASPERGILLUS FUMIGATUS* PHYTASE**

(75) Inventor: Xingen Lei, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 788 days.

(21) Appl. No.: 11/677,509

(22) Filed: Feb. 21, 2007

(65) Prior Publication Data

US 2007/0196449 A1 Aug. 23, 2007

Related U.S. Application Data

(60) Provisional application No. 60/775,258, filed on Feb. 21, 2006.

(51) Int. Cl.
*C12N 9/16* (2006.01)
*C12Q 1/34* (2006.01)

(52) U.S. Cl. .................. 435/196; 435/252.3; 435/320.1; 435/18; 536/23.2

(58) Field of Classification Search .................. 435/196, 435/252.3, 320.1; 426/615, 623; 536/23.2
See application file for complete search history.

(56) References Cited

U.S. PATENT DOCUMENTS

| | | |
|---|---|---|
| 3,819,528 A | 6/1974 | Berry |
| 3,860,484 A | 1/1975 | O'Malley |
| 3,966,971 A | 6/1976 | Morehouse et al. |
| 4,038,140 A | 7/1977 | Jaworek et al. |
| 4,375,514 A | 3/1983 | Siewert et al. |
| 4,460,683 A | 7/1984 | Gloger et al. |
| 4,470,968 A | 9/1984 | Mitra et al. |
| 4,734,283 A | 3/1988 | Sirén |
| 4,765,994 A | 8/1988 | Holmgren |
| 4,778,761 A | 10/1988 | Miyanohara et al. |
| 4,914,029 A | 4/1990 | Caransa et al. |
| 4,915,960 A | 4/1990 | Holmgren |
| 4,950,609 A | 8/1990 | Tischer et al. |
| 4,997,767 A | 3/1991 | Nozaki et al. |
| 5,024,941 A | 6/1991 | Maine et al. |
| 5,200,399 A | 4/1993 | Wettlaufer et al. |
| 5,268,273 A | 12/1993 | Buckholz |
| 5,290,765 A | 3/1994 | Wettlaufer et al. |
| 5,316,770 A | 5/1994 | Edwards, Jr. |
| 5,318,903 A | 6/1994 | Bewert et al. |
| 5,366,736 A | 11/1994 | Edwards, Jr. |
| 5,436,156 A | 7/1995 | Van Gorcom et al. |
| 5,443,979 A | 8/1995 | Vanderbeke et al. |
| 5,480,790 A | 1/1996 | Tischer et al. |
| 5,492,821 A | 2/1996 | Callstrom et al. |
| 5,516,525 A | 5/1996 | Edwards, Jr. |
| 5,554,399 A | 9/1996 | Vanderbeke et al. |
| 5,556,771 A | 9/1996 | Shen et al. |
| 5,593,963 A | 1/1997 | Van Ooijen et al. |
| 5,612,055 A | 3/1997 | Bedford et al. |
| 5,691,154 A | 11/1997 | Callstrom et al. |
| 5,716,655 A | 2/1998 | Hamstra et al. |
| 5,736,625 A | 4/1998 | Callstrom et al. |
| 5,780,292 A | 7/1998 | Nevalainen et al. |
| 5,827,709 A | 10/1998 | Barendse et al. |
| 5,830,696 A | 11/1998 | Short |
| 5,830,733 A | 11/1998 | Nevalainen et al. |
| 5,834,286 A | 11/1998 | Nevalainen et al. |
| 5,853,779 A | 12/1998 | Takebe et al. |
| 5,863,533 A | 1/1999 | Van Gorcom et al. |
| 5,876,997 A | 3/1999 | Kretz |
| 5,891,708 A | 4/1999 | Saniez et al. |
| 5,900,525 A | 5/1999 | Austin-Phillips et al. |
| 5,902,615 A | 5/1999 | Saniez et al. |
| 5,935,624 A | 8/1999 | DeLuca et al. |
| 5,955,448 A | 9/1999 | Colaco et al. |
| 5,972,669 A | 10/1999 | Harz et al. |
| 5,985,605 A | 11/1999 | Cheng et al. |
| 5,989,600 A | 11/1999 | Nielsen et al. |
| 6,022,555 A | 2/2000 | DeLuca et al. |
| 6,039,942 A | 3/2000 | Lassen et al. |
| 6,063,431 A | 5/2000 | Bae et al. |
| 6,083,541 A | 7/2000 | Hamstra et al. |
| 6,110,719 A | 8/2000 | Kretz |
| 6,139,892 A | 10/2000 | Fredlund et al. |
| 6,139,902 A | 10/2000 | Kondo et al. |
| 6,140,077 A | 10/2000 | Nakamura et al. |
| 6,183,740 B1 | 2/2001 | Short et al. |
| 6,190,897 B1 | 2/2001 | Kretz |
| 6,204,012 B1 | 3/2001 | Hellmuth et al. |
| 6,248,938 B1 | 6/2001 | Austin-Phillips et al. |
| 6,261,592 B1 | 7/2001 | Nagashima et al. |
| 6,264,946 B1 | 7/2001 | Müllertz et al. |

(Continued)

FOREIGN PATENT DOCUMENTS

CN 1126243 A 7/1996

(Continued)

OTHER PUBLICATIONS

ATCC Catalog for Yeasts, 19th Edition (1995).
Belin et al., "A Pleiotropic Acid Phosphatase-Deficient Mutant of *Escherichia coli* Shows Premature Termination in the *dsbA* Gene. Use of *dsbA::phoA* Fusions to Localize a Structurally Important Domain in DsbA," *Mol. Gen. Genet.* 242:23-32 (1994).
Blondeau et al., "Development of High-Cell-Density Fermentation for Heterologous Interleukin 1β Production in *Kluyveromyces lactis* Controlled by the PHO5 Promoter," *Appl. Microbiol. Biotechnol.* 41:324-329 (1994).
Boctor et al., "Enhancement of the Stability of Thrombin by Polyols: Microcalorimetric Studies," *J. Pharm. Pharmacol.* 44:600-603 (1992).
Atlung et al., "Role of the Transcriptional Activator AppY in Regulation of the *cyx appA* Operon of *Escherichia coli* by Anaerobiosis, Phosphate Starvation, and Growth Phase," *J. Bacteriol.* 176(17):5414-5422 (1994).

(Continued)

*Primary Examiner* — Tekchand Saidha
(74) *Attorney, Agent, or Firm* — LeClairRyan

(57) ABSTRACT

The present invention is directed to an isolated nucleic acid molecule encoding mutant phytases and the isolated mutant phytases themselves. The present invention further relates to methods of using the isolated nucleic acid molecules and the isolated mutant phytases of the present invention.

18 Claims, 11 Drawing Sheets

U.S. PATENT DOCUMENTS

| | | |
|---|---|---|
| 6,274,178 B1 | 8/2001 | Beven et al. |
| 6,277,623 B1 | 8/2001 | Oh et al. |
| 6,284,502 B1 | 9/2001 | Maenz et al. |
| 6,291,221 B1 | 9/2001 | Van Loon et al. |
| 6,309,870 B1 | 10/2001 | Kondo et al. |
| 6,350,602 B1 | 2/2002 | Van Gorcom et al. |
| 6,391,605 B1 | 5/2002 | Kostrewa et al. |
| 6,451,572 B1 | 9/2002 | Lei |
| 6,475,762 B1 | 11/2002 | Stafford et al. |
| 6,511,699 B1 | 1/2003 | Lei |
| 6,514,495 B1 | 2/2003 | Svendsen et al. |
| 6,599,735 B1 | 7/2003 | Bartok et al. |
| 6,720,174 B1 | 4/2004 | Lehmann |
| 6,841,370 B1 | 1/2005 | Lei |
| 6,974,690 B2 | 12/2005 | Lei |
| 7,022,371 B2 | 4/2006 | Stafford et al. |
| 7,026,150 B2 | 4/2006 | Lei |
| 2001/0018197 A1 | 8/2001 | Wong et al. |
| 2001/0029042 A1 | 10/2001 | Fouache et al. |
| 2002/0068350 A1 | 6/2002 | Kondo et al. |
| 2002/0102692 A1 | 8/2002 | Lei |
| 2002/0127218 A1 | 9/2002 | Svendsen et al. |
| 2002/0136754 A1 | 9/2002 | Short et al. |
| 2003/0092155 A1 | 5/2003 | Kostrewa et al. |
| 2003/0206913 A1 | 11/2003 | Webel et al. |
| 2004/0126844 A1 | 7/2004 | Lei et al. |
| 2005/0095691 A1 | 5/2005 | Lei |
| 2006/0153902 A1 | 7/2006 | Lei |

FOREIGN PATENT DOCUMENTS

| | | |
|---|---|---|
| EP | 0 449 376 A2 | 10/1991 |
| EP | 0 556 883 A1 | 8/1993 |
| EP | 0 649 600 A1 | 4/1995 |
| EP | 0 684 313 A2 | 11/1995 |
| EP | 0 699 762 A2 | 3/1996 |
| EP | 0 772 978 B1 | 5/1997 |
| EP | 0 779 037 A1 | 6/1997 |
| EP | 0 897 010 A2 | 2/1999 |
| EP | 0 897 985 A2 | 2/1999 |
| EP | 0 909 821 A2 | 4/1999 |
| EP | 0 420 358 B1 | 5/1999 |
| EP | 0 925 723 A1 | 6/1999 |
| EP | 0 955 362 A1 | 11/1999 |
| EP | 0 960 934 A1 | 12/1999 |
| GB | 2 286 396 A | 8/1995 |
| GB | 2 316 082 A | 2/1998 |
| JP | 10-276789 | 10/1998 |
| JP | 2001-292789 | 10/2001 |
| RU | 2 113 468 C1 | 6/1998 |
| WO | WO 86/01179 A1 | 2/1986 |
| WO | WO 90/03431 A1 | 4/1990 |
| WO | WO 90/05182 A1 | 5/1990 |
| WO | WO 91/05053 A1 | 4/1991 |
| WO | WO 91/14773 A2 | 10/1991 |
| WO | WO 91/14782 A1 | 10/1991 |
| WO | WO 93/14645 A1 | 8/1993 |
| WO | WO 93/16175 A1 | 8/1993 |
| WO | WO 93/19759 A1 | 10/1993 |
| WO | WO 94/03072 A1 | 2/1994 |
| WO | WO 94/03612 A1 | 2/1994 |
| WO | WO 97/16076 A1 | 5/1997 |
| WO | WO 97/35017 A1 | 9/1997 |
| WO | WO 97/39638 A1 | 10/1997 |
| WO | WO 97/45009 A2 | 12/1997 |
| WO | WO 97/48812 A3 | 12/1997 |
| WO | WO 98/05785 A1 | 2/1998 |
| WO | WO 98/06856 A1 | 2/1998 |
| WO | WO 98/20139 A2 | 5/1998 |
| WO | WO 98/30681 A1 | 7/1998 |
| WO | WO 98/44125 A1 | 10/1998 |
| WO | WO 98/54980 A2 | 12/1998 |
| WO | WO 99/08539 A1 | 2/1999 |
| WO | WO 99/49022 A1 | 9/1999 |
| WO | WO 99/49740 A1 | 10/1999 |
| WO | WO 00/10404 A2 | 3/2000 |
| WO | WO 00/20569 A1 | 4/2000 |
| WO | WO 00/41509 A2 | 7/2000 |
| WO | WO 00/43503 A1 | 7/2000 |
| WO | WO 00/47060 A1 | 8/2000 |
| WO | WO 00/58481 A2 | 10/2000 |
| WO | WO 00/71728 A1 | 11/2000 |
| WO | WO 00/72700 A1 | 12/2000 |
| WO | WO 01/36607 A1 | 5/2001 |
| WO | WO 01/58275 A2 | 8/2001 |
| WO | WO 01/58276 A2 | 8/2001 |

OTHER PUBLICATIONS

Boer et al., "Characterization of *Trichoderma reesei* Cellobiohydrolase Cel7a Secreted from *Pichia pastoris* Using Two Different Promoters," *Biotechnol. Bioengin.* 69(5):486-494 (2000).

Brondsted et al., "Effect of Growth Conditions on Expression of the Acid Phosphatase (*cyx-appA*) Operon and the *appY* Gene, Which Encodes a Transcriptional Activator of *Escherichia coli*," *J. Bacteriol.* 178(6):1556-1564 (1996).

Chiarugi et al., "Differential Role of Four Cysteines on the Activity of a Low $M_r$ Phosphotyrosine Protein Phosphatase," *FEBS Lett.* 310(1):9-12 (1992).

Dassa et al., "Identification of the Gene *appA* for the Acid Phosphatase (pH Optimum 2.5) of *Escherichia coli*," *Mol. Gen. Genet.* 200:68-73 (1985).

Dassa et al., "The Complete Nucleotide Sequence of the *Escherichia coli* Gene *appA* Reveals Significant Homology Between pH 2.5 Acid Phosphatase and Glucose-1-Phosphatase," *J. Bacteriol.* 172(9):5497-5500 (1990).

Database Accession No. B36733, corresponding to Greiner et al., Arch. Biochem. Biophys. 303:107-113 (1993).

Divakaran et al., "In vitro Studies on the Interaction of Phytase with Trypsin and Amylase Extracted from Shrimp (*Penaeus vannamei*) Hepatopancreas," *J. Agric. Food Chem.* 46:4973-4976 (1998).

DSM Nutritional Products, Opposition Brief for European Patent No. EP 1-090-129 (10 pages) (Nov. 15, 2006).

Genbank Accession No. AAB96872 (Jan. 16, 1998).

Genbank Accession No. M94550 (Apr. 27, 1993).

Genbank Accession No. P34752 (Jan. 25, 2005).

Golovan et al., "Characterization and Overproduction of the *E. coli* appA Encoded Biofunctional Enzyme the Exhibits Both Phytase and Acid Phosphatase Activities," *Can. J. Microbiol.* 46:59-71 (2000).

Granovskii et al., "Expression of Hepatitis B Virus HBsAg Gene in Yeast Cells Under Control of Promotor Region of PHO5 Gene," *Soviet Progress in Virology* 5:45-47 (1985).

Greiner et al., "Purification and Characterization of a Phytase from *Klebsiella terrigena*," *Arch. Biochem. Biophys.* 341(2):201-206 (1997).

Greiner et al., "Purification and Characterization of Two Phytases from *Escherichia coli*," *Arch. Biochem. Biophys.* 303:107-113 (1993).

Han et al., "Development of Phytase Overexpressing Microbes for Nutritional Use," Poster Presentation at Cornell University's Biotechnology Symposium, Ithaca, New York (Oct. 15, 1997).

Han et al., "Expression of an *Aspergillus niger* Phytase Gene (*phyA*) in *Saccharomyces cerevisiae*," *Appl. Environ. Microbiol.* 65(5):1915-1918 (1999).

Han et al., "Role of Glycosylation in the Functional Expression of an *Aspergillus niger* Phytase (*phyA*) in *Pichia pastoris*," *Arch. Biochem. Biophys.* 364:83-90 (1999).

Jia et al., "Purification, Crystallization and Preliminary X-ray Analysis of the *Escherichia coli* Phytase," *Acta Cryst.* D54:647-649 (1998).

Kanai et al., "Recombinant Thermostable Cycloinulo-oligosaccharide Fructanotransferase Produced by *Saccharomyces cerevisiae*," *Appl. Environ. Microbiol.* 63(12):4956-4960 (1997).

Kerovuo et al., "Isolation, Characterization, Molecular Gene Cloning, and Sequencing of a Novel Phytase from *Bacillus subtilis*," *Appl. Environ. Microbiol.* 64(6):2079-2085 (1998).

Kim et al., "Cloning of the Thermostable Phytase Gene (*phy*) from *Bacillus* sp. DS11 and its Overexpression in *Escherichia coli*," *FEMS Microbiol. Lett.* 162:185-191 (1998).

Konietzny et al., "Model Systems for Developing Detection Methods for Foods Deriving from Genetic Engineering," *J. Food Comp. Anal.* 10:28-35 (1997).

Kostrewa et al., "Crystal Structure of *Aspergillus niger* pH 2.5 Acid Phosphatase at 2.4 Å Resolution," *J. Mol. Biol.* 288:965-974 (1999).

Kostrewa et al., "Crystal Structure of Phytase from *Aspergillus ficuum* at 2.5 Å Resolution," *Nat. Struct. Biol.* 4:185-190 (1997).

Kumagai et al., "Conversion of Starch to Ethanol in a Recombinant *Saccharomyces cerevisiae* Strain Expressing Rice α-amylase from a Novel *Pichia pastoris* Alcohol Oxidase Promoter," *Biotechnol.* 11:606-610 (1993).

Leeson et al., "Efficacy of New Bacterial Phytase in Poultry Diets," *Can. J. Anim. Sci.* 80:527-528 (2000).

Lehmann et al., "Exchanging the Active Site Between Phytases for Altering the Functional Properties of the Enzyme," *Protein Sci.* 9(10):1866-1872 (2000).

Lehmann et al., "From DNA Sequence to Improved Functionality: Using Protein Sequence Comparisons to Rapidly Design a Thermostable Consensus Phytase," *Protein Eng.* 13(1):49-57 (2000).

Lei et al., "Biotechnological Developments of Effective Phytases for Mineral Nutrition and Environmental Protection," *Appl. Microbiol. Biotech.* 57(4):474-481 (2001).

Lei et al., "Calcium Level Affects the Efficacy of Supplemental Microbial Phytase in Corn-Soybean Meal Diets of Weanling Pigs," *J. Anim. Sci.* 72(1):139-143 (1994).

Lei et al., "Nutritional Benefits of Phytase and Dietary Determinants of Its Efficacy," *J. Appl. Anim. Res.* 17:97-112 (2000).

Lei et al., "Supplemental Microbial Phytase Improves Bioavailability of Dietary Zinc to Weanling Pigs," *J. Nutr.* 123:1117-1123 (1993).

Lei et al., "Supplementing Corn-Soybean Meal Diets with Microbial Phytase Linearly Improves Phytate Phosphorus Utilization by Weanling Pigs," *J. Anim. Sci.* 71:3359-3367 (1993).

Lim et al., "Crystal Structure of *Escherichia coli* Phytase and its Complex with Phytate," *Nat. Struct. Biol.* 7(2): 108-113 (2000).

Lim et al., "Studies of Reaction Kinetics in Relation to the $T_g'$ of Polymers in Frozen Model Systems," in Levine, eds., *Water Relationships in Food*, New York, NY:Plenum Press, pp. 103-122 (1991).

Lozano et al., "Effect of Polyols on α-Chymotrypsin Thermostability: A Mechanistic Analysis of the Enzyme Stabilization," *J. Biotechnol.* 35:9-18 (1994).

Lozano et al., "Influence of Polyhydroxylic Cosolvents on Papain Thermostability," *Enzyme Microb. Technol.* 15:868-873 (1993).

Maugenest et al., "Cloning and Characterization of cDNA Encoding a Maize Seedling Phytase," *Biochem. J.* 322:511-517 (1997).

Meldgaard et al., "Different Effects of *N*-Glycosylation on the Thermostability of Highly Homologous Bacterial (1,3-1,4)-β-Glucanases Secreted from Yeast," *Microbiol.* 140(1):159-166 (1994).

Minamiguchi et al., "Secretive Expression of the *Aspergillus aculeatus* Cellulase (FI-CM Case) by *Saccharomyces cerevisiae*," *J. Ferment. Bioengin.* 79(4):363-366 (1995).

Mitchell et al., "The Phytase Subfamily of Histidine Acid Phosphatases: Isolation of Genes for Two Novel Phytases from the Fungi *Aspergillus terreus* and *Myceliophthora thermophila*," *Microbiol.* 143:245-252 (1997).

Moore et al., "Molecular Cloning, Expression and Evaluation of Phosphohydrolases for Phytate-Degrading Activity," *J. Industrial Microbiol.* 14:396-402 (1995).

Mullaney et al., "Advances in Phytase Research," *Adv. Appl. Microbiol.* 47:157-199 (2000).

Mullaney et al., "Phytase Activity in *Aspergillus fumigatus* Isolates," *Biochem. Biophys. Res. Commun.* 275:759-763 (2000).

Mullaney et al., "Positive Identification of a Lambda gt11 Clone Containing a Region of Fungal Phytase Gene by Immunoprobe and Sequence Verification," *Appl. Microbiol. Biotechnol.* 35:611-614 (1991).

Mullaney et al., "Site-Directed Mutagenesis of *Aspergillus niger* NRRL 3135 Phytase at Residue 300 to Enhance Catalysis at pH 4.0," *Biochem. Biophys. Res. Commun.* 297(4):1016-1020 (2002).

Murray et al., "Construction of Artificial Chromosomes in Yeast," *Nature* 305:189-193 (1983).

Murry et al., "The Effect of Microbial Phytase in a Pearl Millet-Soybean Meal Diet on Apparent Digestibility and Retention of Nutrients, Serum Mineral Concentration, and Bone Mineral Density of Nursery Pigs," *J. Animal Sci.* 75:1284-1291 (1997).

Nielsen et al., "The Determinants of α-Amylase pH-Activity Profiles," *Protein Eng.* 14(7):505-512 (2001).

Novozymes A/S, Opposition Brief for European Patent No. EP 1-090-129 (19 pages) (Nov. 2006).

Ostanin et al., "Asp$^{304}$ of *Escherichia coli* Acid Phosphatase is Involved in Leaving Group Protonation," *J. Biol. Chem.* 268(28):20778-20784 (1993).

Ostanin et al., "Overexpression, Site-Directed Mutagenesis, and Mechanism of *Escherichia coli* Acid Phosphatase," *J. Biol. Chem.* 267(32):22830-22836 (1992).

Pasamontes et al., "Gene Cloning, Purification, and Characterization of a Heat-Stable Phytase from the Fungus *Aspergillus fumigatus*," *Appl. Environ. Microbiol.* 63(5):1696-1700 (1997).

Phillippy et al., "Expression of an *Aspergillus niger* Phytase (*phyA*) in *Escherichia coli*," *J. Agric. Food Chem.* 45(8):3337-3342 (1997).

Piddington et al., "The Cloning and Sequencing of the Genes Encoding Phytase (*phy*) and pH 2.5-Optimum Acid Phosphatase (*aph*) From *Aspergillus niger* var. *awamori*," *Gene* 133:55-62 (1993).

Rodriguez et al., "Cloning, Sequencing, and Expression of an *Escherichia coli* Acid Phosphatase/Phytase Gene (*appA2*) Isolated from Pig Colon," *Biochem. Biophys. Res. Comm.* 257:117-123 (1999).

Rodriguez et al., "Different Sensitivity of Recombinant *Aspergillus niger* Phytase (r-PhyA) and *Escherichia coli* pH 2.5 Acid Phosphatase (r-AppA) to Trypsin and Pepsin In vitro," *Arch. Biochem. Biophys.* 365(2):262-267 (1999).

Rodriguez et al., "Expressison of the *Aspergillus fumigatus* Phytase Gene in *Pichia pastoris* and Characterization of the Recombinant Enzyme," *Biochem. Biophys. Res. Commun.* 268:373-378 (2000).

Rodriguez et al., "Site-Directed Mutagenesis Improves Catalytic Efficiency and Thermostability of *Escherichia coli* pH 2.5 Acid Phosphatase/Phytase Expressed in *Pichia pastoris*," *Arch. Biochem. Biophys.* 382:105-112 (2000).

Rossi et al., "Stabilization of the Restriction Enzyme *EcoRI* Dried with Trehalose and Other Selected Glass-Forming Solutes," *Biotechnol. Prog.* 13:609-616 (1997).

Schebor et al., "Glassy State and Thermal Inactivation of Invertase and Lactase in Dried Amorphous Matrices," *Biotechnol. Prog.* 13:857-863 (1997).

Scott et al., "The Effect of Phosphorus, Phytase Enzyme, and Calcium on the Performance of Layers Fed Corn-Based Diets," *Poultry Sci.* 78:1742-1749 (1999).

Sebastian et al., "Apparent Digestibility of Protein and Amino Acids in Brioler Chickens Fed a Corn-Soybean Diet Supplemented with Microbial Phytase," *Poultry Sci.* 76:1760-1769 (1997).

Sidhu et al., "Analysis of α-Factor Secretion Signals by Fusing with Acid Phosphatase of Yeast," *Gene* 54:175-184 (1987).

Sun et al., "Expression of *Aspergillus niger* Phytase in Yeast *Saccharomyces cerevisiae* for Poultry Diet Supplementation," *Poultry Sci.* 76(Suppl. 1):5 (1997).

Takahashi et al., "Independent Production of Two Molecular Forms of a Recombinant *Rhizopus oryzae* Lipase by *KEX2*-Engineered Strains of *Saccharomyces cerevisiae*," *Appl. Microbiol. Biotechnol.* 52(4):534-540 (1999).

Terashima et al., "The Roles of the N-Linked Carbohydrate Chain of Rice α-amylase in Thermostability and Enzyme Kinetics," *Eur. J. Biochem.* 226:249-254 (1994).

Tomschy et al., "Active Site Residue 297 of *Aspergillus niger* Phytase Critically Affects the Catalytic Properties," *FEBS Lett.* 472(2-3):169-172 (2000).

Tomschy et al., "Engineering of Phytase for Improved Activity at Low pH," *Appl. Environ. Microbiol.* 68(4):1907-1913 (2002).

Tomschy et al., "Optimization of the Catalytic Properties of *Aspergillus fumigatus* Phytase Based on the Three-Dimensional Structure," *Protein Sci.* 9(7):1304-1311 (2000).

Touati et al., "Pleiotropic Mutations in *appR* Reduce pH 2.5 Acid Phosphatase Expression and Restore Succinate Utilisation in CRP-Deficient Strains of *Escherichia coli*," *Mol. Gen. Genet.* 202:257-264 (1986).

Tschopp et al., "Heterologous Gene Expression in Methylotrophic Yeast," *Biotechnol.* 18:305-322 (1991).

Ullah, A.H.J., "*Aspergillus ficuum* Phytase: Partial Primary Structure, Substrate Selectivity, and Kinetic Characterization," *Prep. Biochem.* 18(4):459-471 (1988).

Ullah et al., "Cyclohexanedione Modification of Arginine at the Active Site of *Aspergillus ficuum* Phytase," *Biochem. Biophys. Res. Commun.* 178(1):45-53 (1991).

Ullah et al., "Extracellular Phytase (E.C. 3.1.3.8) from *Aspergillus ficuum* NRRL 3135: Purification and Characterization," *Prep. Biochem.* 17(1):63-91 (1987).

Van Dijck, P.W.M., "Chymosin and Phytase. Made by Genetic Engineering (No. 10 in a Series of Articles to Promote a Better Understanding of the Use of Genetic Engineering)," *J. Biotechnol.* 67:77-80 (1999).

Van Etten et al., "Covalent Structure, Disulfide Bonding, and Identification of Reactive Surface and Active Site Residues of Human Prostatic Acid Phosphatase," *J. Biol. Chem.* 266(4):2313-2319 (1991).

Van Hartingsveldt et al., "Cloning, Characterization and Overexpression of the Phytase-Encoding Gene (*phyA*) of *Aspergillus niger*," *Gene* 127:87-94 (1993).

Verwoerd et al., "Stable Accumulation of *Aspergillus niger* Phytase in Transgenic Tobacco Leaves," *Plant Physiol.* 109:1199-1205(1995).

Wodzinski et al., "Phytase," *Adv. Appl. Microbiol.* 42:263-302 (1996).

Wyss et al., "Biochemical Characterization of Fungal Phytases (*myo*-Inositol Hexakisphosphate Phosphohydrolases): Catalytic Properties," *Appl. Environ. Microbiol.* 65(2):367-373 (1999).

Wyss et al., "Biophysical Characterization of Fungal Phytases (*myo*-Inositol Hexakisphosphate Phosphohydrolases): Molecular Size, Glycosylation Pattern, and Engineering of Proteolytic Resistance," *Appl. Environ. Microbiol.* 65(2):359-366 (1999).

Yao et al., "Recombinant *Pichia pastoris* Overexpressing Bioactive Phytase," *Science in China Series C. Life Sciences* 41(3):330-336 (1998).

Yi et al., "Sites of Phytase Activity in the Gastrointestinal Tract of Young Pigs," *Anim. Feed Sci. Technol.* 61:361-368 (1996).

Zvonok et al., "Construction of Versatile *Escherichia coli*-Yeast Shuttle Vectors for Promoter Testing in *Saccharomyces cerevisiae*," *Gene* 66(2):313-318 (1988).

Ullah et al., "Differences in the Active Site Environment of *Aspergillus ficuum* Phytases," *Biochem. Biophys. Res. Comm.* 243:458-462 (1998).

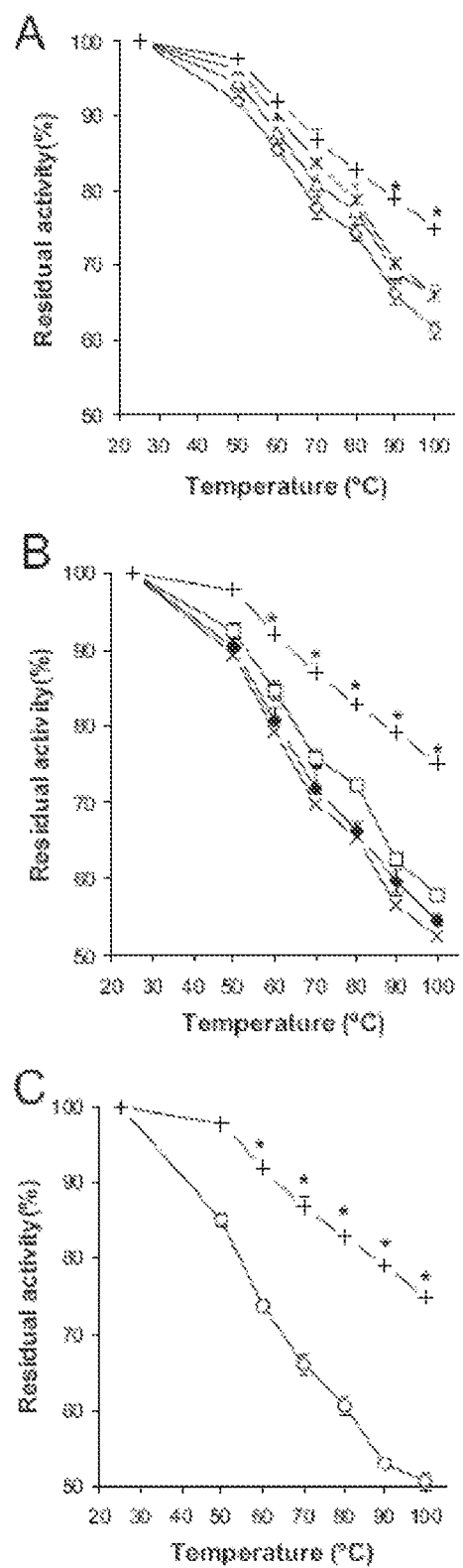
Figures 1A–C

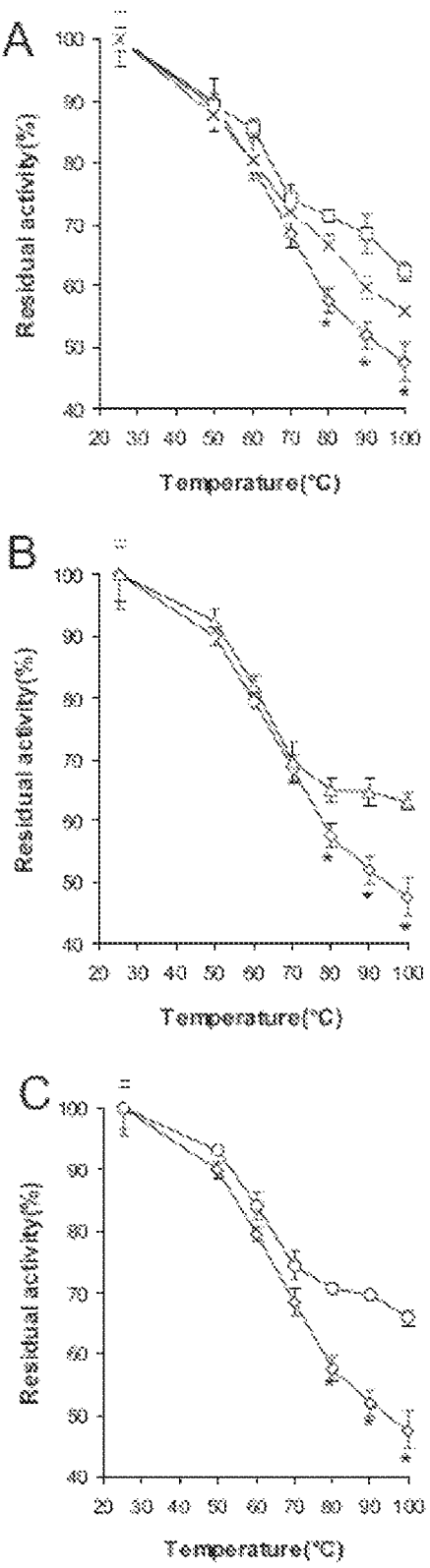
Figures 2A–C

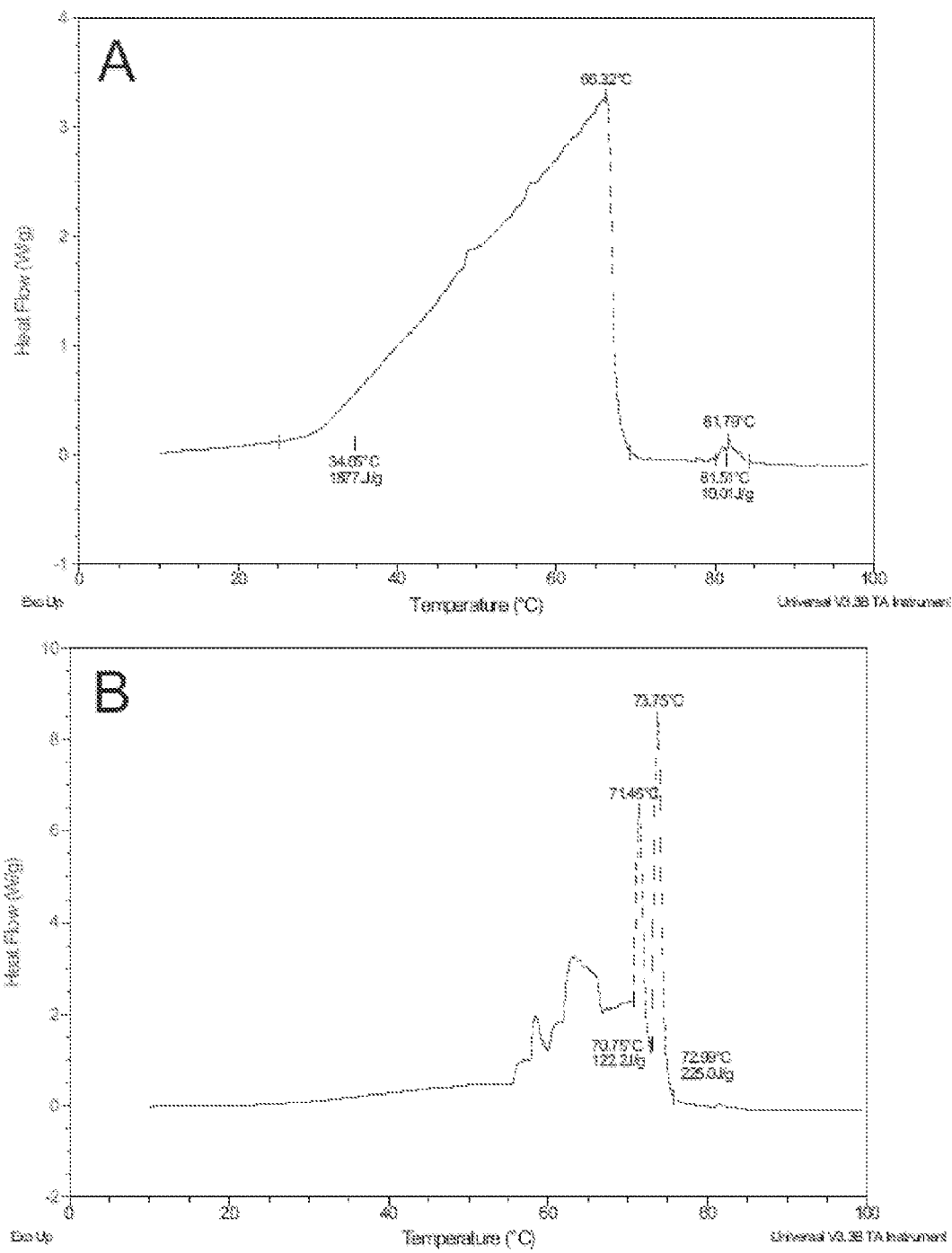
Figures 3A-B

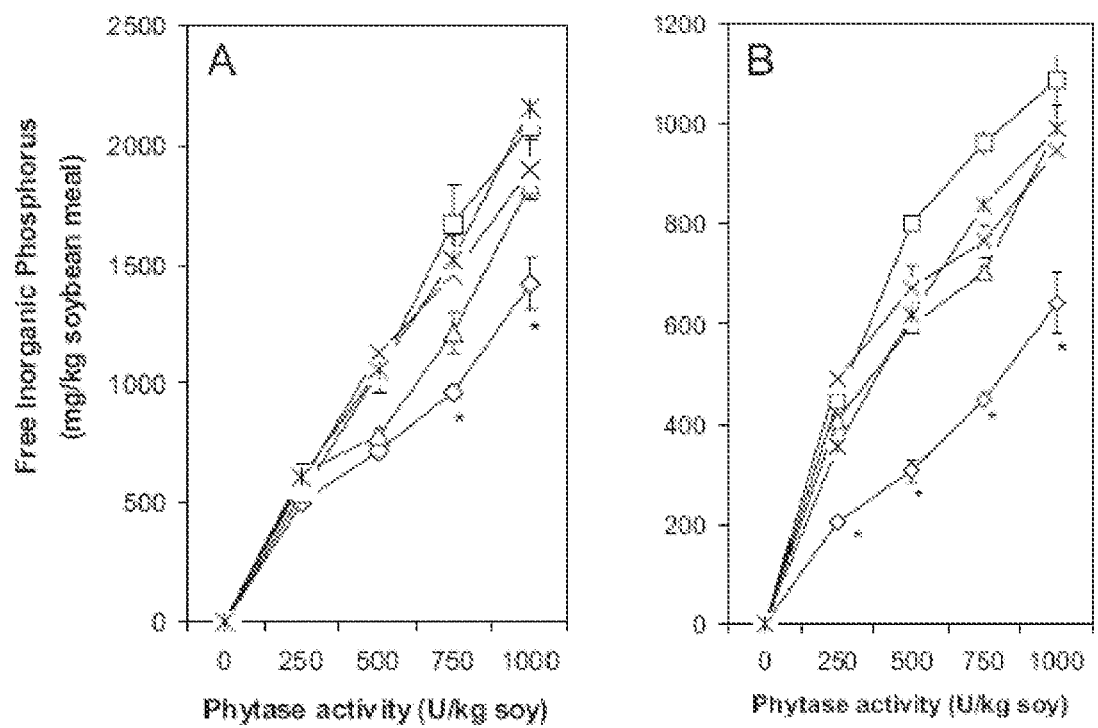
Figures 4A–B

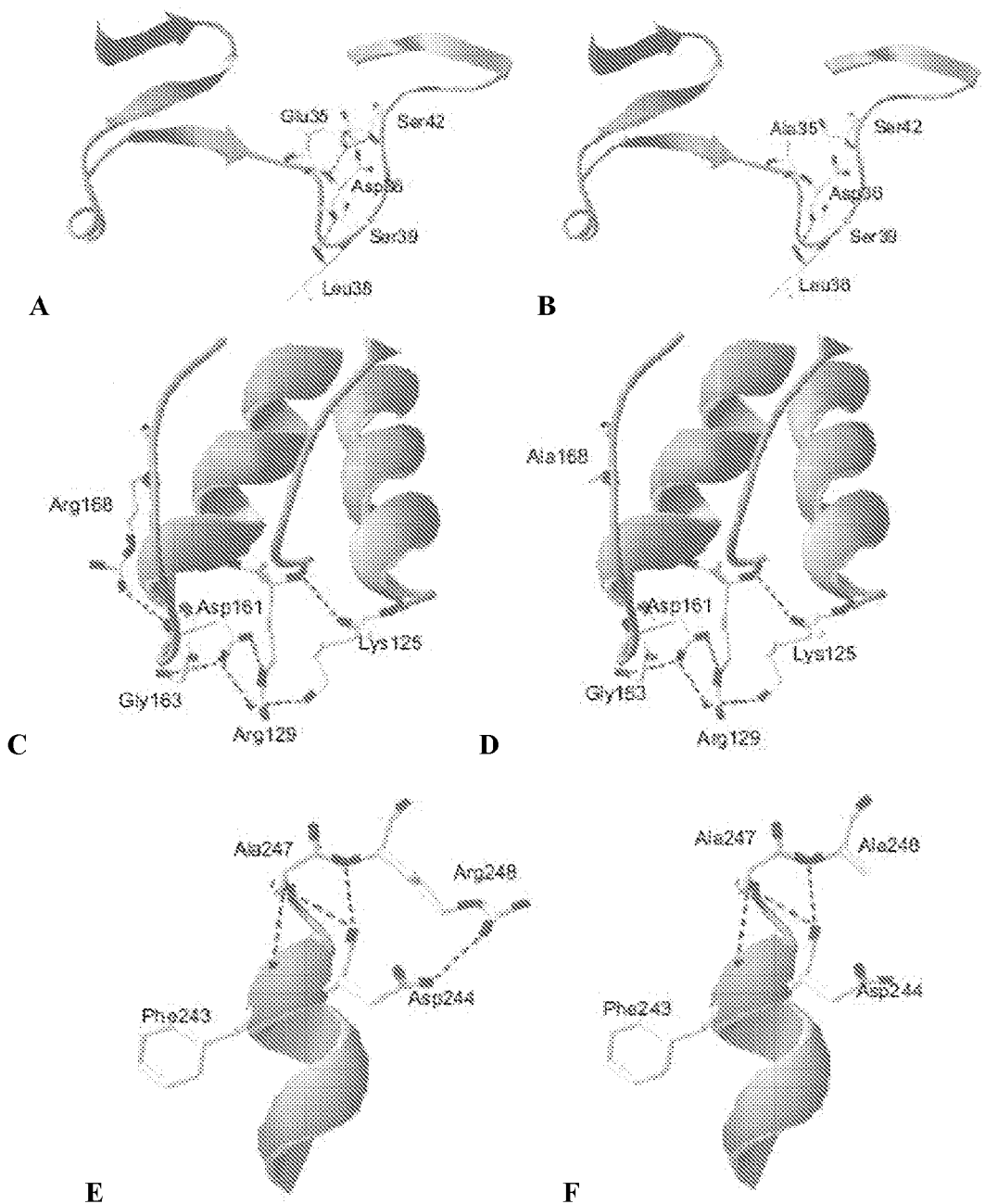
Figures 5A–F

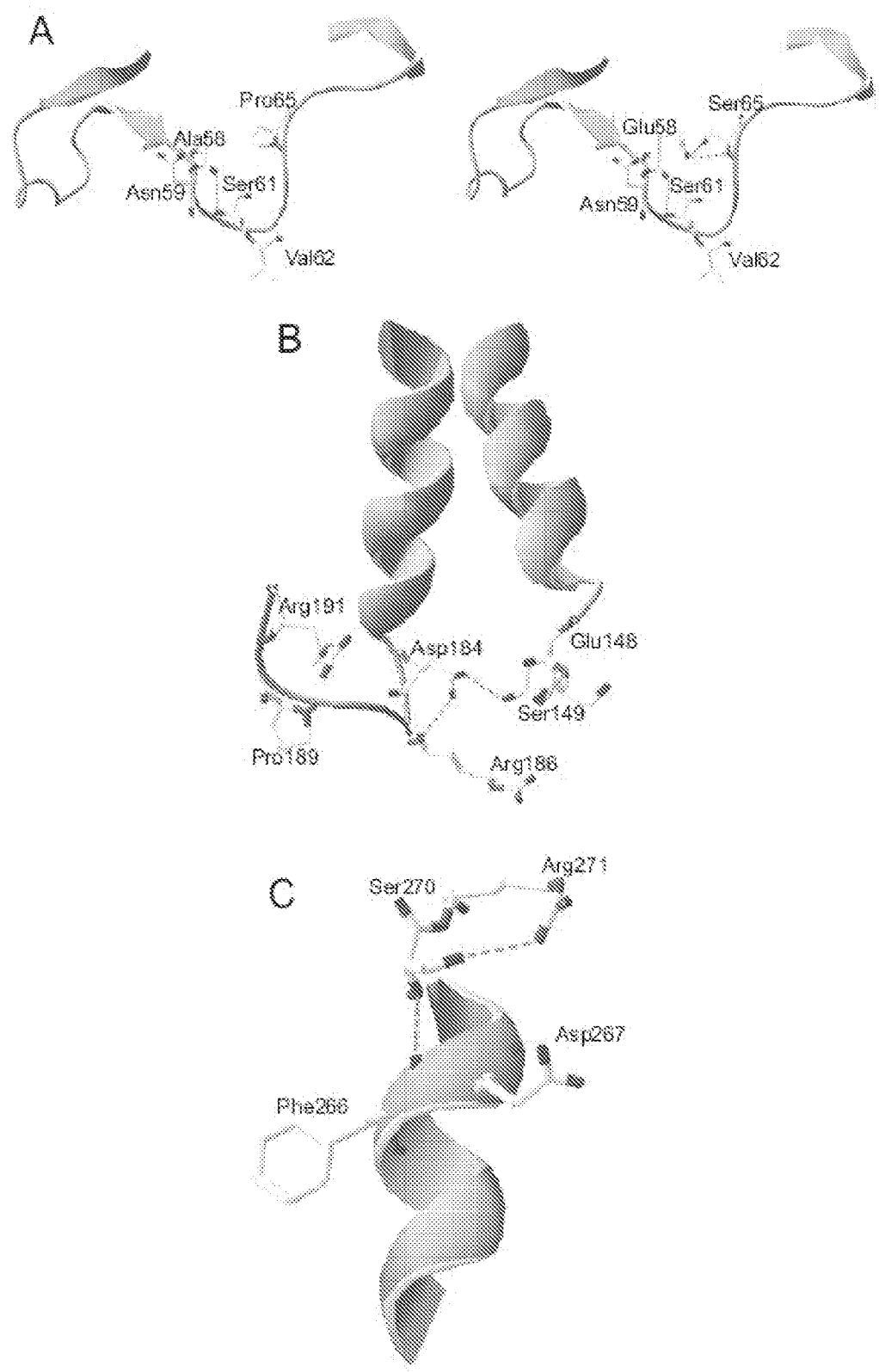
Figures 6A–C

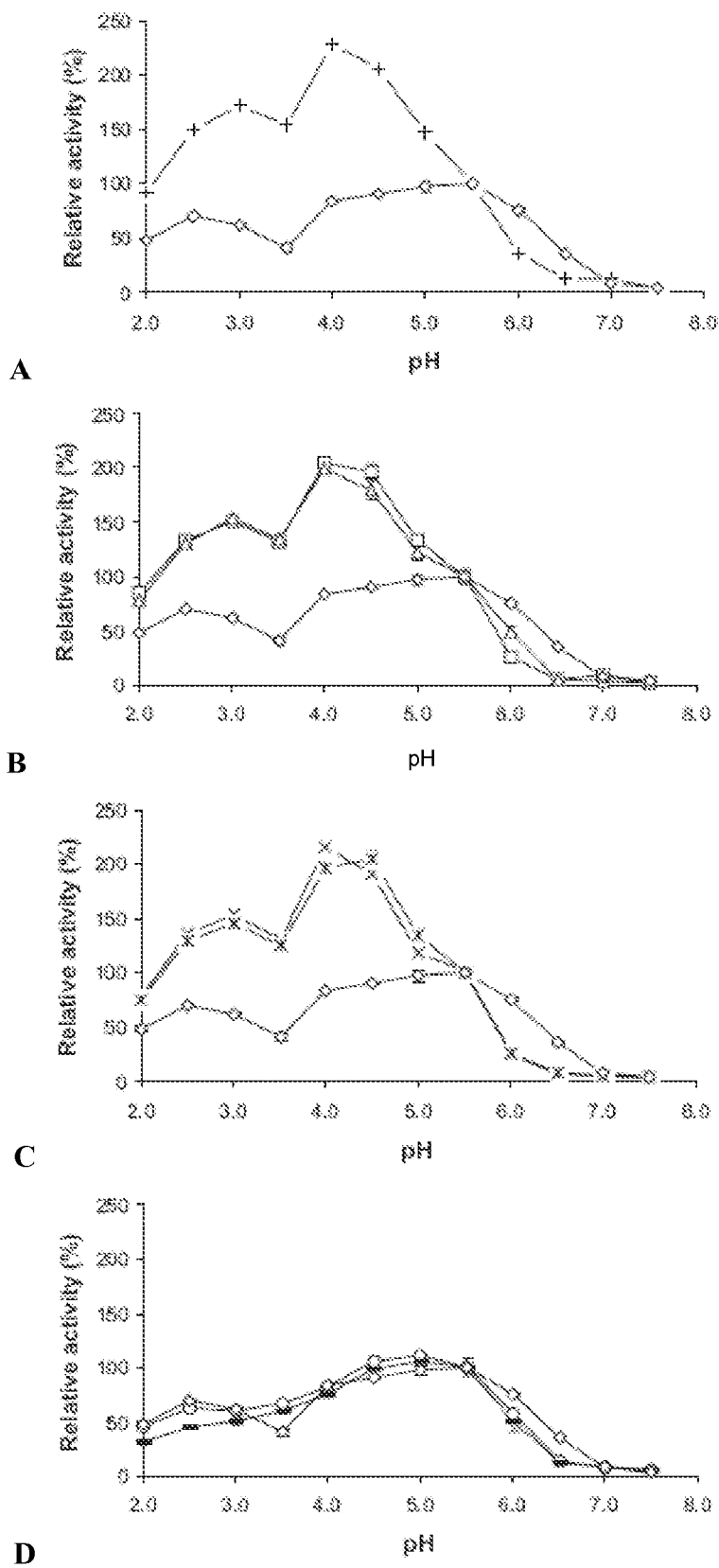
Figures 7A–D

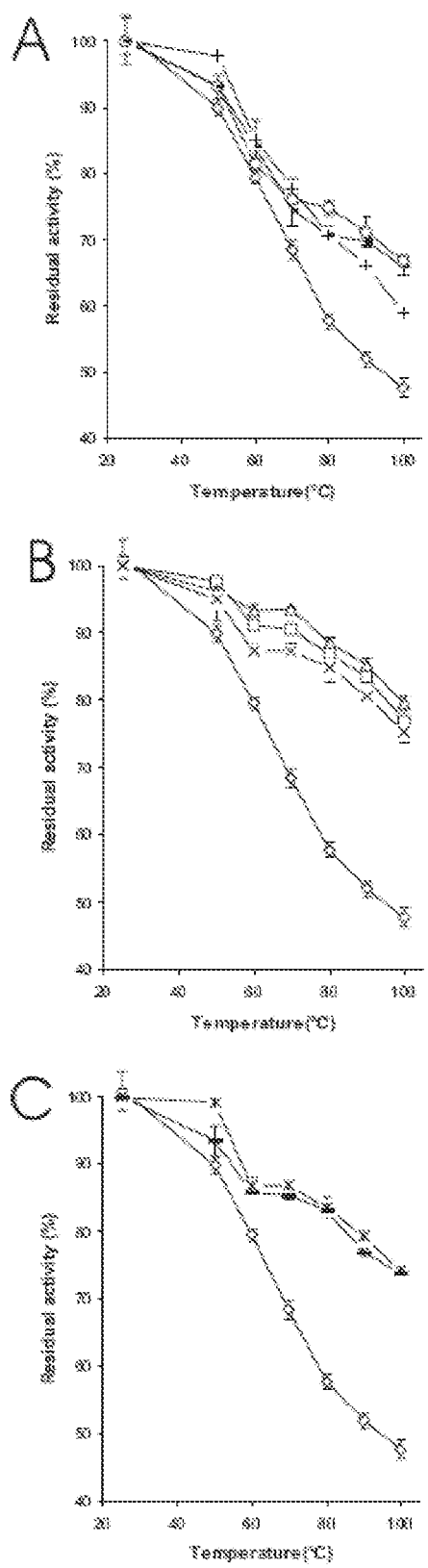
Figures 8A–C

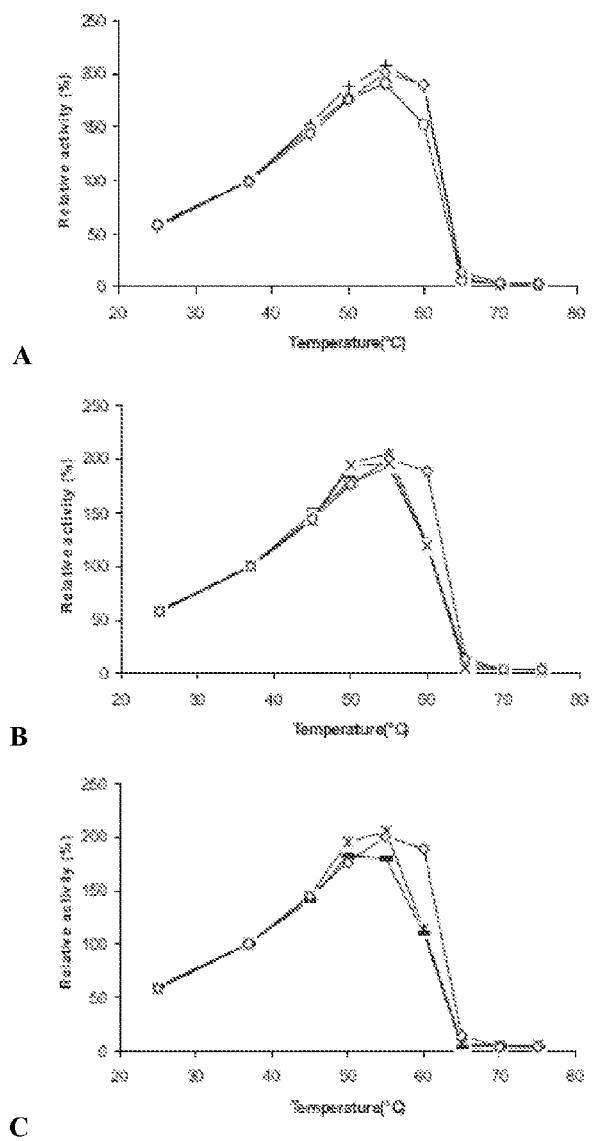
Figures 9A–C
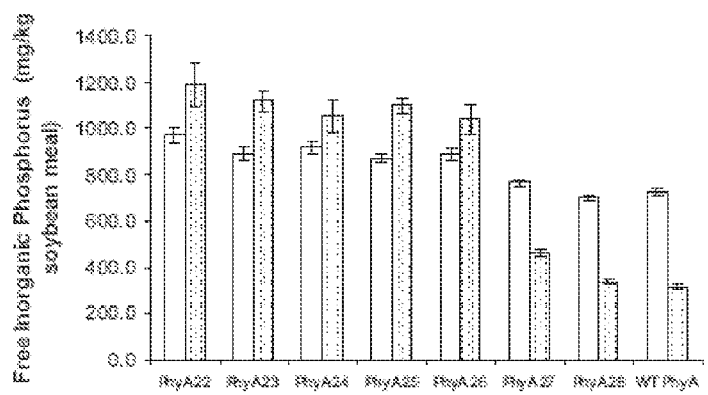
Figure 10

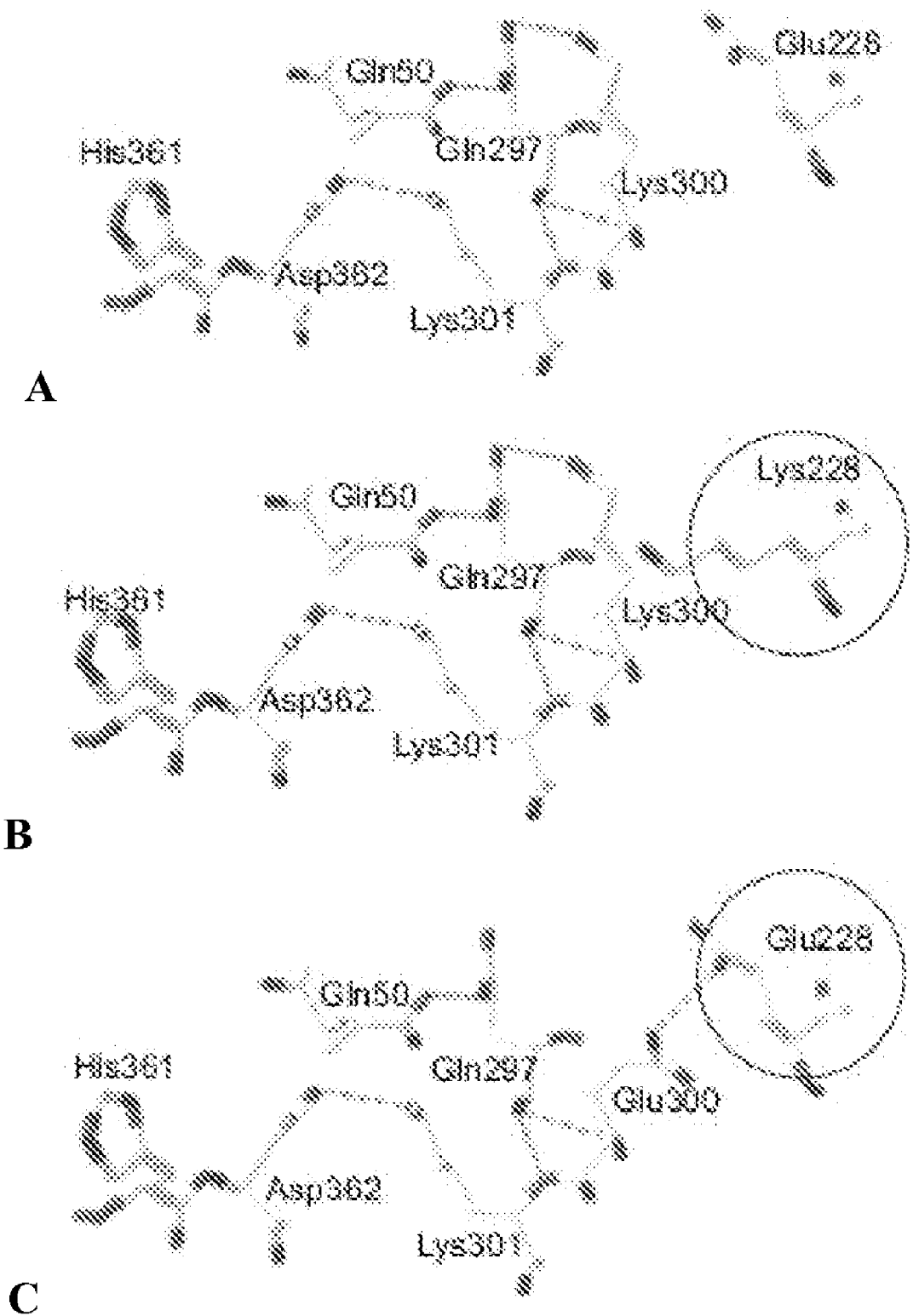
Figures 11A–C

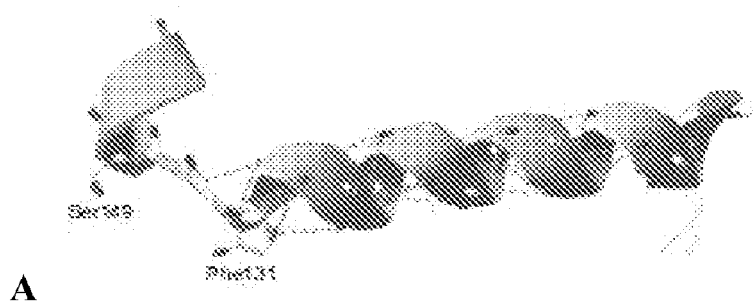
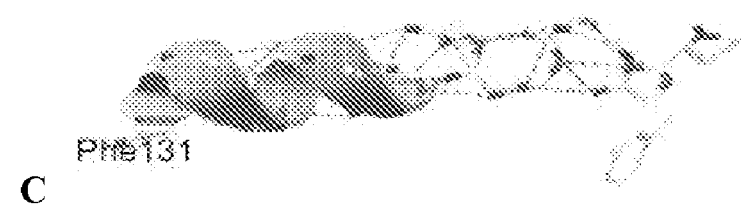
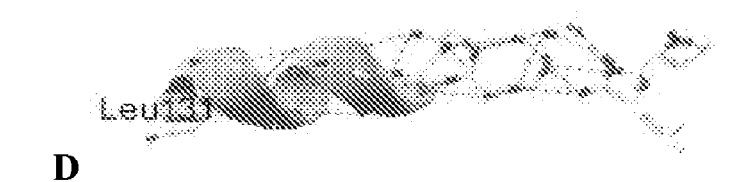
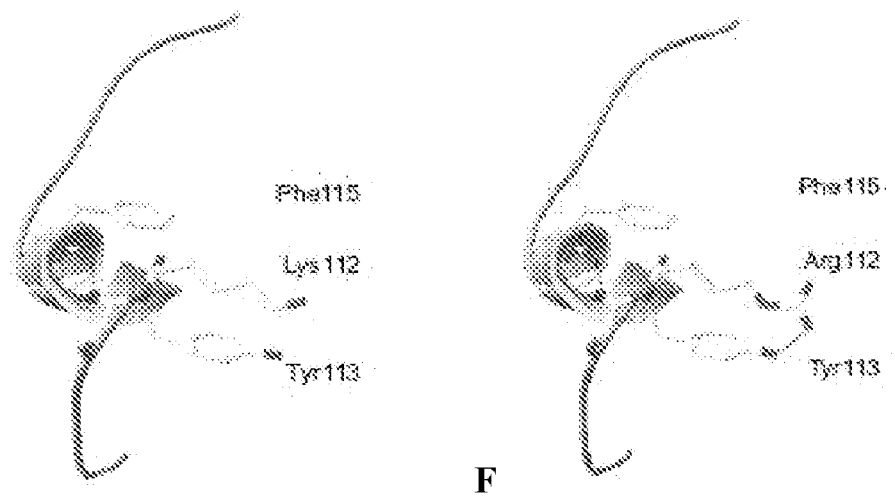
Figures 12A–F

SEQUENCE LISTING

```
<160> NUMBER OF SEQ ID NOS: 27

<210> SEQ ID NO 1
<211> LENGTH: 2665
<212> TYPE: DNA
<213> ORGANISM: Aspergillus niger

<400> SEQUENCE: 1
gcatgcagca ctgtcagcaa ataaattgct ttgaatgatt ttctgcttct tctcatattg      60
ggctatagac actgccgtta tctgactttt aatgagcgag ggcgatgttc atcattcggc     120
gttctgttct tatgatttcc ccacgtcctt tcgggctttc ggcacagcaa aatagattgt     180
ttagcaggta cagaaacaac ttgatgacac atgcatccga gaatcttcag ccgtggaagc     240
attcatgtag atctttgcta agagaaatga tggcggccca gggcatccag gcaccttttc     300
caacggggaa cttccgccgt ccacgtgctc tgattcagcc aatcaagacg tcccacggca     360
atgctggatc aacgatcaac ttgaatgcaa taaatgaaga tggaactaac accatctgct     420
gcctttctct cgagaaagct cctccacttc tcccactaga tatctccgtc cccgtcgact     480
tcccgtccta ttcggcctcg tccgctgaag atccatccca ccattgcacg tgggccacct     540
ttgtgagctt ctaacctgaa ctggtagagt atcacacacc atgccaaggt gggatgaagg     600
ggttatatag gaccgtccgg tccggcgcga tggccgtagc tgccactcgc tgctgtgcaa     660
gaaattactt ctcataggca tcatgggcgt ctctgctgtt ctacttcctt tgtatctcct     720
gtctgggtat gctaagcacc acaatcaaag tctaataagg accctccctt ccgagggccc     780
ctgaagctcg gactgtgtgg gactactgat cgctgactat ctgtgcagag tcacctccgg     840
actggcagtc cccgcctcga gaaatcaatc cagttgcgat acggtcgatc aggggtatca     900
atgcttctcc gagacttcgc atctttgggg tcaatacgca ccgttcttct ctctggcaaa     960
cgaatcggtc atctcccctg aggtgcccgc cggatgcaga gtcactttcg ctcaggtcct    1020
```

```
ctcccgtcat ggagcgcggt atccgaccga ctccaagggc aagaaatact ccgctctcat   1080
tgaggagatc cagcagaacg cgaccacctt tgacggaaaa tatgccttcc tgaagacata   1140
caactacagc ttgggtgcag atgacctgac tcccttcgga gaacaggagc tagtcaactc   1200
cggcatcaag ttctaccagc ggtacgaatc gctcacaagg aacatcgttc cattcatccg   1260
atcctctggc tccagccgcg tgatcgcctc cggcaagaaa ttcatcgagg cttccagag    1320 caccaagctg aaggatcctc gtgcccagcc cggccaatcg tcgcccaaga tcgacgtggt   1380
catttccgag ccagctcat ccaacaacac tctcgaccca ggcacctgca ctgtcttcga    1440
agacagcgaa ttggccgata ccgtcgaagc caatttcacc gccacgttcg tcccctccat   1500
tcgtcaacgt ctggagaacg acctgtccgg tgtgactctc acagacacag aagtgaccta   1560
cctcatggac atgtgctcct tcgacaccat ctccaccagc accgtcgaca ccaagctgtc   1620 cccccttctgt gacctgttca cccatgacga atggatcaac tacgactacc tccagtcctt   1680
gaaaaagtat tacggccatg gtgcaggtaa cccgctcggc cgacccagg gcgtcggcta    1740 cgctaacgag ctcatcgccc gtctgaccca ctcgcctgtc cacgatgaca ccagttccaa   1800
ccacactttg gactcgagcc cggctacctt tccgctcaac tctactctct acgcggactt   1860
ttcgcatgac aacggcatca tctccattct ctttgcttta ggtctgtaca cggcactaa    1920 gccgctatct accacgaccg tggagaatat cacccagaca gatggattct cgtctgcttg   1980
gacggttccg tttgcttcgc gttgtacgt cgagatgatg cagtgtcagg cggagcagga    2040
gccgctggtc cgtgtcttgg ttaatgatcg cgttgtcccg ctgcatgggt gtccggttga   2100
tgctttgggg agatgtaccc gggatagctt tgtgaggggg ttgagctttg ctagatctgg   2160
gggtgattgg gcggagtgtt ttgcttagct gaattacctt gatgaatggt atgtatcagc   2220
attgcatatc attagcactt caggtatgta ttatcgaaga tgtatatcga aaggatcaat   2280
ggtgactgtc actggttatc tgaatatccc tctataccc gcccacaacc aatcatcacc    2340
ctttaaacaa tcacactcaa gccacagcgt acaaacgaac aaacgcacaa agaatatttt   2400
acactcctcc ccaacgcaat accaaccgca attcatcata cctcatataa atacaataca   2460
atacaataca tccatcccta ccctcaagtc cacccatcct ataatcaatc cctacttact   2520
tacttctccc cctcccccctc acccttccca gaactcaccc ccgaagtagt aatagtagta   2580
gtagaagaag cagacgacct ctccaccaat ctcttcggcc tcttatcccc atacgctaca   2640
caaaaccccc accccgttag catgc                                         2665
```

<210> SEQ ID NO 2
<211> LENGTH: 467
<212> TYPE: PRT
<213> ORGANISM: Aspergillus niger

<400> SEQUENCE: 2

Met Gly Val Ser Ala Val Leu Leu Pro Leu Tyr Leu Leu Ser Gly Val
1               5                   10                  15

Thr Ser Gly Leu Ala Val Pro Ala Ser Arg Asn Gln Ser Ser Cys Asp
            20                  25                  30

Thr Val Asp Gln Gly Tyr Gln Cys Phe Ser Glu Thr Ser His Leu Trp
        35                  40                  45

Gly Gln Tyr Ala Pro Phe Phe Ser Leu Ala Asn Glu Ser Val Ile Ser
    50                  55                  60

Pro Glu Val Pro Ala Gly Cys Arg Val Thr Phe Ala Gln Val Leu Ser
65                  70                  75                  80

```
Arg His Gly Ala Arg Tyr Pro Thr Asp Ser Lys Gly Lys Lys Tyr Ser
             85                  90                  95

Ala Leu Ile Glu Glu Ile Gln Gln Asn Ala Thr Thr Phe Asp Gly Lys
        100                 105                 110

Tyr Ala Phe Leu Lys Thr Tyr Asn Tyr Ser Leu Gly Ala Asp Asp Leu
            115                 120                 125

Thr Pro Phe Gly Glu Gln Glu Leu Val Asn Ser Gly Ile Lys Phe Tyr
        130                 135                 140

Gln Arg Tyr Glu Ser Leu Thr Arg Asn Ile Val Pro Phe Ile Arg Ser
145                 150                 155                 160

Ser Gly Ser Ser Arg Val Ile Ala Ser Gly Lys Lys Phe Ile Glu Gly
                165                 170                 175

Phe Gln Ser Thr Lys Leu Lys Asp Pro Arg Ala Gln Pro Gly Gln Ser
            180                 185                 190

Ser Pro Lys Ile Asp Val Val Ile Ser Glu Ala Ser Ser Ser Asn Asn
        195                 200                 205

Thr Leu Asp Pro Gly Thr Cys Thr Val Phe Glu Asp Ser Glu Leu Ala
        210                 215                 220

Asp Thr Val Glu Ala Asn Phe Thr Ala Thr Phe Val Pro Ser Ile Arg
225                 230                 235                 240

Gln Arg Leu Glu Asn Asp Leu Ser Gly Val Thr Leu Thr Asp Thr Glu
            245                 250                 255

Val Thr Tyr Leu Met Asp Met Cys Ser Phe Asp Thr Ile Ser Thr Ser
            260                 265                 270

Thr Val Asp Thr Lys Leu Ser Pro Phe Cys Asp Leu Phe Thr His Asp
        275                 280                 285

Glu Trp Ile Asn Tyr Asp Tyr Leu Gln Ser Leu Lys Lys Tyr Tyr Gly
        290                 295                 300

His Gly Ala Gly Asn Pro Leu Gly Pro Thr Gln Gly Val Gly Tyr Ala
305                 310                 315                 320

Asn Glu Leu Ile Ala Arg Leu Thr His Ser Pro Val His Asp Asp Thr
            325                 330                 335

Ser Ser Asn His Thr Leu Asp Ser Ser Pro Ala Thr Phe Pro Leu Asn
        340                 345                 350

Ser Thr Leu Tyr Ala Asp Phe Ser His Asp Asn Gly Ile Ile Ser Ile
        355                 360                 365

Leu Phe Ala Leu Gly Leu Tyr Asn Gly Thr Lys Pro Leu Ser Thr Thr
        370                 375                 380

Thr Val Glu Asn Ile Thr Gln Thr Asp Gly Phe Ser Ser Ala Trp Thr
385                 390                 395                 400

Val Pro Phe Ala Ser Arg Leu Tyr Val Glu Met Met Gln Cys Gln Ala
            405                 410                 415

Glu Gln Glu Pro Leu Val Arg Val Leu Val Asn Asp Arg Val Val Pro
        420                 425                 430

Leu His Gly Cys Pro Val Asp Ala Leu Gly Arg Cys Thr Arg Asp Ser
        435                 440                 445

Phe Val Arg Gly Leu Ser Phe Ala Arg Ser Gly Gly Asp Trp Ala Glu
        450                 455                 460

Cys Phe Ala
465

<210> SEQ ID NO 3
<211> LENGTH: 1812
<212> TYPE: DNA
<213> ORGANISM: Aspergillus fumigatus
```

```
<400> SEQUENCE: 3
ggaaacccat cccctgctct cacgcgacag agtcacgaat cgctccaccg acgataggct      60
actcgtcctg taaaccagct gattgtctac cggtgtggtg cgacgggtaa gctgggctcc     120
actaggctca gaccccccgt tcgtatgcg aaggggagt gcgatgtgag tcgggcggga       180
agagatggaa aagctatata atggccggcg tgtccggcga ggggaggatg gtttcccgat     240
cagattcaac gacggaggaa tcgcaaccct aattgtcggt atcatggtga ctctgacttt     300
cctgctttcg gcggcgtatc tgctttctgg gtgagtggct tggatctatt gctcggatag    360
ggctgtggtg ctgattctga aacggagtag agtgtctgcg gcacctagtt ctgctggctc    420
caagtcctgc gatacggtag acctcgggta ccagtgctcc cctgcgactt ctcatctatg    480
gggccagtac tcgccattct tttcgctcga ggacgagctg tccgtgtcga gtaagcttcc    540
caaggattgc cggatcacct tggtacaggt gctatcgcgc catggagcgc ggtacccaac    600
cagctccaag agcaaaaagt ataagaagct tgtgacggcg atccaggcca atgccaccga    660
cttcaagggc aagtttgcct ttttgaagac gtacaactat actctgggtg cggatgacct    720
cactcccttt ggggagcagc agctggtgaa ctcgggcatc aagttctacc agaggtacaa    780
ggctctggcg cgcagtgtgg tgccgtttat tcgcgcctca ggctcggacc gggttattgc    840
ttcgggagag aagttcatcg aggggttcca gcaggcgaag ctggctgatc ctggcgcgac    900
gaaccgcgcc gctccggcga ttagtgtgat tattccggag agcgagacgt caacaatac    960 gctgaccac ggtgtgtgca cgaagtttga ggcgagtcag ctgggagatg aggttgcggc   1020
caatttcact gcgctctttg cacccgacat ccgagctcgc gccgagaagc atcttcctgg    1080
cgtgacgctg acagacgagg acgttgtcag tctaatggac atgtgttcgt ttgatacggt    1140
agcgcgcacc agcgacgcaa gtcagctgtc accgttctgt caactcttca ctcacaatga    1200
gtggaagaag tacaactacc ttcagtcctt gggcaagtac tacggctacg cgcaggcaa    1260 ccctctggga ccggctcagg ggatagggtt caccaacgag ctgattgccc ggttgactcg    1320
ttcgccagtg caggaccaca ccagcactaa ctcgactcta gtctccaacc cggccacctt    1380
cccgttgaac gctaccatgt acgtcgactt ttcacacgac aacagcatgg tttccatctt    1440
ctttgcattg ggcctgtaca acggcactga acccttgtcc cggacctcgg tggaaagcgc    1500
caaggaattg gatgggtatt ctgcatcctg ggtggtgcct ttcggcgcgc gagcctactt    1560
cgagacgatg caatgcaagt cggaaaagga gcctcttgtt cgcgctttga ttaatgaccg    1620
ggttgtgcca ctgcatggct gcgatgtgga caagctgggg cgatgcaagc tgaatgactt    1680
tgtcaaggga ttgagttggg ccagatctgg gggcaactgg ggagagtgct ttagttgaga    1740
tgtcattgtt atgctatact ccaatagacc gttgcttagc cattcacttc actttgctcg    1800
aaccgcctgc cg                                                        1812

<210> SEQ ID NO 4
<211> LENGTH: 444
<212> TYPE: PRT
<213> ORGANISM: Aspergillus fumigatus
<220> FEATURE:
<221> NAME/KEY: MISC_FEATURE
<222> LOCATION: (165)..(165)
<223> OTHER INFORMATION: Xaa at position 165 is absent

<400> SEQUENCE: 4

Glu Ala Glu Phe Ser Lys Ser Cys Asp Thr Val Asp Leu Gly Tyr Gln
 1               5                  10                  15
```

-continued

```
Cys Ser Pro Ala Thr Ser His Leu Trp Gly Gln Tyr Ser Pro Phe Phe
         20                  25                  30

Ser Leu Glu Asp Glu Leu Ser Val Ser Ser Lys Leu Pro Lys Asp Cys
         35                  40                  45

Arg Ile Thr Leu Val Gln Val Leu Ser Arg His Gly Ala Arg Tyr Pro
         50                  55                  60

Thr Ser Ser Lys Ser Lys Lys Tyr Lys Lys Leu Val Thr Ala Ile Gln
65                   70                  75                  80

Ala Asn Ala Thr Asp Phe Lys Gly Lys Phe Ala Phe Leu Lys Thr Tyr
                     85                  90                  95

Asn Tyr Thr Leu Gly Ala Asp Asp Leu Thr Pro Phe Gly Glu Gln Gln
                 100                 105                 110

Leu Val Asn Ser Gly Ile Lys Phe Tyr Gln Arg Tyr Lys Ala Leu Ala
                 115                 120                 125

Arg Ser Val Val Pro Phe Ile Arg Ala Ser Gly Ser Asp Arg Val Ile
         130                 135                 140

Ala Ser Gly Glu Lys Phe Ile Glu Gly Phe Gln Gln Ala Lys Leu Ala
145                 150                 155                 160

Asp Pro Gly Ala Xaa Thr Asn Arg Ala Ala Pro Ala Ile Ser Val Ile
                     165                 170                 175

Ile Pro Glu Ser Glu Thr Phe Asn Asn Thr Leu Asp His Gly Val Cys
                 180                 185                 190

Thr Lys Phe Glu Ala Ser Gln Leu Gly Asp Glu Val Ala Ala Asn Phe
                 195                 200                 205

Thr Ala Leu Phe Ala Pro Asp Ile Arg Ala Arg Ala Glu Lys His Leu
         210                 215                 220

Pro Gly Val Thr Leu Thr Asp Glu Asp Val Val Ser Leu Met Asp Met
225                 230                 235                 240

Cys Ser Phe Asp Thr Val Ala Arg Thr Ser Asp Ala Ser Gln Leu Ser
                     245                 250                 255

Pro Phe Cys Gln Leu Phe Thr His Asn Glu Trp Lys Lys Tyr Asn Tyr
                 260                 265                 270

Leu Gln Ser Leu Gly Lys Tyr Tyr Gly Tyr Gly Ala Gly Asn Pro Leu
                 275                 280                 285

Gly Pro Ala Gln Gly Ile Gly Phe Thr Asn Glu Leu Ile Ala Arg Leu
         290                 295                 300

Thr Arg Ser Pro Val Gln Asp His Thr Ser Thr Asn Ser Thr Leu Val
305                 310                 315                 320

Ser Asn Pro Ala Thr Phe Pro Leu Asn Ala Thr Met Tyr Val Asp Phe
                     325                 330                 335

Ser His Asp Asn Ser Met Val Ser Ile Phe Phe Ala Leu Gly Leu Tyr
                 340                 345                 350

Asn Gly Thr Glu Pro Leu Ser Arg Thr Ser Val Glu Ser Ala Lys Glu
                 355                 360                 365

Leu Asp Gly Tyr Ser Ala Ser Trp Val Val Pro Phe Gly Ala Arg Ala
         370                 375                 380

Tyr Phe Glu Thr Met Gln Cys Lys Ser Glu Lys Glu Pro Leu Val Arg
385                 390                 395                 400

Ala Leu Ile Asn Asp Arg Val Val Pro Leu His Gly Cys Asp Val Asp
                     405                 410                 415

Lys Leu Gly Arg Cys Lys Leu Asn Asp Phe Val Lys Gly Leu Ser Trp
                 420                 425                 430

Ala Arg Ser Gly Gly Asn Trp Gly Glu Cys Phe Ser
         435                 440
```

<210> SEQ ID NO 5
<211> LENGTH: 22
<212> TYPE: DNA
<213> ORGANISM: artificial
<220> FEATURE:
<223> OTHER INFORMATION: Oligonucleotide primer afp-F2

<400> SEQUENCE: 5
ggatttcgat gttgctgttt tg                                             22

<210> SEQ ID NO 6
<211> LENGTH: 22
<212> TYPE: DNA
<213> ORGANISM: artificial
<220> FEATURE:
<223> OTHER INFORMATION: Oligonucleotide primer afp-M1(E35A)

<400> SEQUENCE: 6
cagctcgtcc gcgagcgaaa ag                                             22

<210> SEQ ID NO 7
<211> LENGTH: 21
<212> TYPE: DNA
<213> ORGANISM: artificial
<220> FEATURE:
<223> OTHER INFORMATION: Oligonucleotide primer afp-M2(R168A)

<400> SEQUENCE: 7
gcgacgaacg ccgccgctcc g                                              21

<210> SEQ ID NO 8
<211> LENGTH: 21
<212> TYPE: DNA
<213> ORGANISM: artificial
<220> FEATURE:
<223> OTHER INFORMATION: Oligonucleotide primer afp-M3(R248A)

<400> SEQUENCE: 8
acggtagcgg ccaccagcga c                                              21

<210> SEQ ID NO 9
<211> LENGTH: 22
<212> TYPE: DNA
<213> ORGANISM: artificial
<220> FEATURE:
<223> OTHER INFORMATION: Oligonucleotide primer afp-R2

<400> SEQUENCE: 9
gtcgagttag tgctggtgtg gt                                             22

<210> SEQ ID NO 10
<211> LENGTH: 24
<212> TYPE: DNA
<213> ORGANISM: artificial
<220> FEATURE:
<223> OTHER INFORMATION: Oligonucleotide primer phyA-F

<400> SEQUENCE: 10
cggaattcct ggcagtcccc gcct                                           24

<210> SEQ ID NO 11
<211> LENGTH: 25
<212> TYPE: DNA
<213> ORGANISM: artificial
<220> FEATURE:
<223> OTHER INFORMATION: Oligonucleotide primer phyA-A58E

```
<400> SEQUENCE: 11
accgattcgt tttccagaga gaaga                                    25

<210> SEQ ID NO 12
<211> LENGTH: 24
<212> TYPE: DNA
<213> ORGANISM: artificial
<220> FEATURE:
<223> OTHER INFORMATION: Oligonucleotide primer phyA-P65S

<400> SEQUENCE: 12
gcgggcacct cagaggagat gacc                                     24

<210> SEQ ID NO 13
<211> LENGTH: 25
<212> TYPE: DNA
<213> ORGANISM: artificial
<220> FEATURE:
<223> OTHER INFORMATION: Oligonucleotide primer phyA-Q191R

<400> SEQUENCE: 13
ttgggcgacg atcggccggg ctggg                                    25

<210> SEQ ID NO 14
<211> LENGTH: 25
<212> TYPE: DNA
<213> ORGANISM: artificial
<220> FEATURE:
<223> OTHER INFORMATION: Oligonucleotide primer phyA-T271R

<400> SEQUENCE: 14
acaccatctc cagaagcacc gtcga                                    25

<210> SEQ ID NO 15
<211> LENGTH: 24
<212> TYPE: DNA
<213> ORGANISM: artificial
<220> FEATURE:
<223> OTHER INFORMATION: Oligonucleotide primer phyA-R

<400> SEQUENCE: 15
gctctagact aagcaaaaca ctcc                                     24

<210> SEQ ID NO 16
<211> LENGTH: 25
<212> TYPE: DNA
<213> ORGANISM: artificial
<220> FEATURE:
<223> OTHER INFORMATION: Oligonucleotide primer K112R-F

<400> SEQUENCE: 16
cctttgacgg aagatatgcc ttcct                                    25

<210> SEQ ID NO 17
<211> LENGTH: 25
<212> TYPE: DNA
<213> ORGANISM: artificial
<220> FEATURE:
<223> OTHER INFORMATION: Oligonucleotide primer K112R-R

<400> SEQUENCE: 17
aggaaggcat atcttccgtc aaagg                                    25

<210> SEQ ID NO 18
<211> LENGTH: 25
```

```
<212> TYPE: DNA
<213> ORGANISM: artificial
<220> FEATURE:
<223> OTHER INFORMATION: Oligonucleotide primer F131L-F

<400> SEQUENCE: 18
acctgactcc cctcggagaa cagga                                  25

<210> SEQ ID NO 19
<211> LENGTH: 25
<212> TYPE: DNA
<213> ORGANISM: artificial
<220> FEATURE:
<223> OTHER INFORMATION: Oligonucleotide primer F131L-R

<400> SEQUENCE: 19
tcctgttctc cgaggggagt caggt                                  25

<210> SEQ ID NO 20
<211> LENGTH: 25
<212> TYPE: DNA
<213> ORGANISM: artificial
<220> FEATURE:
<223> OTHER INFORMATION: Oligonucleotide primer S149P-F

<400> SEQUENCE: 20
agcggtacga accgctcaca aggaa                                  25

<210> SEQ ID NO 21
<211> LENGTH: 25
<212> TYPE: DNA
<213> ORGANISM: artificial
<220> FEATURE:
<223> OTHER INFORMATION: Oligonucleotide primer S149P-R

<400> SEQUENCE: 21
ttccttgtga gcggttcgta ccgct                                  25

<210> SEQ ID NO 22
<211> LENGTH: 25
<212> TYPE: DNA
<213> ORGANISM: artificial
<220> FEATURE:
<223> OTHER INFORMATION: Oligonucleotide primer K195R-F

<400> SEQUENCE: 22
gatcgtcgcc caggatcgac gtggt                                  25

<210> SEQ ID NO 23
<211> LENGTH: 25
<212> TYPE: DNA
<213> ORGANISM: artificial
<220> FEATURE:
<223> OTHER INFORMATION: Oligonucleotide primer K195R-R

<400> SEQUENCE: 23
accacgtcga tcctgggcga cgatc                                  25

<210> SEQ ID NO 24
<211> LENGTH: 25
<212> TYPE: DNA
<213> ORGANISM: artificial
<220> FEATURE:
<223> OTHER INFORMATION: Oligonucleotide primer E228K-F

<400> SEQUENCE: 24
ccgataccgt caaagccaat ttcac                                  25
```

```
<210> SEQ ID NO 25
<211> LENGTH: 25
<212> TYPE: DNA
<213> ORGANISM: artificial
<220> FEATURE:
<223> OTHER INFORMATION: Oligonucleotide primer E228K-R

<400> SEQUENCE: 25
gtgaaattgg ctttgacggt atcgg                                          25

<210> SEQ ID NO 26
<211> LENGTH: 25
<212> TYPE: DNA
<213> ORGANISM: artificial
<220> FEATURE:
<223> OTHER INFORMATION: Oligonucleotide primer K300E-F

<400> SEQUENCE: 26
tccagtcctt ggaaaagtat tacgg                                          25

<210> SEQ ID NO 27
<211> LENGTH: 25
<212> TYPE: DNA
<213> ORGANISM: artificial
<220> FEATURE:
<223> OTHER INFORMATION: Oligonucleotide primer K300E-R

<400> SEQUENCE: 27
ccgtaatact tttccaagga ctgga                                          25
```

US 7,919,297 B2

MUTANTS OF ASPERGILLUS NIGER PHYA PHYTASE AND ASPERGILLUS FUMIGATUS PHYTASE

This application claims the benefit of U.S. Provisional Patent Application Ser. No. 60/775,258, filed Feb. 21, 2006, which is hereby incorporated by reference in its entirety.

FIELD OF THE INVENTION

This invention is directed generally to using mutations to improve phytases of *Aspergillus niger* PhyA phytase and *Aspergillus fumigatus* Afp phytase.

BACKGROUND OF THE INVENTION

Phytases catalyze the hydrolysis of phytate (myo-inositol hexakisphostate), a major storage form of phosphorus in plant seeds (Reddy et al., "Phytates in Legumes and Cereals," *Adv. Food Res.* 28:1-92 (1982)), to phosphate and myo-inositol, and render phytate-phosphorus bio-available to animals. Therefore, phytases have been used as an animal feed supplement to improve the bioavailability of phytate phosphorus and other minerals to simple-stomached animals, such as swine and poultry (Gentile et al., "Effectiveness of an Experimental Consensus Phytase in Improving Dietary Phytate-phosphorus Utilization by Weanling Pigs," *J. Anim. Sci.* 81:2751-7 (2003); Lei et al., "Supplemental Microbial Phytase Improves Bioavailability of Dietary Zinc to Weanling Pigs," *J. Nutr.* 123:1117-23 (1993); Casey & Walsh, "Identification and Characterization of a Phytase of Potential Commercial Interest," *J. Biotechnol.* 110:313-22 (2004); Lei & Porres, "Phytase Enzymology, Applications, and Biotechnology," *Biotechnol. Lett.* 25:1787-94 (2003)). However, none of the natural phytases, including the commercially available phytases, can meet the requirements for industrial use (Lei & Stahl, "Biotechnological Development of Effective Phytases for Mineral Nutrition and Environmental Protection," *Appl. Microbiol. Biotechnol.* 57:474-81 (2001)). The temperature during the processing of feed pelleting can reach as high as 70-90° C. (Mullaney et al., "Advances in Phytase Research," *Adv. Appl. Microbiol.* 47:157-99 (2000)). Phytases with sufficiently high thermal stability to withstand these higher temperatures are desirable, but rare among the naturally-occurring sources of phytase (Lei & Stahl, "Biotechnological Development of Effective Phytases for Mineral Nutrition and Environmental Protection," *Appl. Microbiol. Biotechnol.* 57:474-81 (2001)). As an ideal phytase will need to function well in the digestive tract of animals, the enzyme should also be effective at a pH ranging from 2.5 to 3.5 (Konietzny & Greiner, "Molecular and Catalytic Properties of Phytate-degrading Enzymes (Phytases)," *Int. J. Food Sci. Tech.* 37(7):791-812 (2002)).

Thus, there remains a need for improved phytases with greater thermostability and pH profile. The present invention is directed to overcoming these and other deficiencies in the art.

SUMMARY OF THE INVENTION

One aspect of the present invention relates to an isolated nucleic acid molecule encoding a protein or polypeptide having phytase activity. The protein or polypeptide includes an amino acid sequence having at least 90 percent sequence identity to SEQ ID NO: 2 over a region of at least 100 amino acid residues and containing at least one substitution of at least one amino acid residue selected from the group consisting of residues A58, P65, K112, F131, S149, Q191, K195, and T271 of SEQ ID NO: 2.

A second aspect of the present invention relates to an isolated nucleic acid molecule encoding a protein or polypeptide having phytase activity. The protein or polypeptide includes an amino acid sequence having at least 90 percent sequence identity to SEQ ID NO: 4 over a region of at least 100 amino acid residues and containing at least one substitution of at least one amino acid residue selected from the group consisting of residues A205 and G277 of SEQ ID NO: 4.

A third aspect of the present invention relates to an isolated protein or polypeptide having phytase activity. The protein or polypeptide includes an amino acid sequence having at least 90 percent sequence identity to SEQ ID NO: 2 over a region of at least 100 amino acid residues and containing at least one substitution of at least one amino acid residue selected from the group consisting of residue A58, P65, K112, F131, S149, Q191, K195, and T271 of SEQ ID NO: 2.

A fourth aspect of the present invention relates to an isolated protein or polypeptide having phytase activity. The protein or polypeptide includes an amino acid sequence having at least 90 percent sequence identity to SEQ ID NO: 4 over a region of at least 100 amino acid residues and containing at least one substitution of at least one amino acid residue selected from the group consisting of residues A205 and G277 of SEQ ID NO: 4.

A fifth aspect of the present invention relates to a method of improving the nutritional value of a foodstuff consumed by an animal. This method involves providing a foodstuff comprising myo-inositol hexakisphosphate, providing an isolated protein or polypeptide according to the present invention, and feeding to the animal the foodstuff in combination with the protein or polypeptide under conditions effective to increase the bioavailability of phosphate from phytate.

A sixth aspect of the present invention relates to a method for producing an improved phytase protein or polypeptide. This method involves providing a nucleic acid sequence encoding a phytase protein or polypeptide having an amino acid sequence of at least 90 percent sequence identity to SEQ ID NO: 2, and altering the nucleic acid sequence under conditions effective to yield a nucleic acid sequence encoding an improved phytase protein or polypeptide. The improved phytase protein or polypeptide includes an amino acid sequence having at least 90 percent sequence identity to SEQ ID NO: 2 over a region of at least 100 amino acid residues and containing at least one substitution of at least one amino acid residue selected from the group consisting of residues A58, P65, K112, F131, S149, Q191, K195, and T271 of SEQ ID NO: 2, and has a higher heat tolerance and/or better pH profile compared with the heat tolerance and/or pH profile of the protein or polypeptide which has not been altered.

The mutant phytases of the present invention exhibit a number of improved attributes compared to their non-mutant counterpart phytases. For example, the mutant phytases of the present invention exhibit altered pH profiles and altered pH optima that favor their use in acidic environments, such as the gastrointestinal tracts of animals. The mutant phytases of the present invention exhibit such improved attributes without sacrificing their thermostability, in that the mutant phytases have equal or better thermostability than their non-mutant counterpart phytases.

BRIEF DESCRIPTION OF THE DRAWINGS

FIGS. 1A-C are graphs of the residual phytase activity of wild type Afp and Afp mutants after being heated at various temperatures for 10 minutes. FIG. 1A shows the activity of wild type Afp (+), Afp-E35A (◇), Afp-R168A (Δ), and Afp-R248A (*). FIG. 1B shows the activity of wild type Afp (+), Afp-E35A/R168A (×), Afp-E35A/R248A (□), and Afp-R168A/R248A (◆). FIG. 1C shows the activity of wild type Afp (+) and Afp-E35A/R168A/R248A ( ). An asterisk indicates a difference (P<0.05) between the residual activities of the wild type Afp and the Afp mutant at that temperature point.

FIGS. 2A-C are graphs of the residual phytase activity of wild type PhyA and PhyA mutants after incubation for 10 minutes at various temperatures. FIG. 2A shows the activity of wild type PhyA (◇), PhyA-A58E/Q191R (□), and PhyA-A58E/P65S (×). FIG. 2B shows the activity of wild type PhyA (◇) and PhyA-A58E/Q191R/T271R (Δ). FIG. 2C shows the activity of wild type PhyA (◇) and PhyA-A58E/P65S/Q191R/T271R ( ). An asterisk indicates a difference (P<0.05) between the residual activities of the wild type PhyA and the PhyA mutant at that temperature point.

FIGS. 3A-B are graphs relating to the melting temperature ($T_m$) of wild type PhyA (FIG. 3A) and the mutant PhyA-A58E/P65S/Q191R/T271R (FIG. 3B), as determined by differential scanning calorimetry.

FIGS. 4A-B are graphs of free inorganic phosphorus released from soy phytate hydrolysis by wild type PhyA (◇) and mutants PhyA-A58E/Q191R (□), PhyA-A58E/Q191R/T271R (Δ), PhyA-A58E/P65S (×), and PhyA-A58E/P65S/Q191R/T271R (*) at concentrations of 250, 500, 750, and 1000 U/kg soybean meal. FIG. 4A shows the results in 0.2 M citrate buffer at pH 5.5. FIG. 4B shows the results in 0.2 M citrate buffer at pH 3.5.

FIGS. 5A-F are schematic diagrams illustrating the structural prediction of the residual interactions in *A. fumigatus* phytase before (FIGS. 5A, 5C, and 5E) and after (FIGS. 5B, 5D, and 5F) substitutions at Glu35, Arg168, and Arg248. Dotted lines represent the hydrogen bond interactions. FIGS. 5A-B show the predicted change in hydrogen bond interactions caused by the substitution of E35A. FIGS. 5C-D show the predicted change in ionic interactions caused by the substitution of R168A. FIGS. 5E-F show the predicted change in hydrogen bond interactions caused by the substitution of R248A.

FIGS. 6A-C are schematic diagrams relating to the structural rationale of the designated mutations in *A. niger* PhyA. FIG. 6A is a comparison of hydrogen bonding between wild type PhyA (left) and the double mutant PhyA-A58E/P65S (right). Two new hydrogen bonds with distances of 3.01 Å and 3.66 Å, respectively, were introduced between substitutions Glu58 and Ser65 (right). No hydrogen bond is formed in the same positions in wild type PhyA (left). FIG. 6B illustrates that the single mutation Q191R removes a repulsive ionic interaction in the loop region. Arg191 also interacts with Asp184 through a salt bridge, thus stabilizing the structure. FIG. 6C shows Thr271 substituted to Arg271 so that it could interact with Asp267 through ionic interactions.

FIGS. 7A-D are graphs of the pH activity profiles of wild type PhyA and PhyA mutants at various pH. FIG. 7A shows the activity of wild type PhyA (◇) and PhyA-A58E/P65S/Q191R/E228K/T271R ("PhyA22") (+). FIG. 7B shows the activity of wild type PhyA (◇), PhyA-A58E/P65S/S149P/Q191R/E228K/T271R ("PhyA23") (□), and PhyA-A58E/P65S/F131L/S149P/Q191R/E228K/T271R ("PhyA24") (Δ). FIG. 7C shows the activity of wild type PhyA (◇), PhyA-A58E/P65S/K112R/F131L/S149P/Q191R/E228K/T271R ("PhyA25") (×), and PhyA-A58E/P65S/K112R/F131L/S149P/Q191R/K195R/E228K/T271R ("PhyA26") (*). FIG. 7D shows the activity of wild type PhyA (◇), PhyA-A58E/P65S/Q191R/T271R/K300E ("PhyA27") ( ), and PhyA-A58E/P65S/K112R/F131L/S149P/Q191R/K195R/E228K/T271R/K300E ("PhyA28") (–). The activity of each phytase enzyme at pH 5.5 was defined as 100%.

FIGS. 8A-C are graphs of the residual phytase activity of wild type PhyA and PhyA mutants after incubation for 10 minutes at various temperatures. FIG. 8A shows the activity of wild type PhyA (◇), PhyA-A58E/P65S/Q191R/T271R (–), PhyA22 (+), and PhyA27 ( ). FIG. 8B shows the activity of wild type PhyA (◇), PhyA23 (□), PhyA24 (Δ), and PhyA25 (×). FIG. 8C shows the activity of wild type PhyA (◇), PhyA26 (*), and PhyA28 (–). An asterisk indicates a difference (P<0.05) between the residual activities of the wild type PhyA and the PhyA mutant at that temperature point.

FIGS. 9A-C are graphs of the temperature dependence of enzymatic activity of wild type PhyA and PhyA mutants. FIG. 9A shows the activity of wild type PhyA (◇), PhyA22 (+), and PhyA27 ( ). FIG. 9B shows the activity of wild type PhyA (◇), PhyA23 (□), PhyA24 (Δ), and PhyA25 (×). FIG. 9C shows the activity of wild type PhyA (◇), PhyA26 (*), and PhyA28 (–). The phytase activities were measured directly at the temperatures indicated. The activity at 37° C. was defined as 100%.

FIG. 10 is a graph of free inorganic phosphorus released from soy phytate hydrolysis by wild type PhyA and mutants PhyA22, PhyA23, PhyA24, PhyA25, PhyA26, PhyA27, and PhyA28 at a concentration of 500 U/kg soybean meal in 0.2 M citrate buffer. White bars: pH 5; shaded bars: pH 3.5.

FIGS. 11A-C are schematic diagrams, illustrating the structural prediction of the residual interactions in PhyA (Kostrewa et al., "Crystal Structure of Phytase from *Aspergillus ficuum* at 2.5 Å Resolution," *Nature Struct. Biol.* 4:85-190 (1997), which is hereby incorporated by reference in its entirety) before (FIG. 11A) and after substitutions at E228 (FIGS. 11B and 11C) and K300 (FIG. 11C). Dotted lines represent the hydrogen bond interactions. FIGS. 11A-C were prepared using the PDB Viewer program.

FIGS. 12A-F are schematic diagrams, illustrating the structural prediction of the residual interactions in PhyA (Kostrewa et al., "Crystal Structure of Phytase from *Aspergillus ficuum* at 2.5 Å Resolution," *Nature Struct. Biol.* 4:85-190 (1997), which is hereby incorporated by reference in its entirety) before (FIGS. 12A, 12C, and 12E) and after (FIGS. 12B, 12D, and 12F) substitutions at K112, F131, and S149. FIGS. 12A-B show the predicted change in the flexibility of the loop and the location of F131 caused by the substitutions of F131L and S149P. FIGS. 12C-D show the predicted change in local folding caused by the substitution of F131L. FIGS. 12E-F show the predicted change in hydrogen bond interactions caused by the substitution of K112R. FIGS. 12A-F were prepared using the PDB Viewer program.

DETAILED DESCRIPTION OF THE INVENTION

The present invention relates to an isolated nucleic acid molecule encoding a mutant phytase. In one embodiment, the isolated nucleic acid molecule of the present invention can encode a mutant phytase that has an amino acid sequence having at least 90 percent (preferably at least 96 percent) sequence identity to SEQ ID NO: 2 over a region of at least 100 amino acid residues, and containing at least one substitution of at least one amino acid residue selected from the group consisting of residues A58, P65, K112, F131, S149, Q191, K195, and T271 of SEQ ID NO: 2. In another embodiment, the isolated nucleic acid molecule can encode a mutant phytase that has an amino acid sequence having at least 90 percent (preferably at least 96 percent) sequence identity to SEQ ID NO: 4 over a region of at least 100 amino acid residues, and containing at least one substitution of at least one amino acid residue selected from the group consisting of residues A205 and G277 of SEQ ID NO: 4.

*Aspergillus niger* phytase ("PhyA") (van Hartingsveldt et al., "Cloning, Characterization and Overexpression of the Phytase-encoding Gene (phyA) of *Aspergillus niger,*" *Gene* 127:87-94 (1993), which is hereby incorporated by reference in its entirety) is the most commonly used phytase in the animal feed industry (Mullaney et al., "Advances in Phytase Research," *Adv. Appl. Microbiol.* 47:157-99 (2000); Mullaney et al., "Site-directed Mutagenesis of *Aspergillus niger* NRRL 3135 Phytase at Residue 300 to Enhance Catalysis at pH 4.0," *Biochem. Biophys. Res. Commun.* 297:1016-20 (2002), which are hereby incorporated by reference in their entirety). When expressed in *Pichia pastoris*, PhyA retains only about 50% of its initial activity after being heated at 80° C. for 15 minutes (Han & Lei, "Role of Glycosylation in the Functional Expression of an *Aspergillus niger* Phytase (phyA) in *Pichia pastoris,*" *Arch. Biochem. Biophys.* 364:83-90 (1999), which is hereby incorporated by reference in its entirety). *Aspergillus fumigatus* phytase ("Afp") (Pasamontes et al., "Gene Cloning, Purification, and Characterization of a Heat-stable Phytase from the Fungus *Aspergillus fumigatus,*" *Appl. Environ. Microbiol.* 63:1696-700 (1997), which is hereby incorporated by reference in its entirety) is a well-known heat resilient phytase, and retains 90% of its initial activity after being heated at 100° C. for 20 minutes (Rodriguez et al., "Expression of the *Aspergillus fumigatus* Phytase Gene in *Pichia pastoris* and Characterization of the Recombinant Enzyme," *Biochem. Biophys. Res. Commun.* 268:373-8 (2000), which is hereby incorporated by reference in its entirety). Although PhyA displays much less heat resistance than Afp, it has a higher specific activity and a better pH profile (Ullah et al., "Biochemical Characterization of Cloned *Aspergillus fumigatus* Phytase (phyA)," *Biochem. Biophys. Res. Commun.* 275:279-85 (2000); Wyss et al., "Biophysical Characterization of Fungal Phytases (myo-Inositol Hexakisphosphate Phosphohydrolases): Molecular Size, Glycosylation Pattern, and Engineering of Proteolytic Resistance," *Appl. Environ. Microbiol.* 65:359-66 (1999); Wyss et al., "Comparison of the Thermostability Properties of Three Acid Phosphatases from Molds: *Aspergillus fumigatus* Phytase, *A. niger* Phytase, and *A. niger* pH 2.5 Acid Phosphatase," *Appl. Environ. Microbiol.* 64:4446-51 (1998), which are hereby incorporated by reference in their entirety).

Afp and PhyA share very similar overall crystal structures despite their significant differences in heat resistance (Kostrewa et al., "Crystal Structure of Phytase from *Aspergillus ficuum* at 2.5 Å Resolution," *Nature Struct. Biol.* 4:85-190 (1997); Liu et al., "Crystallographic Snapshots of *Aspergillus fumigatus* Phytase, Revealing Its Enzymatic Dynamics," *Structure* 12:1575-83 (2004); Xiang et al., "Crystal Structure of a Heat-resilient Phytase from *Aspergillus fumigatus*, Carrying a Phosphorylated Histidine," *J. Mol. Biol.* 339:437-45 (2004), which are hereby incorporated by reference in their entirety). Both enzymes contain a small α domain and a large α/β domain. The small α domain is composed of a long α helix and seven short α helices, and the large α/β domain contains a six-stranded β-sheet surrounded by two long α helices at one side and several short α helices at the other side. Detailed structure comparisons between these two enzymes indicate that three amino acid residues in Afp (E35, R168, and R248) may be critical in maintaining its heat resilience (Xiang et al., "Crystal Structure of a Heat-resilient Phytase from *Aspergillus fumigatus*, Carrying a Phosphorylated Histidine," *J. Mol. Biol.* 339:437-45 (2004), which is hereby incorporated by reference in its entirety). Specifically, E35 is predicted to be involved in a hydrogen bond network in the region spanning E35-S42, and R168 and R248 are predicted to interact with D161 and D244, respectively, to form multiple salt bridges (Xiang et al., "Crystal Structure of a Heat-resilient Phytase from *Aspergillus fumigatus*, Carrying a Phosphorylated Histidine," *J. Mol. Biol.* 339:437-45 (2004), which is hereby incorporated by reference in its entirey). Based on their crystal structures and a sequence alignment of Afp and PhyA, three residues in PhyA (A58, Q191, and T271) that correspond, respectively, to E35, R168, and R248 of Afp were identified. Since these three residues are not predicted from its crystal structure to form any hydrogen bonding in PhyA (Kostrewa et al., "Crystal Structure of Phytase from *Aspergillus ficuum* at 2.5 Å Resolution," *Nature Struct. Biol.* 4:85-190 (1997); Tomschy et al., "Active Site Residue 297 of *Aspergillus niger* Phytase Critically Affects the Catalytic Properties," *FEBS Lett.* 472:169-72 (2000), which are hereby incorporated by reference in their entirety), it was predicted that they are associated with the lower thermostability of PhyA.

Therefore, a series of Afp and PhyA mutants were constructed by site-directed mutagenesis to determine: 1) the individual or combined contributions of E35, R168, and R248, which are involved in hydrogen bonding and ionic interactions, to Afp's thermal stability; and 2) whether the thermal stability of PhyA could be improved by substituting residues of PhyA for those in the corresponding positions of Afp that have the presumed ability to mediate putative hydrogen bonding and ionic interactions.

In particular, in order to study the involvement of E35, R168, and R248 in hydrogen bonding and ionic interactions and their contributions to the thermal stability of Afp, site-directed mutagenesis was used to mutate these residues to alanine, which is expected to no longer participate in the interactions. Each of the three residues was thus altered, resulting in three single-substitution mutants (Afp-E35A, Afp-R168A, and Afp-R248A). Each single substitution was then combined with each other, resulting in three double-substitution mutants (Afp-E35A/R168A, Afp-R168A/R248A, and Afp-E35A/R248A), and one triple-substitution mutant (Afp-E35A/R168A/R248A). The thermostability and other enzymatic properties of each mutant were compared to those of wild type Afp. Residual substitutions that interrupt important hydrogen bonds and ionic interactions inevitably decreased the enzyme's thermostability.

The residues in the corresponding positions in PhyA were also substituted with residues predicted to mediate putative hydrogen bonding and ionic interactions to improve thermostability. Residues Ala58, Pro65, Gln191, and Thr271 of PhyA were substituted with Glu, Ser, Arg, and Arg, respectively, in order to produce PhyA variants with higher thermal stability. Three single-substitution mutants (PhyA-A58E, PhyA-Q191R, and PhyA-T271R), four double-substitution mutants (PhyA-A58E/Q191R, PhyA-A58E/T271R, PhyA-Q191R/T271R, and PhyA-A58E/P65S), one triple-substitution mutant (PhyA-A58E/Q191R/T271R), and one multi-substitution mutant (PhyA-A58E/P65S/Q 191R/T271R) were produced by site-directed mutagenesis. These mutants were then tested for their thermal stability and other enzymatic properties. The thermostability of selected PhyA variants were also tested under practical conditions in soy-phytate hydrolysis experiments.

Four different residual substitutions in PhyA (A58E, P65S, Q191R, and T271R) were found to enhance the enzyme's thermostability. The PhyA mutant bearing all four substitutions (PhyA-A58E/P65S/Q191R/T271R) retained >20% greater residual activity after being heated at ≧80° C. for 10 minutes and had a 7° C. higher melting temperature than wild type PhyA. Kinetic measurements revealed a better binding affinity toward sodium phytate. In addition, the mutant did not suffer any loss of specific activity at 37° C. or show any change in the pH activity profile.

Further work was carried out to determine whether various thermo-stabilizing and pH profile-shifting mutations were cumulative and synergistic in PhyA, to engineer mutant phytases with both improved thermostability and an improved pH profile.

PhyA has a bi-peak pH profile, with two pH optima at pH 2.5 and 5.5, respectively. However, there is a sharp activity dip at pH 3.5, which is the pH of the stomach of animals (Han & Lei, "Role of Glycosylation in the Functional Expression of an *Aspergillus niger* Phytase (phyA) in *Pichia pastoris*," *Arch. Biochem. Biophys.* 364:83-90 (1999); Wyss et al., "Biochemical Characterization of Fungal Phytases (myo-Inositol Hexakisphosphate Phosphohydrolases): Catalytic Properties," *Appl. Environ. Microbiol.* 65:367-73 (1999), which are hereby incorporated by reference in their entirety). The crystal structure of PhyA indicates that the substrate binding site of PhyA consists of the following residues: K91, K94, E228, D262, Q297, K300, and K301 (Kostrewa et al., "Crystal Structure of Phytase from *Aspergillus ficuum* at 2.5 Å Resolution," *Nature Struct. Biol.* 4:85-190 (1997), which is hereby incorporated by reference in its entirety). Substitutions of residues in the substrate binding site have been shown to affect the pH activity profile of PhyA. The unique bi-peak pH profile of PhyA could also be attributed to the interactions of the acidic and basic residues in the substrate binding site (Mullaney et al., "Site-directed Mutagenesis of *Aspergillus niger* NRRL 3135 Phytase at Residue 300 to Enhance Catalysis at pH 4.0," *Biochem. Biophys. Res. Commun.* 297:1016-20 (2002), which is hereby incorporated by reference in its entirety).

The effect on thermostability was further investigated by sequentially adding another set of four residue substitutions, S149P, F131L, K112R, and K195R, which were identified from random mutagenesis. In addition, two other residue substitutions, E228K and K300E that have been shown to affect the pH profile of PhyA (Mullaney et al., "Site-directed Mutagenesis of *Aspergillus niger* NRRL 3135 Phytase at Residue 300 to Enhance Catalysis at pH 4.0," *Biochem. Biophys. Res. Commun.* 297:1016-20 (2002); Kim et al., "Shifting the pH Profile of *Aspergillus niger* PhyA Phytase to Match the Stomach pH Enhances Its Effectiveness as an Animal Feed Additive," *Appl. Environ. Microbiol.* 72:4397-403 (2006), which are hereby incorporated by reference in their entirety) were also combined to the thermostable mutants. The substitution of S149P substantially decreased the phytase activity loss caused by heating at various temperatures between 50° C. and 100° C. The F131L substitution also slightly improved the protein thermostability. The E228K substitution shifted the pH optima of the thermostable mutants from 5.5 to 4.0 and increased the specific activities of the mutants at pH 3.5, without sacrificing protein thermostability. Furthermore, two mutants (PhyA-A58E/P65S/Q191R/E228K/T271R ("PhyA22") and PhyA-A58E/P65S/S149P/Q191R/E228K/T271R ("PhyA23")) demonstrated higher binding affinities toward Na-phytate and more efficient hydrolysis of phytate in soybean meal.

As referred to herein, SEQ ID NO: 1 corresponds to the nucleotide sequence of the wild-type *Aspergillus niger* PhyA phytase (GenBank Accession No. M94550) and has the following nucleotide sequence:

```
gcatgcagca ctgtcagcaa ataaattgct ttgaatgatt        60
ttctgcttct tctcatattg ggctatagac actgccgtta tctgactttt aatgagcgag       120
ggcgatgttc atcattcggc gttctgttct tatgatttcc ccacgtcctt tcgggctttc       180
ggcacagcaa aatagattgt ttagcaggta cagaaacaac ttgatgacac atgcatccga       240
gaatcttcag ccgtggaagc attcatgtag atctttgcta agagaaatga tggcggccca       300
gggcatccag gcacctttc caacggggaa cttccgccgt ccacgtgctc tgattcagcc       360
aatcaagacg tcccacggca atgctggatc aacgatcaac ttgaatgcaa taaatgaaga       420
tggaactaac accatctgct gcctttctct cgagaaagct cctccacttc tcccactaga       480
tatctccgtc cccgtcgact tcccgtccta ttcggcctcg tccgctgaag atccatccca       540
ccattgcacg tgggccacct ttgtgagctt ctaacctgaa ctggtagagt atcacacacc       600
atgccaaggt gggatgaagg ggttatatag gaccgtccgg tccggcgcga tggccgtagc       660
tgccactcgc tgctgtgcaa gaaattactt ctcataggca tcatgggcgt ctctgctgtt       720
ctacttcctt tgtatctcct gtctgggtat gctaagcacc acaatcaaag tctaataagg       780
accctccctt ccgagggccc ctgaagctcg gactgtgtgg gactactgat cgctgactat       840
ctgtgcagag tcacctccgg actggcagtc cccgcctcga gaaatcaatc cagttgcgat       900
acggtcgatc aggggtatca atgcttctcc gagacttcgc atctttgggg tcaatacgca       960
ccgttcttct ctctggcaaa cgaatcggtc atctcccctg aggtgcccgc cggatgcaga      1020
gtcactttcg ctcaggtcct ctcccgtcat ggagcgcggt atccgaccga ctccaagggc      1080
aagaaatact ccgctctcat tgaggagatc cagcagaacg cgaccacctt tgacggaaaa      1140
tatgccttcc tgaagacata caactacagc ttgggtgcag atgacctgac tcccttcgga      1200
gaacaggagc tagtcaactc cggcatcaag ttctaccagc ggtacgaatc gctcacaagg      1260
aacatcgttc cattcatccg atcctctggc tccagccgcg tgatcgcctc cggcaagaaa      1320
ttcatcgagg gcttccagag caccaagctg aaggatcctc gtgcccagcc cggccaatcg      1380
tcgcccaaga tcgacgtggt catttccgag gccagctcat ccaacaacac tctcgaccca      1440
ggcacctgca ctgtcttcga agacagcgaa ttggccgata ccgtcgaagc caatttcacc      1500
gccacgttcg tcccctccat tcgtcaacgt ctggagaacg acctgtccgg tgtgactctc      1560
acagacacag aagtgaccta cctcatggac atgtgctcct tcgacaccat ctccaccagc      1620
accgtcgaca ccaagctgtc
```

-continued

```
ccccttctgt gacctgttca cccatgacga atggatcaac    1680
tacgactacc tccagtcctt gaaaaagtat tacggccatg gtgcaggtaa cccgctcggc    1740
ccgacccagg gcgtcggcta cgctaacgag ctcatcgccc gtctgaccca ctcgcctgtc    1800
cacgatgaca ccagttccaa ccacactttg gactcgagcc cggctacctt tccgctcaac    1860
tctactctct acgcggactt ttcgcatgac aacggcatca tctccattct ctttgcttta    1920
ggtctgtaca acggcactaa gccgctatct accacgaccg tggagaatat cacccagaca    1980
gatggattct cgtctgcttg gacggttccg tttgcttcgc gtttgtacgt cgagatgatg    2040
cagtgtcagg cggagcagga gccgctggtc cgtgtcttgg ttaatgatcg cgttgtcccg    2100
ctgcatgggt gtccggttga tgctttgggg agatgtaccc gggatagctt tgtgaggggg    2160
ttgagctttg ctagatctgg gggtgattgg gcggagtgtt ttgcttagct gaattacctt    2220
gatgaatggt atgtatcagc attgcatatc attagcactt caggtatgta ttatcgaaga    2280
tgtatatcga aaggatcaat ggtgactgtc actggttatc tgaatatccc tctataccct    2340
gcccacaacc aatcatcacc cttttaaacaa tcacactcaa gccacagcgt acaaacgaac    2400
aaacgcacaa agaatatttt acactcctcc ccaacgcaat accaaccgca attcatcata    2460
cctcatataa atacaataca atacaataca tccatcccta ccctcaagtc cacccatcct    2520
ataatcaatc cctacttact tacttctccc cctccccctc acccttccca gaactcaccc    2580
ccgaagtagt aatagtagta gtagaagaag cagacgacct ctccaccaat ctcttcggcc    2640
tcttatcccc atacgctaca caaaaccccc accccgttag catgc                    2665
```

As referred to herein, SEQ ID NO: 2 is the amino acid sequence of the wild-type *Aspergillus niger* PhyA phytase (GenBank Accession No. P34752), and has an amino acid sequence as follows:

```
Met Gly Val Ser Ala Val Leu Leu Pro Leu Tyr Leu
 1               5                   10

Leu Ser Gly Val Thr Ser Gly Leu Ala Val Pro Ala
            15                  20

Ser Arg Asn Gln Ser Ser Cys Asp Thr Val Asp Gln
25              30                      35

Gly Tyr Gln Cys Phe Ser Glu Thr Ser His Leu Trp
            40                  45

Gly Gln Tyr Ala Pro Phe Phe Ser Leu Ala Asn Glu
    50              55                      60

Ser Val Ile Ser Pro Glu Val Pro Ala Gly Cys Arg
                65                  70

Val Thr Phe Ala Gln Val Leu Ser Arg His Gly Ala
            75                  80

Arg Tyr Pro Thr Asp Ser Lys Gly Lys Lys Tyr Ser
        85              90                  95

Ala Leu Ile Glu Glu Ile Gln Gln Asn Ala Thr Thr
                100                 105

Phe Asp Gly Lys Tyr Ala Phe Leu Lys Thr Tyr Asn
            110                 115             120

Tyr Ser Leu Gly Ala Asp Asp Leu Thr Pro Phe Gly
                    125             130

Glu Gln Glu Leu Val Asn Ser Gly Ile Lys Phe Tyr
                135                 140

Gln Arg Tyr Glu Ser Leu Thr Arg Asn Ile Val Pro
145                 150                     155

Phe Ile Arg Ser Ser Gly Ser Ser Arg Val Ile Ala
                160                 165

Ser Gly Lys Lys Phe Ile Glu Gly Phe Gln Ser Thr
            170                 175             180

Lys Leu Lys Asp Pro Arg Ala Gln Pro Gly Gln Ser
                    185                 190

Ser Pro Lys Ile Asp Val Val Ile Ser Glu Ala Ser
                195                 200

Ser Ser Asn Asn Thr Leu Asp Pro Gly Thr Cys Thr
205                 210                     215

Val Phe Glu Asp Ser Glu Leu Ala Asp Thr Val Glu
                220                 225

Ala Asn Phe Thr Ala Thr Phe Val Pro Ser Ile Arg
            230                 235             240

Gln Arg Leu Glu Asn Asp Leu Ser Gly Val Thr Leu
                    245                 250

Thr Asp Thr Glu Val Thr Tyr Leu Met Asp Met Cys
                255                 260

Ser Phe Asp Thr Ile Ser Thr Ser Thr Val Asp Thr
265                 270                     275

Lys Leu Ser Pro Phe Cys Asp Leu Phe Thr His Asp
                280                 285

Glu Trp Ile Asn Tyr Asp Tyr Leu Gln Ser Leu Lys
            290                 295             300

Lys Tyr Tyr Gly His Gly Ala Gly Asn Pro Leu Gly
                    305                 310

Pro Thr Gln Gly Val Gly Tyr Ala Asn Glu Leu Ile
                315                 320

Ala Arg Leu Thr His Ser Pro Val His Asp Asp Thr
325                 330                     335

Ser Ser Asn His Thr Leu Asp Ser Ser Pro Ala Thr
                340                 345

Phe Pro Leu Asn Ser Thr Leu Tyr Ala Asp Phe Ser
            350                 355             360

His Asp Asn Gly Ile Ile Ser Ile Leu Phe Ala Leu
                    365                 370

Gly Leu Tyr Asn Gly Thr Lys Pro Leu Ser Thr Thr
                375                 380

Thr Val Glu Asn Ile Thr Gln Thr Asp Gly Phe Ser
385                 390                     395

Ser Ala Trp Thr Val Pro Phe Ala Ser Arg Leu Tyr
                400                 405
```

-continued

```
    Val Glu Met Met Gln Cys Gln Ala Glu Gln Glu Pro
        410                 415                 420

Leu Val Arg Val Leu Val Asn Asp Arg Val Val Pro
                    425                 430

Leu His Gly Cys Pro Val Asp Ala Leu Gly Arg Cys
                435                 440

Thr Arg Asp Ser Phe Val Arg Gly Leu Ser Phe Ala
    445                 450                 455

Arg Ser Gly Gly Asp Trp Ala Glu Cys Phe Ala
                460                 465
```

As referred to herein, SEQ ID NO: 3 corresponds to the nucleotide sequence of the wild-type *Aspergillus fumigatus* phytase (GenBank Accession No. U59804) and has the following nucleotide sequence:

```
   1 ggaaacccat ccctgctct cacgcgacag agtcacgaat
     cgctccaccg acgataggct 61 actcgtcctg taaaccagct gattgtctac cggtgtggtg
     cgacgggtaa gctgggctcc 121 actaggctca gaccccccgt ttcgtatgcg aagggggagt
     gcgatgtgag tcgggcggga 181 agagatggaa aagctatata atggccggcg tgtccggcga
     ggggaggatg gtttccgat 241 cagattcaac gacggaggaa tcgcaaccct aattgtcggt
     atcatggtga ctctgacttt 301 cctgctttcg gcgcgtatc tgctttctgg gtgagtggct
     tggatctatt gctcggatag 361 ggctgtggtg ctgattctga aacggagtag agtgtctgcg
     gcacctagtt ctgctggctc 421 caagtcctgc gatacggtag acctcgggta ccagtgctcc
     cctgcgactt ctcatctatg 481 gggccagtac tcgccattct tttcgctcga ggacgagctg
     tccgtgtcga gtaagcttcc 541 caaggattgc cggatcacct tggtacaggt gctatcgcgc
     catggagcgc ggtacccaac 601 cagctccaag agcaaaaagt ataagaagct tgtgacggcg
     atccaggcca atgccaccga 661 cttcaagggc aagtttgcct ttttgaagac gtacaactat
     actctgggtg cggatgacct 721 cactcccttt ggggagcagc agctggtgaa ctcgggcatc
     aagttctacc agaggtacaa 781 ggctctggcg cgcagtgtgg tgccgtttat tcgcgcctca
     ggctcggacc gggttattgc 841 ttcgggagag aagttcatcg aggggttcca gcaggcgaag
     ctggctgatc ctggcgcgac 901 gaaccgcgcc gctccggcga ttagtgtgat tattccggag
     agcgagacgt tcaacaatac 961 gctggaccac ggtgtgtgca cgaagtttga ggcgagtcag
     ctgggagatg aggttgcggc 1021 caatttcact gcgctctttg cacccgacat ccgagctcgc
     gccgagaagc atcttcctgg 1081 cgtgacgctg acagacgagg acgttgtcag tctaatggac
     atgtgttcgt tgatacggt
```

-continued

```
1141 agcgcgcacc agcgacgcaa gtcagctgtc accgttctgt
     caactcttca ctcacaatga 1201 gtggaagaag tacaactacc ttcagtcctt gggcaagtac
     tacggctacg gcgcaggcaa 1261 ccctctggga ccggctcagg ggatagggtt caccaacgag
     ctgattgccc ggttgactcg 1321 ttcgccagtg caggaccaca ccagcactaa ctcgactcta
     gtctccaacc cggccacctt 1381 cccgttgaac gctaccatgt acgtcgactt ttcacacgac
     aacagcatgg tttccatctt 1441 ctttgcattg ggcctgtaca acggcactga acccttgtcc
     cggacctcgg tggaaagcgc 1501 caaggaattg gatgggtatt ctgcatcctg ggtggtgcct
     ttcggcgcgc gagcctactt 1561 cgagacgatg caatgcaagt cggaaaagga gcctcttgtt
     cgcgctttga ttaatgaccg 1621 ggttgtgcca ctgcatggct gcgatgtgga caagctgggg
     cgatgcaagc tgaatgactt 1681 tgtcaaggga ttgagttggg ccagatctgg gggcaactgg
     ggagagtgct ttagttgaga 1741 tgtcattgtt atgctatact ccaatagacc gttgcttagc
     cattcacttc actttgctcg 1801 aaccgcctgc cg
```

As referred to herein, SEQ ID NO: 4 is the amino acid sequence of the wild-type *Aspergillus fumigatus* phytase (GenBank Accession No. U59804), and has an amino acid sequence as follows:

```
    Glu Ala Glu Phe Ser Lys Ser Cys Asp Thr Val Asp
    1                   5                   10

Leu Gly Tyr Gln Cys Ser Pro Ala Thr Ser His Leu
                    15                  20

Trp Gly Gln Tyr Ser Pro Phe Phe Ser Leu Glu Asp
    25                  30                  35

Glu Leu Ser Val Ser Ser Lys Leu Pro Lys Asp Cys
                        40                  45

Arg Ile Thr Leu Val Gln Val Leu Ser Arg His Gly
        50                  55                  60

Ala Arg Tyr Pro Thr Ser Ser Lys Ser Lys Lys Tyr
                    65                  70

Lys Lys Leu Val Thr Ala Ile Gln Ala Asn Ala Thr
                75                  80

Asp Phe Lys Gly Lys Phe Ala Phe Leu Lys Thr Tyr
    85                  90                  95

Asn Tyr Thr Leu Gly Ala Asp Asp Leu Thr Pro Phe
                    100                 105

Gly Glu Gln Gln Leu Val Asn Ser Gly Ile Lys Phe
                    110                 115                 120

Tyr Gln Arg Tyr Lys Ala Leu Ala Arg Ser Val Val
                    125                 130

Pro Phe Ile Arg Ala Ser Gly Ser Asp Arg Val Ile
                    135                 140

Ala Ser Gly Glu Lys Phe Ile Glu Gly Phe Gln Gln
    145                 150                 155
```

-continued

```
Ala Lys Leu Ala Asp Pro Gly Ala --- Thr Asn Arg
            160             165
Ala Ala Pro Ala Ile Ser Val Ile Ile Pro Glu Ser
    170             175             180
Glu Thr Phe Asn Asn Thr Leu Asp His Gly Val Cys
            185             190
Thr Lys Phe Glu Ala Ser Gln Leu Gly Asp Glu Val
    195             200
Ala Ala Asn Phe Thr Ala Leu Phe Ala Pro Asp Ile
205             210             215
Arg Ala Arg Ala Glu Lys His Leu Pro Gly Val Thr
            220             225
Leu Thr Asp Glu Asp Val Val Ser Leu Met Asp Met
    230             235             240
Cys Ser Phe Asp Thr Val Ala Arg Thr Ser Asp Ala
            245             250
Ser Gln Leu Ser Pro Phe Cys Gln Leu Phe Thr His
            255             260
Asn Glu Trp Lys Lys Tyr Asn Tyr Leu Gln Ser Leu
265             270             275
Gly Lys Tyr Tyr Gly Tyr Gly Ala Gly Asn Pro Leu
            280             285
Gly Pro Ala Gln Gly Ile Gly Phe Thr Asn Glu Leu
    290             295             300
Ile Ala Arg Leu Thr Arg Ser Pro Val Gln Asp His
            305             310
Thr Ser Thr Asn Ser Thr Leu Val Ser Asn Pro Ala
            315             320
Thr Phe Pro Leu Asn Ala Thr Met Tyr Val Asp Phe
325             330             335
Ser His Asp Asn Ser Met Val Ser Ile Phe Phe Ala
            340             345
Leu Gly Leu Tyr Asn Gly Thr Glu Pro Leu Ser Arg
    350             355             360
Thr Ser Val Glu Ser Ala Lys Glu Leu Asp Gly Tyr
            365             370
Ser Ala Ser Trp Val Val Pro Phe Gly Ala Arg Ala
            375             380
Tyr Phe Glu Thr Met Gln Cys Lys Ser Glu Lys Glu
385             390             395
Pro Leu Val Arg Ala Leu Ile Asn Asp Arg Val Val
            400             405
Pro Leu His Gly Cys Asp Val Asp Lys Leu Gly Arg
    410             415             420
Cys Lys Leu Asn Asp Phe Val Lys Gly Leu Ser Trp
            425             430
Ala Arg Ser Gly Gly Asn Trp Gly Glu Cys Phe Ser
            435             440
```

Residues 1-4 (italics) of SEQ ID NO: 4 are from the α-factor of the expression vector. The mature protein begins at residue 5. Residues E35, R168, and R248 are shown in bold.

As referenced herein, amino acid substitutions may be indicated using conventional one-letter abbreviations for the amino acid residues involved in the substitutions. Table 1 describes the one-letter and three-letter codes for the various amino acid residues.

TABLE 1

Three-Letter and One-Letter Codes for Amino Acid Residues

| Amino Acid | 3-Letter Code | 1-Letter Code |
|---|---|---|
| Alanine | Ala | A |
| Cysteine | Cys | C |
| Aspartic acid or aspartate | Asp | D |
| Glutamic acid or glutamate | Glu | E |
| Phenylalanine | Phe | F |
| Glycine | Gly | G |
| Histidine | His | H |
| Isoleucine | Ile | I |
| Lysine | Lys | K |
| Leucine | Leu | L |
| Methionine | Met | M |
| Asparagine | Asn | N |
| Proline | Pro | P |
| Glutamine | Gln | Q |
| Arginine | Arg | R |
| Serine | Ser | S |
| Threonine | Thr | T |
| Valine | Val | V |
| Tryptophan | Trp | W |
| Tyrosine | Tyr | Y |

As generally described herein, a single amino acid residue substitution can be indicated as follows: the original amino acid residue (expressed as a single-letter abbreviation), followed by the position of the original amino acid residue (i.e., a numerical expression), followed by the new amino acid residue (expressed as a single-letter abbreviation) to be inserted in place of the original amino acid residue. For example, "Q50L" means that the original glutamine (Q) residue at position 50 is to be replaced by the new leucine (L) residue. For multiple substitutions (e.g., double-substitutions, triple-substitutions, and quadruple-substitutions), the various substitutions are separated by either a slash (/) or by a space. An example of a double-substitution may be expressed as either "K300T/E228K" or as "K300T E228K." In such a double-substitution, there are two mutations: the K residue at position 300 is replaced with a T residue, and the E residue at position 228 is replaced with a K residue.

With respect to the isolated nucleic acid molecules of the present invention that encode mutant phytases that have at least 90 percent sequence identity to SEQ ID NO: 2 over a region of at least 100 amino acid residues, the at least one substitution can be, without limitation, as follows:

The at least one substitution can be of an amino acid residue corresponding to amino acid residue 58 of SEQ ID NO: 2. Examples of suitable substitutions of an amino acid residue corresponding to residue 58 of SEQ ID NO: 2 can include A58E.

The at least one substitution can also be of an amino acid residue corresponding to amino acid residue 65 of SEQ ID NO: 2. Examples of suitable substitutions of an amino acid residue corresponding to residue 65 of SEQ ID NO: 2 can include P65S.

The at least one substitution can also be of an amino acid residue corresponding to amino acid residue 112 of SEQ ID NO: 2. Examples of suitable substitutions of an amino acid residue corresponding to residue 112 of SEQ ID NO: 2 can include K112R.

The at least one substitution can also be of an amino acid residue corresponding to amino acid residue 131 of SEQ ID NO: 2. Examples of suitable substitutions of an amino acid residue corresponding to residue 131 of SEQ ID NO: 2 can include F131L.

The at least one substitution can also be of an amino acid residue corresponding to amino acid residue 149 of SEQ ID NO: 2. Examples of suitable substitutions of an amino acid residue corresponding to residue 149 of SEQ ID NO: 2 can include S149P.

The at least one substitution can also be of an amino acid residue corresponding to amino acid residue 191 of SEQ ID NO: 2. Examples of suitable substitutions of an amino acid residue corresponding to residue 191 of SEQ ID NO: 2 can include Q191R.

The at least one substitution can also be of an amino acid residue corresponding to amino acid residue 195 of SEQ ID NO: 2. Examples of suitable substitutions of an amino acid residue corresponding to residue 195 of SEQ ID NO: 2 can include K195R.

The at least one substitution can also be of an amino acid residue corresponding to amino acid residue 271 of SEQ ID NO: 2. Examples of suitable substitutions of an amino acid residue corresponding to residue 271 of SEQ ID NO: 2 can include T271R.

The at least one substitution can also be a double-substitution. Examples of suitable double-substitutions can include, without limitation, substitutions of at least two different amino acid residues corresponding to the following substitutions of SEQ ID NO: 2: A58E and Q191R ("A58E/Q191R"), A58E and T271R ("A58E/T271R"), Q191R and T271R ("Q191R/T271R"), and A58E and P65S ("A58E/P65S").

The at least one substitution can also be a triple-substitution. Examples of suitable triple-substitutions can include, without limitation, substitutions of at least three different amino acid residues corresponding to the following substitutions of SEQ ID NO: 2: A58E, Q191R, and T271R ("A58E/Q191R/T271R").

The at least one substitution can also be a quadruple-substitution. Examples of suitable quadruple-substitutions can include, without limitation, substitutions of at least four different amino acid residues corresponding to the following substitutions of SEQ ID NO: 2: A58E, P65S, Q191R, and T271R ("A58E/P65S/Q191R/T271R").

Preferably, the at least one substitution is selected from the group of A58E, P65S, F131L, S149P, Q191R, and T271R of SEQ ID NO: 2.

Preferred substitutions include, without limitation, A58E/Q191R, A58E/P65S, A58E/Q191R/T271R, and A58E/P65S/Q191R/T271R of SEQ ID NO: 2.

In one embodiment, the protein or polypeptide further includes at least one substitution of at least one amino acid residue selected from the group of residues E228 and K300 of SEQ ID NO: 2. Examples of suitable substitutions of an amino acid residue corresponding to residue 228 of SEQ ID NO: 2 can include E228K. Examples of suitable substitutions of an amino acid residue corresponding to residue 300 of SEQ ID NO: 2 can include K300E.

With respect to this embodiment, the at least one substitution can be, without limitation, as follows:

The at least one substitution can be a quintuple-substitution. Examples of suitable quintuple-substitutions can include, without limitation, substitutions of at least five different amino acid residues corresponding to the following substitutions of SEQ ID NO: 2: A58E, P65 S, Q191R, T271R, and K300E ("A58E/P65S/Q191R/T271R/K300E"); and A58E, P65S, Q191R, E228K, and T271R ("A58E/P65S/Q191R/E228K/T271R").

The at least one substitution can also be a sextuple-substitution. Examples of suitable sextuple-substitutions can include, without limitation, substitutions of at least six different amino acid residues corresponding to the following substitutions of SEQ ID NO: 2: A58E, P65S, S149P, Q191R, E228K, and T271R ("A58E/P65S/S149P/Q191R/E228K/T271R").

The at least one substitution can also be a septuple-substitution. Examples of suitable septuple-substitutions can include, without limitation, substitutions of at least seven different amino acid residues corresponding to the following substitutions of SEQ ID NO: 2: A58E, P65S, F131L, S149P, Q191R, E228K, and T271R ("A58E/P65S/F131L/S149P/Q191R/E228K/T271R").

The at least one substitution can also be an octuple-substitution. Examples of suitable octuple-substitutions can include, without limitation, substitutions of at least eight different amino acid residues corresponding to the following substitutions of SEQ ID NO: 2: A58E, P65S, K112R, F131L, S149P, Q191R, E228K, and T271R ("A58E/P65S/K112R/F131L/S149P/Q191R/E228K/T271R").

The at least one substitution can also be a nonuple-substitution. Examples of suitable nonuple-substitutions can include, without limitation, substitutions of at least nine different amino acid residues corresponding to the following substitutions of SEQ ID NO: 2: A58E, P65S, K112R, F131L, S149P, Q191R, K195R, E228K, and T271R ("A58E/P65S/K112R/F131L/S149P/Q191R/K195R/E228K/T271R").

The at least one substitution can also be a denary-substitution. Examples of suitable denary-substitutions can include, without limitation, substitutions of at least ten different amino acid residues corresponding to the following substitutions of SEQ ID NO: 2: and A58E, P65S, K112R, F131L, S149P, Q191R, K195R, E228K, T271R, and K300E ("A58E/P65S/K112R/F131L/S149P/Q191R/K195R/E228K/T271R/K300E").

Although exemplary quintuple-through denary-substitutions are set forth, phytases having fewer substitutions (i.e., double-, triple-, and quadruple-substitutions) are also contemplated, as are phytases having more than ten substitutions.

Preferred substitutions include, without limitation, A58E/P65S/Q191R/E228K/T271R, A58E/P65S/S149P/Q191R/E228K/T271R, A58E/P65S/F131L/S149P/Q191R/E228K/T271R, A58E/P65 S/K112R/F131L/S149P/Q191R/E228K/T271R, and A58E/P65S/K112R/F131L/S149P/Q191R/K195R/E228K/T271R.

With respect to the isolated nucleic acid molecules of the present invention that encode mutant phytases that have at least 90 percent sequence identity to SEQ ID NO: 4 over a region of at least 100 amino acid residues, the substitution of an amino acid residue corresponding to residue 205 of SEQ ID NO: 4 can be, without limitation, A205K. The substitution of an amino acid residue corresponding to residue 277 of SEQ ID NO: 4 can be, without limitation, G277E.

Other suitable phytases that can be used in the various aspects of the present invention as templates for amino acid residue substitutions can be derived from various sources, including, without limitation, from other wild-type phytases of *Aspergillus* species.

The present invention also relates to a recombinant DNA expression system containing a nucleic acid molecule of the present invention. The nucleic acid molecule can be in a heterologous expression vector.

The present invention further relates to a host cell containing a heterologous nucleic acid molecule of the present invention. The host cell can be a yeast cell or a non-yeast cell. Examples of particular yeast host cells include, without limitation, *Saccharomyces*, *Kluyveromyces*, *Torulaspora*, *Schizosaccharomyces*, *Pichia*, *Hansenula*, *Torulupsis*, *Candida*, and *Karwinskia*. In another preferred embodiment of the present invention, the yeast strain is a methylotrophic yeast strain. Methylotrophic yeast are those yeast genera capable of utilizing methanol as a carbon source for the production of the energy resources necessary to maintain cellular function and containing a gene for the expression of alcohol oxidase. Typical methylotrophic yeasts include members of the genera *Pichia, Hansenula, Torulopsis, Candida*, and *Karwinskia*. These yeast genera can use methanol as a sole carbon source. In a more preferred embodiment, the methylotrophic yeast strain is *Pichia pastoris*. Examples of particular non-yeast host cells include, without limitation, bacterial and fungal cells. Suitable examples of non-yeast fungal host cells can include *Aspergillus* species, *Trichoderma* species, and *Neurospora* species.

The present invention also relates to a method of recombinantly producing a mutant phytase. This method involves transforming a host cell with at least one heterologous nucleic acid molecule of the present invention under conditions suitable for expression of the mutant phytase. The mutant phytase is then isolated. Suitable host cells for this method are as described herein (above).

The isolated nucleic acid molecule of the present invention can be expressed in any prokaryotic or eukaryotic expression system by incorporation of the isolated nucleic acid molecule of the present invention in the expression system in proper orientation and correct reading frame. A variety of host-vector systems may be utilized to express the protein-encoding sequence(s). Preferred vectors include a viral vector, plasmid, cosmid, or an oligonucleotide. Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used. For example, an isolated nucleic acid molecule in accordance with the present invention is spliced in frame with a transcriptional enhancer element.

The present invention also provides a yeast strain having a heterologous gene which encodes a mutant phytase with phytase activity. The heterologous gene should be functionally linked to a promoter capable of expressing the mutant phytase in yeast.

Yet another aspect of the invention is a vector for expressing the mutant phytase (encoded by the isolated nucleic acid molecule of the present invention) in yeast. The isolated nucleic acid molecule of the present invention can be cloned into any vector which replicates autonomously or integrates into the genome of yeast. The copy number of autonomously replicating plasmids, e.g., YEp plasmids, may be high, but their mitotic stability may be insufficient (Bitter et al., "Expression and Secretion Vectors for Yeast," *Meth. Enzymol.* 153:516-44 (1987), which is hereby incorporated by reference in its entirety). They may contain the 2 mu-plasmid sequence responsible for autonomous replication, and an *E. coli* sequence responsible for replication in *E. coli*. The vectors preferably contain a genetic marker for selection of yeast transformants, and an antibiotic resistance gene for selection in *E. coli*. The episomal vectors containing the ARS and CEN sequences occur as a single copy per cell, and they are more stable than the YEp vectors. Integrative vectors are used when a DNA fragment is integrated as one or multiple copies into the yeast genome. In this case, the recombinant DNA is stable and no selection is needed (Struhl et al., "High-frequency Transformation of Yeast: Autonomous Replication of Hybrid DNA Molecules," *Proc. Nat'l Acad. Sci. USA* 76:1035-9 (1979); POUWELS ET AL., I-IV CLONING VECTORS (1985); Sakai et al., "Enhanced Secretion of Human Nerve Growth Factor from *Saccharomyces cerevisiae* Using an Advanced δ-Integration System," *Biotechnol.* 9:1382-5 (1991), which are hereby incorporated by reference in their entirety). Some vectors have an origin of replication, which functions in the selected host cell. Suitable origins of replication include 2μ, ARS1, and 25 μM. The vectors have restriction endonuclease sites for insertion of the fusion gene and promoter sequences, and selection markers. The vectors may be modified by removal or addition of restriction sites, or removal of other unwanted nucleotides.

The isolated nucleic acid molecule of the present invention can be placed under the control of any promoter (Stetler et al., "Secretion of Active, Full- and Half-length Human Secretory Leukocyte Protease Inhibitor by *Saccharomyces cerevisiae*," *Biotechnol.* 7:55-60 (1989), which is hereby incorporated by reference in its entirety). One can choose a constitutive or regulated yeast promoter. Suitable promoter sequences for yeast vectors include, among others, promoters for metallothionein, 3-phosphoglycerate kinase (Hitzeman et al., "Isolation and Characterization of the Yeast 3-Phosphoglycerokinase Gene (PGK) by an Immunological Screening Technique," *J. Biol. Chem.* 255(24):12073-80 (1980), which is hereby incorporated by reference in its entirety), or other glycolytic enzymes (Hess et al., "Cooperation of Glycolytic Enzymes," *Adv. Enzyme Reg.* 7:149-67 (1969); Holland & Holland, "Isolation and Identification of Yeast Messenger Ribonucleic Acids Coding for Enolase, Glyceraldehyde-3-phosphate Dehydrogenase, and Phosphoglycerate Kinase," *Biochem.* 17(23):4900-7 (1978), which are hereby incorporated by reference in their entirety), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in European Patent Application Publication No. EP 0 073,657 to Genentech, Inc., which is hereby incorporated by reference in its entirety. Another alternative is the glucose-repressible ADH2 promoter described by Russell et al., "Nucleotide Sequence of the Yeast Alcohol Dehydrogenase II Gene," *J. Biol. Chem.* 258(4):2674-82 (1983), which is hereby incorporated by reference in its entirety, and Beier & Young, "Characterization of a Regulatory Region Upstream of the ADR2 Locus of *S. cerevisiae*," *Nature* 300(5894):724-8 (1982), which is hereby incorporated by reference in its entirety.

The strong promoters of e.g., phosphoglycerate kinase gene, other genes encoding glycolytic enzymes, and the α-factor gene, are constitutive. When a constitutive promoter is used, the product is synthesized during cell growth. The ADH2 promoter is regulated with ethanol and glucose, the GAL-1-10 and GAL7 promoters with galactose and glucose, the PHO5 promoter with phosphate, and the metallothionine promoter with copper. The heat shock promoters, to which the HSP150 promoter belongs, are regulated by temperature. Hybrid promoters can also be used. A regulated promoter is used when continuous expression of the desired product is harmful for the host cells. Instead of yeast promoters, a strong prokaryotic promoter such as the T7 promoter can be used, but in this case the yeast strain has to be transformed with a gene encoding the respective polymerase. For transcription termination, the HSP150 terminator or any other functional terminator is used. Here, promoters and terminators are called control elements. The present invention is not restricted to any specific vector, promoter, or terminator.

The vector may also carry a selectable marker. Selectable markers are often antibiotic resistance genes or genes capable of complementing strains of yeast having well characterized metabolic deficiencies, such as tryptophan or histidine deficient mutants. Preferred selectable markers include URA3, LEU2, HIS3, TRP1, HIS4, ARG4, and antibiotic resistance genes.

The vector may also have an origin of replication capable of replication in a bacterial cell. Manipulation of vectors is more efficient in bacterial strains. Preferred bacterial origin of replications are ColE1, Ori, or oriT.

Preferably, the mutant phytase encoded by the isolated nucleic acid molecule of the present invention is secreted by the cell into growth media. This allows for higher expression levels and easier isolation of the product. The mutant phytase is coupled to a signal sequence capable of directing the protein out of the cell. Preferably, the signal sequence is cleaved from the protein.

A leader sequence either from the yeast or from phytase genes or other sources can be used to support the secretion of expressed mutant phytase enzyme into the medium. The present invention is not restricted to any specific type of leader sequence or signal peptide.

Suitable leader sequences include the yeast α-factor leader sequence, which may be employed to direct secretion of the mutant phytase. The α-factor leader sequence is often inserted between the promoter sequence and the structural gene sequence (Kurjan & Herskowitz, "Structure of a Yeast Pheromone Gene (MF α): A Putative α-Factor Precursor Contains Four Tandem Copies of Mature α-Factor," Cell 30(3):933-43 (1982); Bitter et al., "Secretion of Foreign Proteins from Saccharomyces cerevisiae Directed by α-Factor Gene Fusions," Proc. Nat'l Acad. Sci. USA 81(17):5330-4 (1984); U.S. Pat. No. 4,546,082 to Kurjan et al.; European Patent Application Publication No. EP 0 324,274 to Chiron Corp., which are hereby incorporated by reference in their entirety). Another suitable leader sequence is the S. cerevisiae MFα1 (α-factor) which is synthesized as a prepro form of 165 amino acids comprising a signal or prepeptide of 19 amino acids followed by a "leader" or propeptide of 64 amino acids, encompassing three N-linked glycosylation sites followed by (LysArg(Asp/Glu, Ala)2-3 α-factor)4 (Kurjan & Herskowitz, "Structure of a Yeast Pheromone Gene (MF α): A Putative α-Factor Precursor Contains Four Tandem Copies of Mature α-Factor," Cell 30(3):933-43 (1982), which is hereby incorporated by reference in its entirety). The signal-leader part of the prepro MFα1 has been widely employed to obtain synthesis and secretion of heterologous proteins in S. cerivisiae. Use of signal/leader peptides homologous to yeast is known from: U.S. Pat. No. 4,546,082 to Kurjan et al.; European Patent Application Publication Nos. EP 0 116,201 to Chiron Corp., EP 0 123,294 to Amgen, EP 0 123,544 to Genentech Inc., EP 0 163,529 to Novo Industri, EP 0 123,289 to Chiron Corp.; and German Patent Application No. DK 3614/83, which are hereby incorporated by reference in their entirety. In European Patent Application Publication No. EP 0 123,289 to Chiron Corp., which is hereby incorporated by reference in its entirety, utilization of the S. cerevisiae α-factor precursor is described whereas International Patent Application Publication No. WO 84/01153 to Collaborative Research, Inc., which is hereby incorporated by reference in its entirety, indicates utilization of the S. cerevisiae invertase signal peptide, and German Patent Application No. DK 3614/83, which is hereby incorporated by reference in its entirety, indicates utilization of the S. cerevisiae PH05 signal peptide for secretion of foreign proteins.

The α-factor signal-leader from S. cerevisiae (MFα1 or MFα2) may also be utilized in the secretion process of expressed heterologous proteins in yeast (U.S. Pat. No. 4,546,082 to Kurjan et al.; European Patent Application Publication Nos. EP 0 116,201 to Chiron Corp., EP 0 123,294 to Amgen, EP 0 123,544 to Genentech Inc., EP 0 163,529 to Novo Industri, which are hereby incorporated by reference in their entirety). By fusing a DNA sequence encoding the S. cerevisiae MFα1 signal/leader sequence at the 5' end of the gene for the desired protein, secretion and processing of the desired protein was demonstrated. The use of the mouse salivary amylase signal peptide (or a mutant thereof) to provide secretion of heterologous proteins expressed in yeast has been described in International Patent Application Publication Nos. WO 89/02463 to Novo Industri and WO 90/10075 to Novo Nordisk, which are hereby incorporated by reference in their entirety.

U.S. Pat. No. 5,726,038 to Christiansen et al., which is hereby incorporated by reference in its entirety, describes the use of the signal peptide of the yeast aspartic protease 3, which is capable of providing improved secretion of proteins expressed in yeast. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., "Transformation of Yeast," Proc. Nat'l Acad. Sci. USA 75(4): 1929-33 (1978), which is hereby incorporated by reference in its entirety. The Hinnen et al. protocol selects for Trp transformants in a selective medium, where the selective medium consists of 0.67% yeast nitrogen base, 0.5% casamino acids, 2% glucose, 10 µg/ml adenine, and 20 µg/ml uracil.

The isolated nucleic acid molecule of the present invention may be maintained in a stable expression vector, an artificial chromosome, or by integration into the yeast host cell chromosome. Integration into the chromosome may be accomplished by cloning the mutant phytase gene into a vector which will recombine into a yeast chromosome. Suitable vectors may include nucleotide sequences which are homologous to nucleotide sequences in the yeast chromosome. Alternatively, the mutant phytase gene may be located between recombination sites, such as transposable elements, which can mobilize the gene into the chromosome.

The present invention also relates to isolated proteins or polypeptides having phytase activity. In one embodiment, the protein or polypeptide includes an amino acid sequence having at least 90 percent (preferably 96 percent) sequence identity to SEQ ID NO: 2 over a region of at least 100 amino acid residues, and includes at least one substitution of at least one amino acid residue corresponding to residue 58, 65, 112, 131, 149, 191, 195, and/or 271 of SEQ ID NO: 2, and, optionally, further includes at least one substitution of at least one amino acid residue corresponding to residue 228 and/or 300 of SEQ ID NO: 2. In another embodiment, the protein or polypeptide includes an amino acid sequence having at least 90 percent (preferably 96 percent) sequence identity to SEQ ID NO: 4 over a region of at least 100 amino acid residues, and containing at least one substitution of at least one amino acid residue selected from the group consisting of residues A205 and G277 of SEQ ID NO: 4.

Specific suitable amino acid substitutions are as already described herein (see above). The isolated mutant phytase can be in pure or non-pure form. The isolated protein or polypeptide can also be recombinant.

An isolated protein or polypeptide of the present invention can be obtained by several methods. The isolated protein or polypeptide of the present invention is preferably produced in pure form (preferably at least about 80%, more preferably 90%, pure) by conventional techniques well known in the art. Typically, the isolated protein or polypeptide of the mutant phytase of the present invention is secreted into the growth medium of recombinant host cells. Alternatively, the isolated protein or polypeptide of the present invention is produced but not secreted into growth medium. In such cases, to isolate the protein or polypeptide of the mutant phytase, the host cell carrying a recombinant plasmid is propagated, lysed by sonication, heat, or chemical treatment, and the homogenate is centrifuged to remove cell debris. The supernatant is then subjected to sequential ammonium sulfate precipitation. The fraction containing the protein or polypeptide of the present invention is subjected to gel filtration in an appropriately sized dextran or polyacrylamide column to separate the proteins. If necessary, the protein fraction (containing the mutant phytase of the present invention) may be further purified by HPLC.

The present invention also relates to an animal feed composition. The animal feed composition can contain the isolated protein or polypeptide of the present invention. The present invention further relates to a foodstuff containing the animal feed composition. The foodstuff can further contain greater than 1.0 percent by weight of a vitamin and mineral mix. The foodstuff can also further include soybean meal. The foodstuff can still further include antibiotics.

The protein or polypeptide of this invention can be used in an animal feed composition to improve the digestion of phosphate by various "animals" (as defined below). The present invention would decrease the need for supplementing animal feed with large amounts of inorganic phosphate, resulting in a less expensive form of animal feed and one that is less concentrated with the non-renewable form of phosphate. Since the present invention enhances the ability of simple-stomached animals to absorb phosphate, the fecal waste of these animals will contain less unutilized phytate-phosphate, which decreases the amount of phosphate pollution.

As used herein, the term "animals" includes domestic and non-domestic animals, and includes, without limitation, fowl species, porcine species, aquatic species, canine species, feline species, and humans. Other suitable animals that are encompassed by the term "animals" include, without limitation, mammalian species such as an *Oyctolagus* species, a *Capra* species, a *Bos* species, an *Equus* species, and/or an *Ovis* species. Further, all physiological stages (infant, juvenile, adult) of a particular species described herein are meant to be encompassed by the scope of the present invention. Thus, the term "animals" includes such simple-stomached animals as poultry, swine, pre-ruminant calves, zoo animals, and pets (e.g., cats and dogs).

In making the animal feed composition of the present invention, the mutant phytase is combined with a raw plant material and then processed into a pellet or powder form. The raw plant material may include various combinations of a number of plants and/or plant by-products commonly used in animal feed, including plants such as maize, soybean, wheat, rice, cotton seed, rapeseed, sorghum, and potato. In addition, the animal feed composition may be fortified with various vitamins, minerals, animal protein, and antibiotics. One embodiment of the animal feed composition includes a mixture of appropriate concentrations of the mutant phytase, an energy source(s) (e.g., maize, wheat), a protein source(s) (e.g., soybean, rice, cottonseed meal, rapeseed meal, sorghum meal), and vitamin/mineral supplements. In particular, the amount of the mutant phytase can be between about 100 to about 2,000 Units/kg of feed. In another embodiment, the amount of the mutant phytase can be between about 200 to about 1,500 Units/kg of feed. In yet another embodiment, the amount of the mutant phytase can be between about 300 to about 1,000 Units/kg of feed. One example of a typical animal feed composition would include 50-70% maize, 20-30% soybean, approximately 1% vitamin and mineral supplements, and an appropriate amount of mutant phytase.

In addition, the mutant phytase of the present invention could be used to enhance human nutrition, particularly by increasing the uptake of such minerals as zinc and iron. By adding the mutant phytase to the diets of humans, various problems arising from nutrient deficiencies, such as stunted growth and mental retardation in children, could be treated and avoided.

The present invention also relates to a method of feeding a monogastric animal. This method involves feeding to the animal a foodstuff in combination with the isolated mutant phytase of the present invention. Suitable animals can include, without limitation, the monogastric animals described above. In one embodiment, the animal is fed the foodstuff in combination with between about 100 and about 2,000 units of the phytase expressed in yeast per kilogram of the foodstuff. In another embodiment, the animal is fed the foodstuff in combination with between about 200 and about 1,500 units of the phytase expressed in yeast per kilogram of the foodstuff. In yet another embodiment, the animal is fed the foodstuff in combination with between about 300 and about 1,000 units of the phytase expressed in yeast per kilogram of the foodstuff.

The present invention also relates to a method of improving the nutritional value of a foodstuff consumed by an animal. This method involves providing a foodstuff containing myo-inositol hexakisphosphate, and also providing a mutant phytase of the present invention. The animal is then fed the foodstuff in combination with the mutant phytase under conditions effective to increase the bioavailability of phosphate from phytate. Suitable animals are as described above. The animal can also be a human. In one embodiment, the foodstuff can be pig feed. In another embodiment, the foodstuff can be poultry feed. In one embodiment, the animal is fed the foodstuff in combination with between about 100 and about 2,000 units of the phytase expressed in yeast per kilogram of the foodstuff. In another embodiment, the animal is fed the foodstuff in combination with between about 200 and about 1,500 units of the phytase expressed in yeast per kilogram of the foodstuff. In yet another embodiment, the animal is fed the foodstuff in combination with between about 300 and about 1,000 units of the phytase expressed in yeast per kilogram of the foodstuff.

The present invention also relates to a method for producing an improved phytase protein or polypeptide. This method involves providing a nucleic acid sequence encoding a phytase protein or polypeptide having an amino acid sequence of at least 90 percent sequence identity to SEQ ID NO: 2, and altering the nucleic acid sequence under conditions effective to yield a nucleic acid sequence encoding an improved phytase protein or polypeptide.

The improved phytase protein or polypeptide includes an amino acid sequence having at least 90 percent (preferably 96 percent) sequence identity to SEQ ID NO: 2 over a region of at least 100 amino acid residues and containing at least one substitution of at least one amino acid residue selected from the group consisting of residues A58, P65, K112, F131, S149, Q191, K195, and T271 of SEQ ID NO: 2, and may further include substitution of residue E228 and/or K300. Suitable specific substitutions can include those already described above.

Improved phytase protein or polypeptide refers to mutant phytases that have a higher heat tolerance and/or better pH profile compared with the heat tolerance and/or pH profile of the phytase protein or polypeptide which has not been altered (e.g., wild type).

Nucleic acid molecules may be altered by means that will be apparent to one of ordinary skill in the art. For example, site-directed mutagenesis may be carried out to alter the nucleic acid molecule, and the improved protein or polypeptide expressed recombinantly.

The present invention also relates to a method of in vitro hydrolysis of phytate. This method involves providing an isolated protein or polypeptide of the present invention. The isolated protein or polypeptide is combined with a phytate source under conditions effective to increase the bioavailability of phosphate from the phytate source. A suitable phytate source can be, without limitation, an animal feed and/or a foodstuff. The method can further involve combining the mutant phytase with a phytate source under conditions effective to increase the bioavailability of various minerals such as, including, without limitation, calcium, zinc, and/or iron, from the phytate source.

The present invention also relates to a method of improving the nutritional value of a foodstuff consumed by humans. This method involves providing a mutant phytase according to the present invention. The mutant phytase is combined with a foodstuff consumed by humans under conditions effective to increase the bioavailability of minerals from the foodstuff. Suitable minerals can include, without limitation, iron, zinc, phosphorus, and calcium.

The present invention further relates to a method of imparting improved mineral nutritional value to a plant that is edible for consumption by animals. This method involves providing a transgene containing an isolated nucleic acid molecule of the present invention. The isolated nucleic acid molecule is operatively associated with a regulatory sequence containing transcriptional and translational regulatory elements that control expression of the isolated nucleic acid molecule in a transgenic plant cell. The method also involves providing a non-transformed plant that is edible for consumption by animals. The transgene is inserted into the genome of the non-transformed plant under conditions effective to yield a transformed plant that transgenically expresses a mutant phytase encoded by the isolated nucleic acid molecule of the present invention. The resulting transformed plant has improved mineral nutritional value compared to that of the non-transformed plant.

In order to transgenically express the mutant phytase of the present invention in plants, transgenic plants carrying the isolated nucleic acid molecule of the present invention are produced by transforming a plant with a transgene (e.g., a chimeric DNA) construct that expresses the mutant phytase.

In order to express the mutant phytase from the trangene, the construct should include a plant specific promoter. The promoter should ensure that the foreign gene is expressed in the plant. The promoter can be chosen so that the expression occurs only in specified tissues, at a determined time point in the plant's development or at a time point determined by outside influences. The promoter can be homologous or heterologous to the plant. Suitable promoters include, e.g., the RUBISCO small subunit promoter, tissue-specific promoters, the promoter of the 35S RNA of the cauliflower mosaic virus (U.S. Pat. No. 5,034,322 to Rogers et al., which is hereby incorporated by reference in its entirety), the enhanced 35S promoter (U.S. Pat. No. 5,106,739 to Comai et al., which is hereby incorporated by reference in its entirety), the dual S35 promoter, the FMV promoter from figwort mosaic virus (U.S. Pat. No. 5,378,619 to Rogers, which is hereby incorporated by reference in its entirety), the RI T-DNA promoter (U.S. Pat. No. 5,466,792 to Slightom et al., which is hereby incorporated by reference in its entirety), the octopine T-DNA promoter (U.S. Pat. No. 5,428,147 Barker et al., which is hereby incorporated by reference in its entirety), the alcohol dehydrogenase 1 promoter (Callis et al., "Introns Increase Gene Expression in Cultured Maize Cells," *Genes Dev.* 1(10): 1183-200 (1987), which is hereby incorporated by reference in its entirety), the patatin promoter B33 (Rocha-Sosa et al., "Both Developmental and Metabolic Signals Activate the Promoter of a Class I Patatin Gene," *EMBO J.* 8(1):23-9 (1989), which is hereby incorporated by reference in its entirety), the E8 promoter (Deikman & Fischer, "Interaction of a DNA Binding Factor with the 5'-Flanking Region of an Ethylene-responsive Fruit Ripening Gene from Tomato," *EMBO J.* 7(11):3315-20 (1988), which is hereby incorporated by reference in its entirety), the beta-conglycin promoter (Tierney et al., "Isolation and Characterization of a Genomic Clone Encoding the β-Subunit of β-Conglycinin," *Planta* 172(3):356-63 (1987), which is hereby incorporated by reference in its entirety), the acid chitinase promoter (Samac et al., "Isolation and Characterization of the Genes Encoding Basic and Acidic Chitinase in *Arabidopsis thaliana*," *Plant Physiol.* 93(3):907-14 (1990), which is hereby incorporated by reference in its entirety), the *Arabidopsis* histone H4 promoter (U.S. Pat. No. 5,491,288 to Chaubet et al., which is hereby incorporated by reference in its entirety), or the recombinant promoter for expression of genes in monocots (U.S. Pat. No. 5,290,924 to Last et al., which is hereby incorporated by reference in its entirety).

Preferred promoters include the RUBISCO small subunit promoter, the 35S promoters, fiber enhanced promoters, vascular cell enhanced promoters, stem cell enhanced promoters, or seed enhanced promoters. Such promoters may ensure expression in a tissue specific or tissue-enhanced manner, but may allow expression in other cell types. For example it may ensure enhanced expression in photosynthetically active tissues (RUBISCO (Worrell et al., "Expression of a Maize Sucrose Phosphate Synthase in Tomato Alters Leaf Carbohydrate Partitioning," *Plant Cell* 3(10): 1121-30 (1991), which is hereby incorporated by reference in its entirety)) or other mesophyll-cell-specific promoters (Datta et al., "Constitutive and Tissue-specific Differential Expression of the CryIA(b) Gene in Transgenic Rice Plants Conferring Resistance to Rice Insect Pest," *Theor. Appl. Genet.* 97:20-30 (1998), which is hereby incorporated by reference in its entirety). Other promoters can be used that ensure expression only in specified organs, such as the leaf, root, tuber, seed, stem, flower or specified cell types such as parenchyma, epidermal, or vascular cells. One example of a tissue-specific promoter is the RB7 promoter that is root specific (U.S. Pat. No. 5,459,252 to Conkling et al., which is hereby incorporated by reference in its entirety). Such promoters may be used either alone or in combination to optimize over-expression in the most desirable set of tissues or organs.

In one embodiment of the present invention, the transgene is stably integrated into the genome of the non-transformed plant. When a plant is transformed by *Agrobacterium* mediated transformation, a portion of the Ti plasmid integrates into the plant genome and is stably passed on to future generations of plant cells.

Numerous methods exist for transforming plant cells. The preferred methods include electroporation, *Agrobacterium* mediated transformation, biolistic gene transformation, chemically mediated transformation, or microinjection.

The vector described above can be microinjected directly into plant cells by use of micropipettes to transfer mechanically the recombinant DNA (Crossway et al., "Integration of Foreign DNA Following Microinjection of Tobacco Mesophyll Protoplasts," *Mol. Gen. Genetics* 202(2):179-85 (1986), which is hereby incorporated by reference in its entirety). The genetic material may also be transferred into the plant cell using polyethylene glycol (Krens et al., "In vitro Transformation of Plant Protoplasts with Ti-plasmid DNA," *Nature* 296: 72-4 (1982), which is hereby incorporated by reference in its entirety).

Another approach to transforming plant cells with an isolated nucleic acid molecule of the present invention is particle bombardment (also known as biolistic transformation) of the host cell. This can be accomplished in one of several ways. The first involves propelling inert or biologically active particles at cells. This technique is disclosed in U.S. Pat. Nos. 4,945,050, 5,036,006, and 5,100,792, all to Sanford et al., which are hereby incorporated by reference in their entirety. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells.

Yet another method of introduction is fusion of protoplasts with other entities, either minicells, cells, lysosomes or other fusible lipid-surfaced bodies (Fraley et al., "Liposome-mediated Delivery of Tobacco Mosaic Virus RNA into Tobacco Protoplasts: A Sensitive Assay for Monitoring Liposome-protoplast Interactions," *Proc. Nat'l Acad. Sci. USA* 79(6): 1859-63 (1982), which is hereby incorporated by reference in its entirety).

The isolated nucleic acid molecule may also be introduced into the plant cells by electroporation (Fromm et al., "Expression of Genes Transferred into Monocot and Dicot Plant Cells by Electroporation," *Proc. Nat'l Acad. Sci. USA* 82(17):5824-8 (1985), which is hereby incorporated by reference in its entirety). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate.

Another method of introducing the isolated nucleic acid molecule of the present invention into plant cells is to infect a plant cell with *Agrobacterium tumefaciens* or *A. rhizogenes* previously transformed with the isolated nucleic acid molecule. Under appropriate conditions known in the art, the transformed plant cells are grown to form shoots or roots, and develop further into plants. Generally, this procedure involves inoculating the plant tissue with a suspension of bacteria and incubating the tissue for 48 to 72 hours on regeneration medium without antibiotics at 25-28° C.

*Agrobacterium* is a representative genus of the gram-negative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences can be introduced into appropriate plant cells by means of the Ti plasmid of *A. tumefaciens* or the Ri plasmid of *A. rhizogenes*. The Ti or Ri plasmid is transmitted to plant cells on infection by *Agrobacterium* and is stably integrated into the plant genome (Schell, "Transgenic Plants as Tools to Study the Molecular Organization of Plant Genes," *Science* 237(4819):1176-83 (1987), which is hereby incorporated by reference in its entirety).

After transformation, whole transformed plants can be recovered. If transformed seeds were produced directly, these can be selected by germination on selection medium and grown into plants (Clough & Bent, "Floral Dip: A Simplified Method for *Agrobacterium*-mediated Transformation of *Arabidopsis thaliana*," *Plant J.* 16(6):735-43 (1998), which is hereby incorporated by reference in its entirety). If transformed pollen was produced directly, this can be used for in vivo pollination followed by selection of transformed seeds (Touraev et al., "Plant Male Germ Line Transformation," *Plant J.* 12(4):949-56 (1997), which is hereby incorporated by reference in its entirety). If meristems were transformed, these can be grown into plants in culture then transferred to soil (Gould et al., "Regeneration of *Gossypium hirsutum* and *G. barbadense* from Shoot Apex Tissues for Transformation," *Plant Cell Rep.* 10(1): 12-16 (1991), which is hereby incorporated by reference in its entirety).

If protoplasts or explants were transformed, plants can be regenerated. Plant regeneration from cultured protoplasts is described in DAVID EVANS ET AL., 1 HANDBOOK OF PLANT CELL CULTURE (1983); I CELL CULTURE AND SOMATIC CELL GENETICS OF PLANTS (Indra K. Vasil ed., 1984); and III CELL CULTURE AND SOMATIC CELL GENETICS OF PLANTS (Indra K. Vasil ed., 1986), which are hereby incorporated by reference in their entirety. Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

It is known that practically all plants can be regenerated from cultured cells or tissues, including but not limited to, species of sugarcane, sugar beets, cotton, forest trees, forage crops, and fiber producing plants. Regeneration is also possible in seed-producing plants including, but not limited to, maize, rice, wheat, soybean, rape, sunflower, and peanut.

After the expression cassette is stably incorporated in transgenic plants, it can be transferred to other plants by sexual crossing. Any of a number of standard breeding techniques can be used, depending upon the species to be crossed.

Once transgenic plants of this type are produced, the plants themselves can be cultivated in accordance with conventional procedures with the presence of the isolated nucleic acid molecule encoding a mutant phytase of the present invention. Alternatively, transgenic seeds are recovered from the transgenic plants. These seeds can then be planted in the soil and cultivated using conventional procedures to produce transgenic plants.

The isolated protein or polypeptides of the present invention may also be useful to produce specific inositol phosphate metabolites or products for nutritional and biomedical applications.

The present invention may be further illustrated by reference to the following examples.

EXAMPLES

Example 1

Media and Reagents

Bacterial and yeast strains, plasmids, and primers used in Examples 1-14 are listed in Table 2. *Escherichia coli* DH5α was cultured at 37° C. in LB medium. *Pichia pastoris* X33 was cultured at 30° C. in either YPD medium or BMGY/BMMY medium (Invitrogen, San Diego, Calif.). Zeocin (Invitrogen, San Diego, Calif.) was added at 100 μg ml$^{-1}$ YPD medium or BMGY/BMMY medium for yeast and 25 ug ml$^{-1}$ LB medium for *E. coli*. Restriction enzymes were obtained from Promega (Madison, Wis.). Oligonucleotides were synthesized at MWGbiotech (High Point, N.C.). Phytic acid (inositol hexaphosphoric acid) dodecasodium salt from rice (p-3138), ammonium molybdate tetrahydrate (A-7302), and L-ascorbic acid (A-0278) were purchased from Sigma (St. Louis, Mo.). Sulfuric acid (A300-212) and trichloroacetic acid (A322) were purchased from Fisher (Pittsburgh, Pa.). Automatic DNA sequencing was performed at Cornell Biotechnology Center.

TABLE 2

| Strains, plasmids and synthetic oligonucleotides | | |
|---|---|---|
| Strains and plasmids | Relevant genotypes | Reference |
| Strains | | |
| DH5α | *E. coli* strain, a-complimentation | Stratagene |
| *P. pastoris* X33 | protein expression host | Invitrogen |
| Plasmids | | |
| pPICZα | ColE1 ori, ZeoR, for integration in *P. pastoris* | Invitrogen |
| pGAPZα | ColE1 ori, ZeoR, for integration in *P. pastoris* | Invitrogen |
| pPICZα-afp | afp fragment cloned into EcoRI and XbaI sites of pPICZα | Invitrogen |
| pGAPZα-phyA | phyA fragment cloned between EcoRI and XbaI sites of pGAPZα | Invitrogen |
| pafp E35A | E35A substitution of afp in pPICZα-afp | Examples 1-14 |
| pafpR168A | R168A substitution of afp in pPICZα-afp | Examples 1-14 |
| pafpR248A | R248A substitution of afp in pPICZα-afp | Examples 1-14 |
| pafpE35A/R168A | E35A/R168A substitution of afp in pPICZα-afp | Examples 1-14 |
| pafpE35A/R248A | E35A/R248A substitution of afp in pPICZα-afp | Examples 1-14 |
| pafpR168A/R248A | R168A/R248A substitution of afp in pPICZα-afp | Examples 1-14 |
| pafpE35A/R168A/R248A | E35A/R168A/R248A substitution of afp in pPICZα-afp | Examples 1-14 |
| pphyAA58E | A58E substitution of phyA in pGAPZα-phyA | Examples 1-14 |
| pphyAQ191R | Q191R substitution of phyA in pGAPZα-phyA | Examples 1-14 |
| pphyAT271R | T271R substitution of phyA in pGAPZα-phyA | Examples 1-14 |

TABLE 2-continued

Strains, plasmids and synthetic oligonucleotides

| | | |
|---|---|---|
| pphyA A58E/Q191R | A58E/Q191R substitution of phyA in pGAPZα-phyA | Examples 1-14 |
| pphyA A58E/T271R | A58E/T271R substitution of phyA in pGAPZα-phyA | Examples 1-14 |
| pphyA Q191R/T271R | Q191R/T271R substitution of phyA in pGAPZα-phyA | Examples 1-14 |
| pphyA A58E/Q191R/T271R | A58E/Q191R/T271R substitution of phyA in pGAPZα-phyA | Examples 1-14 |
| pphyA A58E/P65S | A58E/P65S substitution of phyA in pGAPZα-phyA | Examples 1-14 |
| pphyA A58E/p65S/Q191R/T271R | A58E/p65S/Q191R/T271R substitution of phyA in pGAPZα-phyA | Examples 1-14 |
| Oligonucleotides | | |
| afp-F2 | 5'-GGATTTCGATGTTGCTGTTTTG-3' (SEQ ID NO: 5) | |
| afp-M1(E35A) | 5'-CAGCTCGTC<u>CGC</u>GAGCGAAAAG-3' (SEQ ID NO: 6) | |
| afp-M2(R168A) | 5'-GCGACGAAC<u>GCC</u>GCCGCTCCG-3' (SEQ ID NO: 7) | |
| afp-M3(R248A) | 5'-ACGGTAGCG<u>GCC</u>ACCAGCGAC-3' (SEQ ID NO: 8) | |
| afp-R2 | 5'-GTCGAGTTAGTGCTGGTGTGGT-3' (SEQ ID NO: 9) | |
| phyA-F | 5'-CGGAATTCCTGGCAGTCCCCGCCT-3' (SEQ ID NO: 10) | |
| phyA-A58E | 5'-ACCGATTCGTTTTCCAGAGAGAAGA-3' (SEQ ID NO: 11) | |
| phyA-P65S | 5'-GCGGGCACCTC<u>AGA</u>GGAGATGACC-3' (SEQ ID NO: 12) | |
| phyA-Q191R | 5'-TTGGGCGACGAT<u>CG</u>GCCGGGCTGGG-3' (SEQ ID NO: 13) | |
| phyA-T271R | 5'-ACACCATCTCC<u>AGA</u>AGCACCGTCGA-3' (SEQ ID NO: 14) | |
| phyA-R | 5'-GCTCTAGACTAAGCAAAACACTCC-3' (SEQ ID NO: 15) | |

Example 2

Rational Design of Mutations

To assess the contributions of E35, R168, and R248 involved in hydrogen bonding and ionic interactions to the thermostability of Afp, site-directed mutagenesis was used to substitute each of these three residues with alanine so they would no longer participate in the predicted interactions. A total of 7 mutants were constructed, including three single-substitution mutants (Afp-E35A, Afp-R168A, and Afp-R248A), three double-substitution mutants (Afp-E35A/R168A, Afp-R168A/R248A, and Afp-E35A/R248A), and one triple-substitution mutant (Afp-E35A/R168A/R248A).

To test whether the thermostability of PhyA could be improved by adopting the putative hydrogen bonding and ionic interactions of Afp, residues A58, P65, Q191, and T271 of PhyA were substituted with the corresponding Afp residues (Glu, Ser, Arg, and Arg, respectively). Pro65 of PhyA was changed to Ser in order to form a hydrogen bonding network with Glu58 as in the corresponding position of Afp, a serine residue that forms a hydrogen bond with Glu35 (Xiang et al., "Crystal Structure of a Heat-resilient Phytase from Aspergillus fumigatus, Carrying a Phosphorylated Histidine," *J. Mol. Biol.* 339:437-45 (2004), which is hereby incorporated by references in its entirety). A total of 9 mutants were constructed, including three single-substitution mutants (PhyA-A58E, PhyA-Q191R, and PhyA-T271R), four double-substitution mutants (PhyA-A58E/Q191R, PhyA-A58E/T271R, PhyA-Q191R/T271R, and PhyA-A58E/P65S), one triple-substitution mutant (PhyA-A58E/Q191R/T271R), and one multi-substitution mutant (PhyA-A58E/P65S/Q191R/T271R), as set forth in Table 2.

Example 3

Site-Directed Mutagenesis

Site-directed mutagenesis of *A. fumigatus* afp and of *A. niger* phyA genes was conducted using mega-primer polymerase chain reaction ("PCR") mutagenesis. Briefly, DNA fragments containing the desired point mutations were produced in two sequential PCR. The first reaction used a 22-25 nucleotide primer containing a single nucleotide alteration (Table 2) and a 22-25 nucleotide reverse primer. The resulting PCR products were size-fractionated using 1.5% agarose gel and purified using QIAquick gel extraction kit (Qiagen, Valencia, Calif.). These PCR fragments were then used as mega-primers in a second PCR, along with a forward primer. These second PCR products were then digested at each end by two restriction enzymes and introduced into the wild type template to replace the corresponding wild type gene fragments. The double and triple mutations were generated by splicing the template containing the single mutations after restriction enzyme digestions and combining the mutations together. Plasmids containing the mutations were verified by automated DNA sequencing at Cornell Biotechnology Center.

Example 4

Protein Expression

*Pichia pastoris* X33 was used as an expression host. *A. fumigatus* phytase gene and seven mutants were cloned in pPICZα vector and transformed into *P. pastoris* X33 by electrophoresis with an ECM600 Electro Cell Manipulator (Gentronics, Inc., BTX Instrument Division, San Diego, Calif.). Individual transformants were grown in BMGY medium for one day before transferring to BMMY inducible medium. Cells were grown at 28° C. for up to 144 hours with aeration (220 rpm). Methanol was added as an inducer first after 24 hour culturing at a final concentration of 0.5%, and then after 48, 72, 96, 120, and 144 hours, respectively, to maintain a constant concentration of methanol. At each time point, 1 ml of culture was collected and centrifuged at 12,000 g for 30 minutes. Supernatants were saved at −20° C. for later analysis. The wild type PhyA gene and the nine mutants were cloned into pGAPZα vector and transformed onto *P. pastoris*. Individual transformants were grown in YPD expression medium with aeration (220 rpm) at 30° C. for 48 to 72 hours until $O.D._{600}$ value reached 20.

Example 5

Purification of the Expressed Phytases

Cultures of wild type and mutant Afp transformants were centrifuged at 12,000 g for 30 minutes to remove cell debris. After the supernatants were concentrated approximately 10-fold by Amicon centrifugal filter device (Centriplus YM-30, molecular weight cutoff 30,000, Fisher, Pittsburgh, Pa.) the expressed enzymes were purified by nickel-nitrilotriacetic ("Ni-NTA") metal-affinity chromatography (Qiagen). Appropriate amounts of Ni-NTA resin (10 μl resin for 50-100 μg 6×His-tagged protein) were added to the supernatant and mixed gently for 30 minutes. The resin was precipitated by centrifuging for 10 seconds at 15,000 g, and then washed twice with a washing buffer (50 mM $NaH_2PO_4$, 300 mM NaCl, 20 mM imidazole, adjusting pH to 8.0 with NaOH). Proteins were eluted 3 times by incubating the resin with an elution buffer (50 mM $NaH_2PO_4$, 300 mM NaCl, 250 mM imidazole, adjusting pH to 8.0 with NaOH).

After cultures of wild type and mutant PhyA transformants were centrifuged at 12,000 g for 30 minutes to remove cell debris, the supernatants were concentrated approximately 20-fold by ultrafiltration. The concentrate was subjected to DEAE cation-exchange chromatography (Sigma). DEAE column was balanced with 1000 ml of 10 mM Tris-HCl buffer (pH 7.4). The proteins were eluted with 300 ml of an elution buffer (10 mM Tris-HCl, pH 7.4) with a linear gradient of NaCl from 0 to 0.3 M. The flow-through fractions were collected by an automatic fraction collector. The fraction profiles of $OD_{280}$ and phytase activity were checked to determine the desired protein peaks. The peak fractions were pooled and concentrated down to less than 2 ml by Amicon centrifugal filter device and then loaded onto Sephadex100 sizing column (Sigma) previously equilibrated with 10 mM Tris-HCl buffer (pH 7.4) containing 0.15 M NaCl. Peak fractions were stored at −20° C. and used for further characterization.

Example 6

Biochemical Characterization of the Expressed Phytases

Phytase activity assays were conducted as described in Han et al., "Expression of an *Aspergillus niger* Phytase Gene (phyA) in *Saccharomyces cerevisiae*," *Appl. Environ. Microbiol.* 65:1915-8 (1999), which is hereby incorporated by reference in its entirety. The pH activity profile of phytase was determined at 37° C. using two different buffers, 0.2 M glycine-HCl buffer for pH 2.0-3.0 and 0.2 M citrate buffer for pH 3.5-6.5 (Han & Lei, "Role of Glycosylation in the Functional Expression of an *Aspergillus niger* Phytase (phyA) in *Pichia pastoris*," *Arch. Biochem. Biophys.* 364:83-90 (1999); Han et al., "Expression of an *Aspergillus niger* Phytase Gene (phyA) in *Saccharomyces cerevisiae*," *Appl. Environ. Microbiol.* 65:1915-8 (1999), which are hereby incorporated by reference in their entirety). The optimal temperature of the phytases was tested using 0.2 M citrate buffer at pH 5.5. Thermal stability of the phytases was tested using both the culture supernatants and purified phytase proteins. For supernatants, the samples were diluted with 0.2 M citrate buffer (pH 5.5) to 0.2 unit of phytase activity per ml. For purified proteins, the samples were diluted with 0.2 M citrate buffer (pH 5.5) to 10 μg of phytase protein per ml. Concentration of the purified proteins was determined by Lowry assay (Lowry et al., "Protein Measurement with the Folin Phenol Reagent," *J. Biol. Chem.* 193:265-75 (1951), which is hereby incorporated by reference in its entirety). The diluted samples were incubated for 10 minutes at each of the following temperatures: 50, 60, 70, 80, 90, and 100° C. Immediately after heat treatment, the samples were placed on ice for 30 minutes (Han & Lei, "Role of Glycosylation in the Functional Expression of an *Aspergillus niger* Phytase (phyA) in *Pichia pastoris*," *Arch. Biochem. Biophys.* 364:83-90 (1999); Han et al., "Expression of an *Aspergillus niger* Phytase Gene (phyA) in *Saccharomyces cerevisiae*," *Appl. Environ. Microbiol.* 65:1915-8 (1999), which are hereby incorporated by reference in their entirety). Phytase activity was measured at 37° C. and pH 5.5 as described above.

Example 7

Differential Scanning Calorimetry

Unfolding temperatures (Tm) of selected phytases were determined with DSC Q10 (TA Instruments, New Castle, Del.) differential scanning calorimeter equipped with refrigerated cooling system and Thermal Advantage™ for Q Series™ software. The purified wild type and mutant PhyA-A58E/P65S/Q191R/T271R proteins were concentrated to 50 mg/ml by freeze drying with a Jouan RC1010 speed vacuum in 50 mM Tris-HCl buffer, pH 7.4. After 8 mg of each protein sample was sealed in stainless steel cells and equilibrated at 10° C. followed by isothermaling for 2 minutes, the proteins were scanned from 30° C. to 100° C. at a heating rate of 2° C. per minute. Data were collected at a rate of 0.1 seconds per point.

Example 8

Kinetic Parameters, $K_m$ and $V_{max}$

Kinetic parameters, $K_m$ and $V_{max}$, of selected phytases were determined at both pH 3.5 and pH 5.5. Purified samples were diluted with 0.2 M citrate buffer (pH 3.5 or 5.5) to a final concentration of 0.1 unit of phytase activity ("U") per ml. Phytase activity assays were carried out using phytic acid dodecasodium salts as the substrate at 13 different concentrations (2.5, 5, 7.5, 10, 25, 50, 75, 100, 250, 500, 750, 1,000, and 2,500 µM). Four parallel series of phytase reactions were carried out with different phytase hydrolysis reaction times: 5, 10, 15, and 20 minutes. Data were analyzed as follows: i) a plot of phytase activity versus reaction time to calculate initial velocities (µmol/min); ii) a plot of initial velocities versus substrate concentrations ($V_0$ VS [S]); iii) a reciprocal plot of $V_0$ and [S] to make a Lineweaver-Burk plot and calculation of the $K_m$ and $V_{max}$, respectively.

Example 9

Hydrolysis of Phytate Phosphorus from Soybean Meal

The hydrolysis of phytate phosphorus from soybean meal was assayed by incubating wild type PhyA and mutants PhyA-A58E/Q191R, PhyA-A58E/Q191R/T271R, PhyA-A58E/P65S, and PhyA-A58E/P65S/Q191R/T271R with soybean meal at ratios of 250 U, 500 U, and 750 U phytase per kilogram soybean meal. The hydrolysis reaction was carried out at pH 5.5 or 3.5 at 37° C. for 1 hour. The released inorganic phosphorus was determined as described in Han et al., "Expression of an *Aspergillus niger* Phytase Gene (phyA) in *Saccharomyces cerevisiae*," *Appl. Environ. Microbiol.* 65:1915-8 (1999), which is hereby incorporated by reference in its entirety.

Example 10

Statistical Analysis

Data were analyzed by Minitab (Release 14, Minitab Inc., State College, Pa.). The Banferroni t test was used to compare mean differences. Significance was set at a P value of <0.05.

Example 11

Mutations in Residues E35, R168, and R248 of *A. fumigatus* Phytase Impair Protein Thermal Stability Each Afp mutant was tested for its thermal stability at various temperatures from 50 to 100° C. at 10° C. intervals. Each of the single and combined substitutions of residues E35, R168, R248 with alanine resulted in reduction in the thermostability of the enzymes at every temperature tested, as shown in FIGS. 1A-C. Among the three single mutants, Afp-E35A decreased (P<0.05) the enzyme thermostability after being heated at >70° C. The other two single mutants (Afp-R168A and Afp-R248A) showed decreases (P<0.05) at >90° C., as shown in FIG. 1A. Three double mutants showed lower (P<0.05) thermostability than that of the single mutants or wild type Afp at >60° C., as shown in FIG. 1B. Among the seven mutants, the triple mutant had the lowest thermostability with a 25% lower residual activity than wild type Afp after heat treatment at 100° C., as shown in FIG. 1C. The seven purified Afp mutants and the wild type enzyme exhibited similar specific activities (31.8 to 35.1 U/mg protein) and pH activity profiles with a pH optimum at 5.5, and shared the same optimal temperature (55° C.).

Example 12

Substitutions of A58E, P65S, Q191R, and T271R in PhyA Enhance its Enzyme Thermostability All the mutants plus wild type PhyA were subjected to a one-temperature thermal stability assay. Each enzyme was heated at 80° C. for 10 minutes and assayed for residual activity. Two double mutants, PhyA-A58E/Q191R and PhyA-A58E/P65S, one triple mutant, PhyA-A58E/Q191R/T271R, and one quadruple mutant, PhyA-A58E/P65S/Q191R/T271R, showed promising improvement in residual activity and were selected for further characterization. These four mutants and wild type PhyA were heated at different temperatures from (50° C. to 100° C.) for 10 minutes. Each of the four mutants showed greater residual activity (P<0.01) than that of wild type PhyA at temperatures above 80° C., as shown in FIG. 2A. The quadruple mutant showed the highest heat stability, with a 20% increase in residual activity over that of wild type PhyA after heat treatment at 100° C., as shown in FIGS. 2B-C, indicating that each substitution contributed positively and additively to the protein thermal stability. While the melting temperature for wild type PhyA was 66.3° C., as shown in FIG. 3A, the thermogram of the quadruple mutant showed transition midpoints at 71.5° C. and 73.8° C., respectively, as shown in FIG. 3B.

Example 13

Substitutions of A58E and P65S in PhyA Improve its Binding Affinity Toward Sodium Phytate The kinetic parameters ($K_m$ and $V_{max}$) for the hydrolysis of sodium phytate were determined for the thermostable mutants PhyA-A58E/Q191R, PhyA-A58E/Q191R/T271R, PhyA-A58E/P65S, PhyA-A58E/P65S/Q191R/T271R, and wild type PhyA. Steady-state kinetic measurements revealed that the apparent $K_m$ of wild type PhyA was 167.5 µM using sodium phytate as the substrate, as shown in Table 3. The apparent $K_m$ of mutants PhyA-A58E/P65S and PhyA-A58E/P65S/Q191R/T271R decreased by approximately 22% and 36%, respectively, compared to that of the wild type PhyA. In contrast, the wild type and the four mutants shared similar $V_{max}$ and specific activity. Likewise, these four mutants showed no shift in pH activity profile, optimal pH (2.5 and 5.5), and optimal temperature (55° C.) from that of the wild type.

TABLE 3

Specific activities and kinetic parameters of wild type PhyA and selected PhyA mutants at pH 5.5.

| Phytase | Specific activity (U/mg protein) | Vmax (µM/min) | Km (uM) |
| --- | --- | --- | --- |
| wild type PhyA | 80.9 ± 1.1 | 135.1 | 167.5 |
| phyA-A58E/Q191R | 82.2 ± 1.2 | 128.2 | 154.0 |
| phyA-A58E/Q191R/T271R | 83.8 ± 4.1 | 169.5 | 162.3 |
| phyA-A58E/P65S | 84.2 ± 3.4 | 109.9 | 130.4 |
| phyA-A58E/p65S/Q191R/T271R | 83.2 ± 2.1 | 117.6 | 106.4 |

Example 14

Substitutions of A58E, P65S, Q191R, and T271R in PhyA Elevate Hydrolysis of Phytate-Phosporus from Soybean Meal At pH 5.5, free inorganic phosphorus released from phytate in soybean meal by mutants PhyA-A58E/Q191R, PhyA- A58E/Q191R/T271R, PhyA-A58E/P65S, and PhyA-A58E/P65S/Q191R/T271R was greater (P<0.01) that that released by the wild type PhyA at 750 U and 1000 U per kilogram soybean meal, as shown in FIG. 4A. At pH 3.5, such differences became significant (P<0.01) at all tested ratios of phytase and soybean meal, as shown in FIG. 4B.

Discussion of Examples 1-14

Based on the crystal structure of Afp (Xiang et al., "Crystal Structure of a Heat-resilient Phytase from *Aspergillus fumigatus*, Carrying a Phosphorylated Histidine," *J. Mol. Biol.* 339:437-45 (2004), which is hereby incorporated by reference in its entirety), two strong hydrogen bonds with distances of 2.54 Å and 2.95 Å, respectively, can be formed between Glu35 and Ser42. This may help maintain the hydrogen bond network in the Glu35-Ser42 region, among which Asp36, Leu38, and Ser39 are also actively involved, as shown in FIG. 5A. As shown in FIG. 5B, the substitution of Glu35 with alanine in the Afp-E35A mutant disrupted the hydrogen bonding, resulting in lower thermal stability of Afp. In wild type Afp (Xiang et al., "Crystal Structure of a Heat-resilient Phytase from *Aspergillus fumigatus*, Carrying a Phosphorylated Histidine," *J. Mol. Biol.* 339:437-45 (2004), which is hereby incorporated by reference in its entirety), two arginine residues (Arg168 and Arg248) interact with Asp161 and Asp244, respectively, through salt bridges to form a C-terminal capping box structure, which is supposed to stabilize the helical conformation of oligopeptides. Specifically, Arg168 interacts with Asp161 through ionic interaction, and also forms a hydrogen bond with Asp161 with a distance of 2.68 Å, as shown in FIG. 5C. As expected, the substitution of arginine with alanine in the Afp-R168A mutant (FIG. 5D) disrupted these structures, lowering the enzyme thermostability. Similarly, Arg248 interacts with Asp244 through ionic interactions, and these two residues form two hydrogen bonds with distances of 2.90 Å and 2.92 Å, respectively, as shown in FIG. 5E. Clearly, as shown in FIG. 5F, the R248A substitution in mutants Afp-R248A, Afp-E35A/R248A, Afp-R168A/R248A, and Afp-E35A/R168A/R248A interrupted the hydrogen bond between the side chain of Arg248 and the carbonyl group of Asp244, causing a decreased thermostability in all these mutants. Overall, residues E35, R168, and R248 bear similar contributions to the thermostability of Afp. It is noteworthy that the deleterious effect of each single mutation was additive, as the triple mutant showed the least thermostability.

The loss of thermostability in Afp by disrupting selected hydrogen bonds and salt bridges (Vogt et al., "Protein Thermal Stability, Hydrogen Bonds, and Ion Pairs," *J. Mol. Biol.* 269:631-43 (1997), which is hereby incorporated by reference in its entirety) suggests that an opposite approach with PhyA would improve its heat stability. The thermostability of PhyA was indeed enhanced by adopting selected hydrogen bonding and ionic interactions from the corresponding positions in Afp. Based on the structural analysis of PhyA (Guex, "SWISS-MODEL and the Swiss-PdbViewer: An Environment for Comparative Protein Modeling," *Electrophoresis* 18:2714-23 (1997), which is hereby incorporated by reference in its entirety), the double mutation in mutant PhyA-A58E/P65S introduced two new hydrogen bonds with distances of 3.01 Å and 3.66 Å, respectively, as shown in FIG. 6A. Since both amino acids are located in the loop region, the two hydrogen bonds strengthen the formation of the protein tertiary structure. The single mutant PhyA-A58E and the double mutant PhyA-A58E/P65S were made to test this hypothesis. However, only the double mutations, but not the single one, showed a detectable increase in thermostability over the wild type after being heated at 80° C. for 10 minutes. This was somewhat expected since E58 cannot form a hydrogen bond with P65, while E58/S65 can restore the hydrogen bond network. The Q191R substitution stabilizes the structure via a salt bridge between Arg191 and Asp184, although there is no hydrogen bond formed between these amino acid residues, presumably because Pro189 restrains the conformation, as shown in FIG. 6B. Similarly, the T271R substitution stabilizes the structure via a salt bridge between R271 and D267, as shown in FIG. 6C.

As described in Examples 1-14 of the present invention, each of these mutations has also been found to contribute to the protein's thermostability to a different extent. Q191R and T271R did not dramatically increase the protein's thermostability, while the A58E/P65S double substitution exerted a greater impact. This is probably because A58 and P65 are located in the loop region, while Q191 and T271 are both located in the more rigid α-helix regions. Since the secondary structure change in the loop region directly affects the tertiary structure of the protein, it was considered that mutation in loop regions have a greater effect on thermostability than mutations in the α-helix regions. The present invention demonstrates that the stabilizing effect of each single mutant was additive. It is proposed that the amino acid substitutions in mutants with enhanced thermal stability reinforce the quaternary structure of the enzyme by forming an extended network of inter- and intra-subunit ion pairs and salt bridges, mediated by water molecules (Bogin et al., "Structural Basis for the Enhanced Thermal Stability of Alcohol Dehydrogenase Mutants from the Mesophilic Bacterium *Clostridium beijerinckii*: Contribution of Salt Bridging," *Protein Sci.* 11:2561-74 (2002), which is hereby incorporated by reference in its entirety).

Numerous studies have shown that electrostatic and hydrogen bonding interactions in thermophilic proteins are responsible for much of the increased stability over their mesophilic counterparts (Acharya et al., "Structural Basis of Selection and Thermostability of Laboratory Evolved *Bacillus subtilis* Lipase," *J. Mol. Biol.* 341:1271-81 (2004); Karshikoff & Ladenstein, "Proteins from Thermophilic and Mesophilic Organisms Essentially Do Not Differ in Packing," *Protein Eng.* 11:867-72 (1998); Ladenstein & Antranikian, "Proteins from Hyperthermophiles: Stability and Enzymatic Catalysis Close to the Boiling Point of Water," *Adv. Biochem. Eng./Biotechnol.* 61:37-85 (1998); Scandurra et al., "Protein Thermostability in Extremophiles," *Biochimie* 80:933-41 (1998); Szilagyi & Zavodszky, "Structural Differences Between Mesophilic, Moderately Thermophilic and Extremely Thermophilic Protein Subunits: Results of a Comprehensive Survey," *Structure* 8:493-504 (2000); Tigerstrom et al., "Effects of a Novel Disulfide Bond and Engineered Electrostatic Interactions on the Thermostability of Azurin," *Biochem.* 43:12563-74 (2004); Vogt & Argos, "Protein Thermal Stability: Hydrogen Bonds or Internal Packing?," *Fold. Des.* 2:S40-S46 (1997); Vogt et al., "Protein Thermal Stability, Hydrogen Bonds, and Ion Pairs," *J. Mol. Biol.* 269:631-43 (1997), which are hereby incorporated by reference in their entirety). The fractional polar atom surface area and the number and type of hydrogen bonds and salt links have been compared in sixteen families of proteins with different thermal stability (Vogt et al., "Protein Thermal Stability, Hydrogen Bonds, and Ion Pairs," *J. Mol. Biol.* 269:631-43 (1997), which is hereby incorporated by reference in its entirety). In most of these families, the increased thermal stability is correlated with a higher number of hydrogen bonds. Thus, hydrogen bonding is postulated to be the most important factor for thermal stability in proteins. The number of ion pairs is also found to be associated with thermal stability, but the correlation is not as strong as with hydrogen bonding (Vogt et al., "Protein Thermal Stability, Hydrogen Bonds, and Ion Pairs," *J. Mol. Biol.* 269:631-43 (1997), which is hereby incorporated by reference in its entirety). Since PhyA is a commercially available phytase supplement that needs to resist heat inactivation during feed pelleting (Mullaney et al., "Advances in Phytase Research," *Adv. Appl. Microbiol.* 47:157-99 (2000), which is hereby incorporated by reference in its entirety), it is important for practical reasons to note that the melting temperature of the PhyA mutant with the highest thermostability, PhyA-A58E/P65S/Q191R/T271R, is 7° C. higher than that of wild type PhyA. Since non-covalent interactions (including hydrogen bonding, and electrostatic and van der Waals interactions) primarily affect temperature-induced denaturing of proteins (ROBERT K. SCOPES, PROTEIN PURIFICATION (3d ed. 1994), which is hereby incorporated by reference in its entirety), the enhanced thermo-tolerance of PhyA-A58E/P65S/Q191R/T271R could be attributed to the hydrogen bonding and salt bridges introduced by the four amino acid substitutions. The two peaks seen in the thermogram may represent independent folding of the two protein domains (the α domain and the α/β domain (Kundu et al., "Alcohol and Temperature Induced Conformational Transitions in Ervatamin B: Sequential Unfolding of Domains," *J. Biochem. Mol. Biol.* 35:155-64 (2002), which is hereby incorporated by reference in its entirety)).

The point mutations made in PhyA to improve thermal stability did not produce negative impacts on its catalytic properties. Although improving enzyme thermostability at high temperatures is usually associated with reduced specific activities at low temperatures (Shoichet et al., "A Relationship Between Protein Stability and Protein Function," *PNAS* 92:452-6 (1995), which is hereby incorporated by reference in its entirety), four of the PhyA mutants with improved thermal stability had no loss of specific activity at 37° C. compared to that of the wild type. Presumably, all the substitutions occur in regions far away from the active site and exert little effect on the active site (Kostrewa et al., "Crystal Structure of *Aspergillus niger* pH2.5 Acid Phosphatase at 2.4 Å Resolution," *J. Mol. Biol.* 288:965-74 (1999), which is hereby incorporated by reference in its entirety). Although the 20 to 30% reduction in $K_m$ toward substrate of sodium phytate in the mutants PhyA-A58E/P65 S and PhyA-A58E/P65S/Q191R/T271R compared with the wild type is generally considered insignificant in enzymology, the four PhyA thermostable mutants showed higher efficiency in hydrolysis of phytate phosphorus from soybean meal at both pH 3.5 and 5.5. This is an especially desired feature for phytase since soybean meal, a commonly used animal feed ingredient, is the major source of dietary phytate for swine and poultry (Cromwell, "Biological Availability of Phosphorus in Feedstuffs for Swine," *Feedstuffs* 52:14-16 (1980), which is hereby incorporated by reference in its entirety). Neither Afp nor PhyA mutants displayed shifts in pH activity profiles, optimal pH, or optimal temperature compared to the respective wild type enzymes. Changing the charge of residues in the substrate binding site of PhyA has been shown to shift its pH profile (Mullaney et al., "Site-directed Mutagenesis of *Aspergillus niger* NRRL 3135 Phytase at Residue 300 to Enhance Catalysis at pH 4.0," *Biochem. Biophys. Res. Commun.* 297:1016-20 (2002), which is hereby incorporated by reference in its entirety). As none of the substitutions described in Examples 1-14 of the present invention occurred in the substrate binding site, it is conceivable that the pH profiles of all mutants remained unchanged. The lack of concurrent changes in optimal temperature in Afp or thermostable PhyA mutants indicates that these two parameters are independent of each other.

In summary, the present Examples provide experimental evidence to illustrate the structural basis for the superior thermal stability of Afp to PhyA by removing the predicted hydrogen bonding or salt bridge (Xiang et al., "Crystal Structure of a Heat-resilient Phytase from *Aspergillus fumigatus*, Carrying a Phosphorylated Histidine," *J. Mol. Biol.* 339:437-45 (2004), which is hereby incorporated by reference in its entirety). In addition, the introduced unique tertiary structure from Afp to PhyA by rational protein engineering resulted in significant improvement in thermal stability and an increase in the melting temperature of PhyA. Contrary to the conventional view on stability-function incompatibility (Shoichet et al., "A Relationship Between Protein Stability and Protein Function," *PNAS* 92:452-6 (1995), which is hereby incorporated by reference in its entirety), the gain of phytase thermostability of PhyA at high temperatures did not compromise its function at the body (low) temperature of animals. In fact, the PhyA mutants with improved thermostability also displayed slightly better substrate binding affinity to sodium phytate and greater efficiency in hydrolyzing phytate phosphorus from soybean meal. These combined improvements make the mutants one step closer to be an "ideal phytase" (Lei & Stahl, "Biotechnological Development of Effective Phytases for Mineral Nutrition and Environmental Protection," *Appl. Microbiol. Biotechnol.* 57:474-81 (2001), which is hereby incorporated by reference in its entirety).

Example 15

Media and Reagents

Bacterial and yeast strains, plasmids, and primers used in Examples 15-26 are listed in Table 4. *Escherichia coli* DH5α and XL1-Blue were cultured at 37° C. in LB medium. *Pichia pastoris* X33 was cultured at 30° C. in YPD medium (Invitrogen, San Diego, Calif.). Zeocin (Invitrogen, San Diego, Calif.) was added at 100 μg ml$^{-1}$ YPD medium for yeast and 25 ug ml$^{-1}$ LB medium for *E. coli*. Restriction enzymes were obtained from Promega (Madison, Wis.). Oligonucleotides were synthesized at MWGbiotech (High Point, N.C.). Phytic acid (inositol hexaphosphoric acid) dodecasodium salt from rice (p-3138), ammonium molybdate tetrahydrate (A-7302) and L-ascorbic acid (A-0278) were purchased from Sigma (St. Louis, Mo.). Sulfuric acid (A300-212) and trichloroacetic acid (A322) were purchased from Fisher (Pittsburgh, Pa.). Automatic DNA sequencing was performed at Cornell Biotechnology Center.

TABLE 4

Strains, plasmids and synthetic oligonucleotides

| Strains and plasmids | Relevant genotypes | Reference |
|---|---|---|
| Strains | | |
| DH5α | *E. coli*, α-complementation | Stratagene |
| XL-1 Blue | *E. coli* strain, recA1 endA1 gyrA96 thi-1 hsdR17 supE44 | Stratagene |
| *P. pastoris* X33 | protein expression host | Invitrogen |
| Plasmids | | |
| pGAPZα | ColE1 ori ZeoR, for integration in *P. pastoris* | Invitrogen |
| pGAPZα-phyA | phyA fragment cloned into the EcoRI and XbaI sites of pGAPZα | Invitrogen |
| pPhyA22 | A58E/p65S/Q191R/E228K/T271R substitutions of phyA in pGAPZα-phyA | Examples 15-26 |
| pPhyA23 | A58E/P65S/S149P/Q191R/E228K/T271R substitutions of phyA in pGAPZα-phyA | Examples 15-26 |
| pPhyA24 | A58E/P65S/F131L/S149P/Q191R/E228K/T271R substitutions of phyA in pGAPZα-phyA | Examples 15-26 |
| pPhyA25 | A58E/P65S/K112R/F131L/S149P/Q191R/E228K/T271R substitutions of phyA in pGAPZα-phyA | Examples 15-26 |
| pPhyA26 | A58E/P65S/K112R/F131L/S149P/Q191R/K195R/E228K/T271R substitutions of phyA in pGAPZα-phyA | Examples 15-26 |
| pPhyA27 | A58E/P65S/Q191R/T271R/K300E substitutions of phyA in pGAPZα-phyA | Examples 15-26 |
| pPhyA28 | A58E/P65S/K112R/F131L/S149P/Q191R/K195R/E228K/T271R/K300E substitutions of phyA in pGAPZα-phyA | Examples 15-26 |
| Oligonucleotides | | |
| K112R-F | 5'-CCTTTGACGGAAGATATGCCTTCCT-3' (SEQ ID NO: 16) | |
| K112R-R | 5'-AGGAAGGCATATCTTCCGTCAAAGG-3' (SEQ ID NO: 17) | |
| F131L-F | 5'-ACCTGACTCCCCTCGGAGAACAGGA-3' (SEQ ID NO: 18) | |
| F131L-R | 5'-TCCTGTTCTCCGAGGGGAGTCAGGT-3' (SEQ ID NO: 19) | |
| S149P-F | 5'-AGCGGTACGAACCGCTCACAAGGAA-3' (SEQ ID NO: 20) | |
| S149P-R | 5'-TTCCTTGTGAGCGGTTCGTACCGCT-3' (SEQ ID NO: 21) | |
| K195R-F | 5'-GATCGTCGCCCAGGATCGACGTGGT-3' (SEQ ID NO: 22) | |
| K195R-R | 5'-ACCACGTCGATCCTGGGCGACGATC-3' (SEQ ID NO: 23) | |
| E228K-F | 5'-CCGATACCGTCAAAGCCAATTTCAC-3' (SEQ ID NO: 24) | |
| E228K-R | 5'-GTGAAATTGGCTTTGACGGTATCGG-3' (SEQ ID NO: 25) | |
| K300E-F | 5'-TCCAGTCCTTGGAAAAGTATTACGG-3' (SEQ ID NO: 26) | |
| K300E-R | 5'-CCGTAATACTTTTCCAAGGACTGGA-3' (SEQ ID NO: 27) | |

Example 16

Site-Directed Mutagenesis

Site-directed mutagenesis of *A. niger* phyA gene was conducted using QuikChange® Site-Directed Mutagenesis Kit (Stratagene). Double stranded, dam-methylated plasmid DNA with the gene of interest isolated from *E. coli* strains and a pair of complementary primers containing the desired point mutation were used. The mutagenesis primers were extended by pfuTurbo DNA polymerase in a thermocycling process (95° C. for 30 seconds; 12 cycles at 95° C. for 30 seconds, 55° C. for 1 minute, and 68° C. for 1 minute per kb of plasmid DNA length). The product was treated with DpnI at 37° C. for 1 hour to remove methylated and hemimethylated parental DNA templates. The nicked plasmid DNA containing the desired mutations was then translated into *E. coli* XL1 Blue cells, where the nick is repaired by the cell. Plasmids containing the mutations were verified by automated DNA sequencing at Cornell Biotechnology Center.

Example 17

Protein Expression

*Pichia pastoris* X33 was used as an expression host. The wild type *A. niger* phytase gene and seven mutants were cloned in pGAPZα vector and transformed into *P. pastoris* X33 by electroporation. The wild type *A. niger* phytase and the seven variants were expressed in *P. pastoris* under the control of a constitutive promoter GAP. Individual transformants were grown in YPD expression medium. Cells were grown at 30° C. for 48 to 72 hours with aeration (220 rpm) until the medium O.D.$_{600}$ values reached 20.

Example 18

Purification of *A. niger* Phytase

After cultures of wild type and mutant PhyA transformants were centrifuged at 12,000 g for 30 minutes to remove cell debris, the supernatants were concentrated approximately 20-fold by ultrafiltration. The concentrate was subjected to DEAE cation-exchange chromatography (Sigma). DEAE column was balanced with 1000 ml of 10 mM Tris-HCl buffer (pH 7.4). The proteins were eluted with 300 ml of an elution buffer (10 mM Tris-HCl, pH 7.4) with a linear gradient of NaCl from 0 to 0.3 M. The flow-through fractions were collected by an automatic fraction collector. The fraction profiles of O.D.$_{280}$ and phytase activity were checked to determine the desired protein peaks. The peak fractions were pooled and concentrated down to less than 2 ml by Amicon centrifugal filter device and then loaded onto Sephadex100 sizing column (Sigma) previously equilibrated with 10 mM Tris-HCl buffer (pH 7.4) containing 0.15 M NaCl. Peak fractions were stored at −20° C. and used for further characterization.

Example 19

Biochemical Characterization of the Expressed Phytases

Phytase activity assays were conducted as described in Han et al., "Expression of an *Aspergillus niger* Phytase Gene (phyA) in *Saccharomyces cerevisiae*," *Appl. Environ. Microbiol.* 65:1915-8 (1999), which is hereby incorporated by reference in its entirety. The pH activity profile of phytase was determined at 37° C. using two different buffers, 0.2 M glycine-HCl buffer for pH 2.0-3.0 and 0.2 M citrate buffer for pH 3.5-6.5 (Han & Lei, "Role of Glycosylation in the Functional Expression of an *Aspergillus niger* Phytase (phyA) in *Pichia pastoris*," *Arch. Biochem. Biophys.* 364:83-90 (1999); Han et al., "Expression of an *Aspergillus niger* Phytase Gene (phyA) in *Saccharomyces cerevisiae*," *Appl. Environ. Microbiol.* 65:1915-8 (1999), which are hereby incorporated by reference in their entirety). Optimal temperature of phytase was tested using 0.2 M citrate buffer at pH 5.5. Thermal stability of phytase was tested using both the culture supernatants and purified phytase proteins. For supernatants, the samples were diluted with 0.2 M citrate buffer (pH 5.5) to 0.2 unit of phytase activity per ml. For purified proteins, the samples were diluted with 0.2 M citrate buffer (pH 5.5) to 10 μg of phytase protein per ml. Concentration of the purified proteins was determined by Lowry assay (Lowry et al., "Protein Measurement with the Folin Phenol Reagent," *J. Biol. Chem.* 193:265-75 (1951), which is hereby incorporated by reference in its entirety). The diluted samples were incubated for 10 minutes at each of the following temperatures: 50, 60, 70, 80, 90, and 100° C. Immediately after heat treatment, the samples were placed on ice for 30 minutes (Han & Lei, "Role of Glycosylation in the Functional Expression of an *Aspergillus niger* Phytase (phyA) in *Pichia pastoris*," *Arch. Biochem. Biophys.* 364:83-90 (1999); Han et al., "Expression of an *Aspergillus niger* Phytase Gene (phyA) in *Saccharomyces cerevisiae*," *Appl. Environ. Microbiol.* 65:1915-8 (1999), which are hereby incorporated by reference in their entirety). Phytase activity was measured at 37° C. and pH 5.5 as described above.

Example 20

Kinetic Parameters, $K_m$ and $V_{max}$

Kinetic parameters, $K_m$ and $V_{max}$, of selected phytases were determined at both pH 3.5 and pH 5.5. Purified samples were diluted with 0.2 M citrate buffer (pH 4.0 or 5.5) to a final concentration of 0.1 unit of phytase activity ("U") per ml. Phytase activity assays were carried out using phytic acid dodecasodium salts as the substrate at 13 different concentrations (2.5, 5, 7.5, 10, 25, 50, 75, 100, 250, 500, 750, 1,000, and 2,500 μM). Four parallel series of phytase reactions were carried out with different phytase hydrolysis reaction times: 5, 10, 15, and 20 minutes. Data were analyzed as follows: i) a plot of phytase activity versus reaction time to calculate initial velocities (μmol/min); ii) a plot of initial velocities versus substrate concentrations ($V_0$ VS [S]); iii) a reciprocal plot of $V_0$ and [S] to make a Lineweaver-Burk plot and calculation of the $K_m$ and $V_{max}$, respectively.

Example 21

Construction of PhyA Mutants

In order to further improve the pH optima of the thermostable PhyA mutants designed as described in Examples 1-14, site-directed mutagenesis was used to introduce E228K and K300E substitutions into the thermostable PhyA mutant PhyA-A58E/P65S/Q191R/T271R. Accordingly, two new mutants were generated: PhyA-A58E/P65S/Q191R/E228K/T271R ("PhyA22"), and PhyA-A58E/P65S/Q191R/T271R/K300E ("PhyA27").

To further improve the thermostability of the PhyA mutants, four additional substitutions (K112R, F131L, S149P, and K195R) that were previously identified to improve thermostability were added. Based on protein structural information, these four substitutions were added sequentially, resulting in four new mutants: PhyA-A58E/P65S/S149P/Q191R/E228K/T271R ("PhyA23"), PhyA-A58E/P65S/F131L/S149P/Q191R/E228K/T271R ("PhyA24"), PhyA-A58E/P65S/K112R/F131L/S149P/Q191R/E228K/T271R ("PhyA25"), and PhyA-A58E/P65S/K112R/F131L/S149P/Q191R/K195R/E228K/T271R ("PhyA26").

Meanwhile, K300E was added to PhyA26 to make: PhyA-A58E/P65S/K112R/F131L/S149P/Q191R/K195R/E228K/T271R/K300E ("PhyA28").

The mutants and primers described herein are summarized in Table 4.

Example 22

Substitutions of E228K and K300E in PhyA Enhance its Enzyme Activity at pH 3.5

Up to 10 amino acid substitutions were made in PhyA. Some of them dramatically changed the pH dependent specific activity. The specific activities for five mutants that contained the E228K substitution (PhyA22, PhyA23, PhyA24, PhyA25, and PhyA26) were about 40 to 60% higher than that of the wild type PhyA at pH 3.5, as shown in Table 5. These mutants also showed drastically different pH profiles from that of the wild type PhyA. The pH optima of these five mutants were shifted from pH 5.5 to 4.0. In addition, the ratios of phytase activities at pH 3.5 to 5.5 for these mutants were increased from 0.4 (the wild-type) to ~1.5, as shown in FIGS. 7A-C.

TABLE 5

Specific activities and kinetic parameters of the wild type PhyA and PhyA variants.

| | [U/mg] (mean ± S.D.) | |
|---|---|---|
| | pH 5.5 | pH 3.5 |
| WT PhyA | 81.2 ± 0.6 | 32.5 ± 0.2 |
| PhyA22 | 34.4 ± 0.4 | 53.4 ± 0.6 |
| PhyA23 | 37.7 ± 0.3 | 51.0 ± 0.4 |
| PhyA24 | 30.4 ± 1.3 | 42.5 ± 1.9 |
| PhyA25 | 36.5 ± 0.5 | 49.3 ± 0.6 |
| PhyA26 | 31.4 ± 0.5 | 42.4 ± 0.7 |
| PhyA27 | 106.4 ± 2.4 | 71.3 ± 1.6 |
| PhyA28 | 54.7 ± 1.0 | 32.8 ± 0.6 |

The pH optima of mutants PhyA27 and PhyA28 remained at pH 5.5. However, the activity dip at pH 3.5 was eliminated and the ratios of activities at pH 3.5 to 5.5 were increased from 0.4 to about 0.6, as shown in FIG. 7D. Moreover, the specific activity for PhyA27 at pH 3.5 was more than two-fold higher than that of the wild type PhyA, as shown in Table 5.

Example 23

Mutations in the Substrate Binding Site do not Affect Protein Thermostability

The mutant PhyA-A58E/P65S/Q191R/T271R was shown to retain significantly higher initial activity than that of the wild type PhyA after being heated at various temperatures for 10 minutes. To assess the effect of other substitutions on heat inactivation, residual phytase activity was measured for seven mutants and the wild type PhyA after being heated at different temperatures between 50° C. to 100° C. for 10 minutes. As shown in FIG. 8A, two mutants that contained substitutions in the substrate binding site, PhyA22 and PhyA27, showed significantly improved residual activity (P<0.01) over that of the wild type PhyA after being heated at temperatures >80° C. This indicates that E228K and K300E do not impair or improve the thermostability of mutant PhyA-A58E/P65S/Q191R/T271R.

Example 24

Substitutions of S149P and F131L Cumulatively Enhance PhyA Thermostability

As shown in FIGS. 8A-C, five mutants (PhyA23, PhyA24, PhyA25, PhyA26, and PhyA28) showed significantly improved residual activity (P<0.01) over wild type PhyA and mutant PhyA-A58E/P65S/Q191R/T271R after being heated at temperatures higher than 70° C. Among these mutants, PhyA23 and PhyA24 showed the most dramatic improvement in thermostability. PhyA23 showed nearly 30% greater residual activity after heat treatment at 100° C. than the wild type. Adding the F131L residue substitution to PhyA23 (resulting in PhyA24) slightly increased its remaining activity. PhyA24 retained nearly 80% of its initial activity after heat treatment at 100° C. However, the addition of substitutions K112R and K195R did not further improve the thermostability of PhyA24. The phytase activity of each mutant was measured directly at a series of temperatures between 25 and 75° C. The optimal temperature for each mutant remained the same (55° C.) as that of the wild type PhyA, as shown in FIGS. 9A-C.

Example 25

Substitutions of E228K and K300E Affect Kinetic Parameters ($K_m$ and $V_{max}$)

Steady state kinetic measurements revealed that the apparent $K_m$ of the wild type PhyA was 171.9 and 122.4 µM at pH 5.5 and 4.0, respectively, when sodium phytate was the substrate. The $K_m$ of the mutants containing the E228K substitution (i.e., PhyA22 and PhyA23) decreased, respectively, to 108.3 and 107.6 µM at pH 5.5, and to 82.7 and 86.4 µM at pH 4.0. The apparent $K_m$ at pH 4.0 of mutants PhyA22, PhyA23, and PhyA27 decreased by 32%, 29%, and 24%, respectively, compared to that of the wild type PhyA. At pH 5.5, while $K_m$ of PhyA22 and PhyA23 decreased by one third, the $K_m$ of PhyA27 was two-fold higher than that of the wild type PhyA. The $V_{max}$ values for PhyA22, PhyA23, and PhyA27 were all higher than that of the wild type PhyA at pH 4.0, but lower than that of the wild type PhyA at pH 5.5, as shown in Table 6.

TABLE 6

Kinetic parameters of the wild type PhyA and PhyA variants.

| | Km (µM) | | Vmax (µM/min) | |
|---|---|---|---|---|
| | pH 4.0 | pH 5.5 | pH 4.0 | pH 5.5 |
| WT PhyA | 122.4 | 171.9 | 119.1 | 126.6 |
| PhyA22 | 82.7 | 108.3 | 172.4 | 108.7 |
| PhyA23 | 86.4 | 107.6 | 129.9 | 90.1 |
| PhyA27 | 93.4 | 384.7 | 129.9 | 123.5 |

Example 26

Five Mutants Tested Show Improve Hydrolysis Efficiency of Phytate in Soybean Meal The efficiency for soy phytate hydrolysis at pH 5.5 and pH 3.5 was compared among the wild type PhyA and mutants PhyA22, PhyA23, PhyA24, PhyA25, PhyA26, PhyA27, and PhyA28. The E228K residue substitution had a pronounced effect on the hydrolysis of phytate in soybean meal. Five mutants that contained the E228K substitution were more efficient in catalyzing the hydrolysis of soy phytate at both pH 5.5 ($P<0.05$) and pH 3.5 ($P<0.01$). Among them, PhyA22 showed the greatest release of inorganic phosphorus, which was 1.3- and 2.8-fold higher than that from the wild type PhyA at pH 5.5 and pH 3.5, respectively, as shown in FIG. 10.

Discussion of Examples 15-26

For proteins with known three-dimensional structures, site-directed mutagenesis has become a very useful tool to study the relationship of structure and function (Declerck et al., "Hyperthermostabilization of *Bacillus lichniformis* α-Amylase and Modulation of Its Stability Over a 50° C. Temperature Range," *Protein Eng.* 16:287-93 (2003); Leemhuis et al., "Improved Thermostability of *Bacillus circulans* Cyclodextrin Glycosyltransferase by the Introduction of a Salt Bridge," *Proteins* 54(1):128-34 (2004); Liu et al., "Replacement and Deletion Mutations in the Catalytic Domain and Belt Region of *Aspergillus awamori* Glucoamylase to Enhance Thermostability," *Protein Eng.* 13:655-9 (2000); Sriprapundh et al., "Molecular Determinants of Xylose Isomerase Thermal Stability and Activity: Analysis of Thermozymes by Site-directed Mutagenesis," *Protein Eng.* 13:259-65 (2000), which are hereby incorporated by reference in their entirety). Although many general rules have been proposed for the molecular determinants of protein thermostability (Vogt et al., "Protein Thermal Stability, Hydrogen Bonds, and Ion Pairs," *J. Mol. Biol.* 269:631-43 (1997), which is hereby incorporated by reference in its entirety), it is still difficult to precisely predict the effect of certain residue substitutions on protein thermostability. Directed evolution (Arnold et al., "How Enzymes Adapt: Lessons from Directed Evolution," *Trends Biochem. Sci.* 26:100-6 (2001); Stemmer, "DNA Shuffling by Random Fragmentation and Reassembly: In vitro Recombination for Molecular Evolution," *Proc. Nat'l Acad. Sci. USA* 91:10747-51 (1994), which are hereby incorporated by reference in their entirety) provides an alternative approach in protein engineering, in particular in the absence of a thorough understanding of the crystal structure (Cherry & Fidantsef, "Directed Evolution of Industrial Enzymes: An Update," *Curr. Opin. Biotechnol.* 14:438-43 (2003), which is hereby incorporated by reference in its entirety). Examples 1-26 of the present invention show the effectiveness in combining both site-directed mutagenesis and directed evolution approaches for improving thermostability and pH optima of PhyA.

Several residue substitutions that affect the pH profile and thermostability of PhyA have previously been identified. To combine the improvement brought by each single mutation, seven PhyA mutants were constructed sequentially with different combinations of these mutations. Among ten substitutions, only E228K and K300E were found to affect the pH profile (see FIGS. 11A-C). Two other substitutions, S149P and F131L, further improved the thermostability. By combining these mutations, two resulting PhyA mutants, PhyA23 and PhyA24, with substantially enhanced thermostability and desired pH profile shifts were generated.

The pyrrolidine ring of proline is known to restrict the configurations of itself and the preceding residues. Thus, proline stabilizes the protein by lowering the entropy difference between the folded and unfolded states (Matthews et al., "Enhanced Protein Thermostability from Site-directed Mutations that Decrease the Entropy of Unfolding," *Proc. Nat'l Acad. Sci. USA* 84:6663-7 (1987), which is hereby incorporated by reference in its entirety). It has been shown in many studies that substitution of a selected residue by proline could increase protein thermostability as long as no steric hindrance is caused by the newly introduced proline. Replacement of nine residues of *Bacillus cereus* oligo-1,6-glucosidase with proline remarkably enhanced the thermostability of these mutants, especially when proline residues were introduced at second sites of beta turns or at N-caps of alpha helices (Watanabe et al., "Multiple Proline Substitutions Cumulatively Thermostabilize *Bacillus cereus* ATCC7064 Oligo-1,6-glucosidase. Irrefragable Proof Supporting the Proline Rule," *Eur. J. Biochem.* 226(2):277-83 (1994), which is hereby incorporated by reference in its entirety). Introduction of proline into the N-terminus of the active site helix of *Bacillus stearothermophilus* neutral protease increased the half-survival temperature by 7.5° C. (Nakamura et al., "Improving the Thermostability of *Bacillus stearothermophilus* Neutral Protease by Introducing Proline into the Active Site Helix," *Protein Eng.* 10:1263-69 (1997), which is hereby incorporated by reference in its entirety). To investigate the effect of introducing a proline residue on the stabilization of PhyA, the N-terminal residue of a one turn α-helix located in the α/β domain, Ser149, was substituted with Pro, resulting in the mutant PhyA23. The residues preceding Ser149 consist of a three-residue short loop that links the α-helix spanning residues 130-145 and the α-helix spanning residues 149-151, as shown in FIG. 12A. Substitution of Ser149 with proline (FIG. 12B) was expected to restrain the flexibility of the loop. Thermal inactivation tests showed that PhyA23 retained higher residual activity not only than that of the wild type PhyA, but also than that of PhyA22, which differed from PhyA23 only in the lack of the S149P substitution. This indicates that the S149P single substitution leads to a substantial increase in thermostability.

Leucine is a favorable residue for hydrophobic packing of α-helices in soluble proteins (Eilers et al., "Internal Packing of Helical Membrane Proteins," *Proc. Nat'l Acad. Sci. USA* 97:5796-801 (2000), which is hereby incorporated by reference in its entirety). Many studies have shown that substitution of other residues with leucine results in increased thermostability. Each of three single substitutions, A23L, I140L, and V108I, in yeast cytosine deaminase (yCD), enhanced the apparent $T_m$ by 2° C. The triple substitutions had a synergistic effect on the thermostability, and increased the $T_m$ by 10° C. (Korkegian et al., "Computational Thermostabilization of an Enzyme," *Science* 308:857-60 (2005), which is hereby incorporated by reference in its entirety). A L290F substitution at the end of a β-strand in ribulose-1,5-bisphosphate carboxylase/oxygenase reduced the thermostability of the mutant enzyme at 35° C. both in vivo and in vitro (Chen et al., "Thermal Instability of Ribulose-1,5-bisphosphate Carboxylase/Oxygenase from a Temperature-conditional Chloroplast Mutant of *Chlamydomonas reinhardtii*," *Plant Physiol.* 101:1189-94 (1993), which is hereby incorporated by reference in its entirety). As shown in FIG. 12C, the Phe131 residue is located at the second site of the N-terminal of an α-helix in the α/β domain of PhyA. Mutant PhyA24 was made by introducing a F131L substitution into PhyA23, as shown in FIG. 12D.

Heat inactivation assays show that PhyA24 retains slightly higher residual activity after being heated at various temperatures. This increase in thermostability is presumably due to the fact that the substitution of the bulky Phe131 residue with the hydrophobic leucine residue facilitates local structure folding. As shown in FIGS. 12E-F, when Lys112 was substituted with arginine in PhyA, a hydrogen bond with a distance of 2.56 Å was predicted to form between Arg112 and Tyr113. However, the enthalpy contribution did not seem to stabilize the protein as expected.

The effects of the ten residue substitutions on pH profiles and thermostability of PhyA were also studied. Among the ten mutations, only two of them, Glu228 and Lys300, are located at the substrate binding site and directly interact with the negatively charged substrate phytate. The acidic residue Glu228 was substituted with a basic residue (i.e., lysine) to eliminate the electrostatic repulsion with phytate. The $K_m$ of PhyA mutants containing the E228K substitution decreased at both pH 5.5 and pH 4.0. This indicates that the binding affinity of the mutant PhyA for sodium phytate was indeed increased due to the E228K substitution. On the other hand, the positively charged residue Lys300 was mutated to glutamic acid (Kim et al., "Shifting the pH Profile of *Aspergillus niger* PhyA Phytase to Match the Stomach pH Enhances Its Effectiveness as an Animal Feed Additive," *Appl. Environ. Microbiol.* 72:4397-403 (2006), which is hereby incorporated by reference in its entirety), which has an isoelectric point of 4.7. So at pH 5.5, the mutant PhyA27, which contains the K300E substitution, does not favor phytate, resulting in an increased $K_m$ compared to that of the wild type PhyA (384 µM versus 171 µM). Lys300 is neutral at pH 4.0 and was expected to favor the negatively charged phytate, as confirmed by the $K_m$ decrease. Soy phytate hydrolysis studies showed that all five E228K-containing mutants had higher hydrolysis efficiency toward the substrate in soybean meal at both pH 5.5 and 3.5.

In summary, the thermostability of a fairly thermostable phytase was substantially improved by adding mutations derived from directed evolution. Above this, the pH optima of the thermostable mutants have been shifted to the acidic pH range, closer to the pH conditions of animal stomachs where feed phytate is hydrolyzed. The present invention demonstrates the potential of phytase protein engineering in changing its biochemical characteristics for practical needs. Experimental approaches and structural rationales used in Examples 1-26 may be applied to improving many other enzymes with potential industrial interests.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

---

What is claimed:

1. An isolated protein or polypeptide having phytase activity, wherein said protein or polypeptide comprises an amino acid sequence having at least 90 percent sequence identity to SEQ ID NO: 2 and containing at least one substitution of at least one amino acid residue selected from the group consisting of residue A58, P65, K112, F131, S149, Q191, K195, and T271 of SEQ ID NO: 2.

2. The isolated protein or polypeptide according to claim 1, wherein the percent sequence identity is at least 96 percent.

3. The isolated protein or polypeptide according to claim 1, wherein said at least one substitution is selected from the group consisting of A58E, P65S, K112R, F131L, S149P, Q191R, K195R, T271R, A58E/Q191R, A58E/T271R, Q191R/T271R, A58E/P65S, A58E/Q191R/T271R, and A58E/P65S/Q191R/T271R of SEQ ID NO: 2.

4. The isolated protein or polypeptide according to claim 3, wherein the at least one substitution is selected from the group consisting of A58E, P65S, F131L, S149P, Q191R, and T271R of SEQ ID NO: 2.

5. The isolated protein or polypeptide according to claim 3, wherein the at least one substitution is selected from the group consisting of A58E/Q191R, A58E/P65S, A58E/Q191R/T271R, and A58E/P65S/Q191R/T271R of SEQ ID NO: 2.

6. The isolated protein or polypeptide according to claim 1, wherein the protein or polypeptide further contains at least one substitution of at least one amino acid residue selected from the group consisting of residues E228 and K300 of SEQ ID NO: 2.

7. The isolated protein or polypeptide according to claim 6, wherein the protein or polypeptide further contains at least one substitution of at least one amino acid residue selected from the group consisting of E228K and K300E of SEQ ID NO: 2.

8. The isolated protein or polypeptide according to claim 7, wherein the at least one substitution is selected from the group consisting of A58E/P65S/Q191R/T271R/K300E, A58E/P65S/Q191R/E228K/T271R, A58E/P65S/S149P/Q191R/E228K/T271R, A58E/P65S/F131L/S149P/Q191R/E228K/T271R, A58E/P65S/K112R/F131L/S149P/Q191R/E228K/T271R, A58E/P65S/K112R/F131L/S149P/Q191R/K195R/E228K/T271R, and A58E/P65S/K112R/F131L/S149P/Q191R/K195R/E228K/T271R/K300E of SEQ ID NO: 2.

9. The isolated protein or polypeptide according to claim 8, wherein the at least one substitution is selected from the group consisting of A58E/P65S/Q191R/E228K/T271R, A58E/P65S/S149P/Q191R/E228K/T271R, A58E/P65S/F131L/S149P/Q191R/E228K/T271R, A58E/P65S/K112R/F131L/S149P/Q191R/E228K/T271R, and A58E/P65S/K112R/F131L/S149P/Q191R/K195R/E228K/T271R of SEQ ID NO: 2.

10. An animal feed composition comprising the isolated protein or polypeptide according to claim 1.

11. A foodstuff comprising an animal feed composition according to claim 10.

12. A method of feeding a monogastric animal comprising:
   feeding to the animal a foodstuff in combination with the isolated protein or polypeptide according to claim 1.

13. A method of improving the nutritional value of a foodstuff consumed by an animal, said method comprising:
   providing a foodstuff comprising myo-inositol hexakisphosphate;
   providing an isolated protein or polypeptide according to claim 1; and
   feeding to the animal the foodstuff in combination with the protein or polypeptide under conditions effective to increase the bioavailability of phosphate from phytate.

14. A method of in vitro hydrolysis of phytate, said method comprising:
   providing an isolated protein or polypeptide according to claim 1 and
   combining said protein or polypeptide with a phytate source under conditions effective to increase the bioavailability of phosphate from said phytate source.

15. A method of improving the nutritional value of a foodstuff consumed by humans, said method comprising:
   providing an isolated protein or polypeptide according to claim 1 and
   combining said protein or polypeptide with a foodstuff consumed by humans under conditions effective to increase the bioavailability of minerals from said foodstuff, wherein said minerals are selected from the group consisting of iron, zinc, phosphorus, and calcium.

16. An isolated protein or polypeptide having phytase activity, wherein said protein or polypeptide comprises the amino acid sequence of SEQ ID NO: 2, containing at least one substitution of at least one amino acid residue selected from the group consisting of residue A58, P65, K112, F131, S149, Q191, K195, and T271 of SEQ ID NO: 2.

17. An animal feed composition comprising the isolated protein or polypeptide according to claim 7.

18. A foodstuff comprising an animal feed composition according to claim 17.

* * * * *